(12) United States Patent
Matsunaga et al.

(10) Patent No.: US 8,546,291 B2
(45) Date of Patent: Oct. 1, 2013

(54) CYCLIC COMPOUND, ITS METAL COMPLEX AND MODIFIED METAL COMPLEX

(75) Inventors: Tadafumi Matsunaga, Tsukuba (JP); Nobuyoshi Koshino, Tsukuba (JP); Hideyuki Higashimura, Tsukuba (JP); Yusuke Ishii, Toda (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 242 days.

(21) Appl. No.: 12/811,025

(22) PCT Filed: Sep. 5, 2008

(86) PCT No.: PCT/JP2008/066072
§ 371 (c)(1),
(2), (4) Date: Oct. 6, 2010

(87) PCT Pub. No.: WO2009/084283
PCT Pub. Date: Jul. 9, 2009

(65) Prior Publication Data
US 2011/0015059 A1   Jan. 20, 2011

(30) Foreign Application Priority Data

Dec. 28, 2007  (JP) ................. 2007-339371

(51) Int. Cl.
  *B01J 31/22* (2006.01)
  *C07D 471/22* (2006.01)
  *C07D 487/22* (2006.01)
  *C07F 15/06* (2006.01)
  *C07F 19/00* (2006.01)
  *C07F 15/04* (2006.01)
  *C07F 1/08* (2006.01)
  *C08F 26/06* (2006.01)

(52) U.S. Cl.
  USPC ........... 502/159; 540/471; 540/465; 526/259; 502/167

(58) Field of Classification Search
  None
  See application file for complete search history.

(56) References Cited

FOREIGN PATENT DOCUMENTS

| DE | 2250377 A1 | 4/1974 |
|---|---|---|
| EP | 1988084 A1 | 11/2008 |
| EP | 2123638 A1 | 11/2009 |
| EP | 2133145 A1 | 12/2009 |
| EP | 2133336 A1 | 12/2009 |
| EP | 2136426 A1 | 12/2009 |
| WO | 2007/091616 A1 | 8/2007 |
| WO | 2008/111567 A1 | 9/2008 |
| WO | 2008/111568 A1 | 9/2008 |
| WO | 2008/111569 A1 | 9/2008 |
| WO | 2008/111570 A1 | 9/2008 |

OTHER PUBLICATIONS

Sessler et al., Chem. Eur. J. 2005, 11, 2001-2011.*
Fung Lam, et al., "Synthesis of Dinucleating Phenanthroline-Based Ligands", TETRAHEDRON, 1999, vol. 55, pp. 8377-8384.
Fung Lam, et al., "Synthesis of Acyclic Dinucleating Phenanthroline-Pyridine and Phenanthroline-Phosphine Ligands", Tetrahedron Letters, 1995, pp. 6261-6262, vol. 36, No. 35.

(Continued)

*Primary Examiner* — Melvin C Mayes
*Assistant Examiner* — Yun Qian
(74) *Attorney, Agent, or Firm* — Sughrue Mion, PLLC

(57) ABSTRACT

A compound represented by formula (1):

(1)

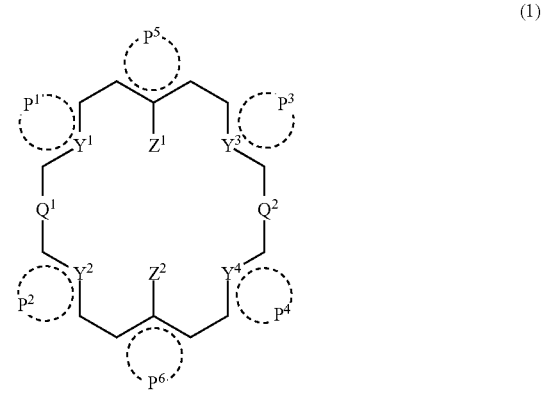

wherein $Y^1$ to $Y^4$ each independently represent any one of the following groups:

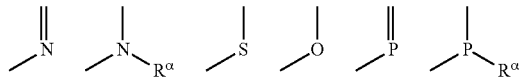

in which $R^\alpha$ represents a hydrogen atom or a monovalent hydrocarbon group; $P^1$ to $P^4$ each independently represent a group of atoms necessary for forming a heterocyclic ring together with each of $Y^1$ to $Y^4$ and the two carbon atoms adjacent to each of $Y^1$ to $Y^4$, respectively; $P^5$ and $P^6$ each independently represent a group of atoms necessary for forming a cyclic skeleton together with the carbon atom to which $Z^1$ bonds or $Z^2$ bonds and the two carbon atoms adjacent to the carbon atom to which $Z^1$ bonds or $Z^2$ bonds; $P^1$ and $P^2$, $P^2$ and $P^6$, $P^6$ and $P^4$, $P^4$ and $P^3$, $P^3$ and $P^5$, and $P^5$ and $P^1$ may further combine with each other to form a ring; $Q^1$ and $Q^2$ each independently represent a connecting group or a direct binding; and $Z^1$ and $Z^2$ each independently represent any one of the following groups;
  —$NR^\beta{}_2$, —$OR^\beta$, —$SR^\beta$, —$PR^\beta{}_2$
in which $R^\beta$ represents a hydrogen atom or a monovalent hydrocarbon group, and when plural $R^\beta$s are present, these plural $R^\beta$s may be the same or different from each other.

6 Claims, No Drawings

(56) References Cited

OTHER PUBLICATIONS

K. Brychcy, et al., "Zweikernige Kupfer(II)-Komplexe mit vollständig π-konjugiertem Makrocyclus vom Schiff-Basen-Typ: Synthesen, Strukturen, elektro- und magnetochemische Eigenschaften", Chem. Berichte, 1994, pp. 465-476, vol. 127, No. 3.

N. H. Pilkington, et al., "Complexes of Binucleating Ligands", Aust. J. Chem., Feb. 1970, pp. 2225-2236, vol. 23.

Susumu Kitagawa, et al., "Functional Porous Coordination Polymers", Angew Chem., Int. Ed., 2004, pp. 2334-2375, vol. 43.

T. Okada et al., "A Comparative Study of Organic Cobalt Complex Catalysts for Oxygen Reduction in Polymer Electrolyte Fuel Cells", Journal of Inorganic and Organometallic Polymers, vol. 9, No. 4, 1999, pp. 199-219 (XP-002384120).

T. Ichimura et al., "meta-Phenylene-bridged bis(imino nitroxide) biradicals as potential high-spin ligands", Polyhedron, vol. 22, 2003, pp. 2557-2564 (XP-002638770).

H. Brunner and S. Altmann, "Optisch aktive Stickstoffliganden mit Dendrimer-Struktur", Chemische Berichte, vol. 127, 1994, pp. 2285-2296 (XP-002638771).

H. Giesecke und J. Hocker, "Synthese von Hydroxybenzaldehyden mit Ethylentetraminen", Liebigs Annalen de Chemie., 1978, pp. 345-361 (XP-002638772).

F. Eiden und E.-A. Schaumberg, "Pyrazolo-chromone, Benzo-Di- und Tripyrazole aus Benzo-Di- und Tripyronen", Tetrahedron Letters, vol. 16, 1972, pp. 1593-1596 (XP-002638773).

H. Fischer et al., "Pyrrol-Chinon-Farbstoffe", Chemische Berichte, Verlag Chemie GMBH, Weinheim, DE, vol. 92, Jan. 1, 1959, pp. 2026-2029 (XP-001068703).

S.K. Dutta et al., "Homo- and hetero-dinuclear metal complexes of bridging ligands containing phenol and azole moieties. Structure, spectroscopy, electrochemistry and magnetochemistry", Journal of the Chemical Society, Dalton Transactions, Chemical Society, Letchworth, GB, No. 11, Jan. 1, 1996, pp. 2371-2379 (XP-009080277).

C.J. Fahrni and A. Pfaltz, "Structure and Properties of Transition-Metal Complexes with Chiral C2-Symmetric Binucleating Ligands", Helvetica Chimica Acta, vol. 81, 1998, pp. 507-524 (XP-002638774).

* cited by examiner

CYCLIC COMPOUND, ITS METAL COMPLEX AND MODIFIED METAL COMPLEX

TECHNICAL FIELD

The present invention relates to a metal complex and a modified metal complex thereof. Further, the present invention relates to a macrocyclic ligand compound capable of forming a complex.

BACKGROUND ART

Metal complexes act as catalysts in a redox reaction (redox catalyst) involving electron transfer such as an oxygenation reaction, an oxidative coupling reaction, a dehydrogenation reaction, a hydrogenation reaction, or an oxide decomposition reaction, and are used in production of organic compounds or polymer compounds. Further, the metal complexes are used in various applications including additives, modifiers, cells, sensor materials, and electroluminescence materials.

Among these metal complexes, it is known that the metal complexes including a macrocyclic compound as a ligand form a stable complex due to the effect of the large ring. For example, it is known that porphyrin complexes exhibit stability to acids, compared to non-cyclic complexes (see "Porphyrin no Kagaku" (Chemistry of Porphyrins), published by Kyoritsu Shuppan Co., Ltd. (1982)).

Further, it is known that the metal complexes having a transition metal atom as their center metals exhibit excellent catalyst activity as an oxidative coupling reaction catalyst and hydrogen peroxide decomposition catalyst (see Angewandte Chemie International Edition, 42, 6008 (2003)).

However, the metal complexes including a schiff base as a ligand, as disclosed in Angewandte Chemie International Edition, 42, 6008 (2003), exhibit insufficient stability. Especially when a reaction is conducted in the presence of acids or under heating, the metal complexes exhibit instability to acids or heat, or alternatively both acids and heat for catalyst use. Accordingly, it is strongly desired to improve stability to acids or heat so as to use the metal complexes as a catalyst.

DISCLOSURE OF INVENTION

According to the present invention, there can be provided a metal complex exhibiting excellent resistance to both acid and heat. Further, according to the present invention, there can be provided a macrocyclic compound that is useful as a ligand of the metal complex, and an intermediate of the macrocyclic compound. Furthermore, according to the present invention, it is possible to provide an electrocatalyst for fuel cells.

The present invention provides the following means:

(1) A compound represented by formula (1):

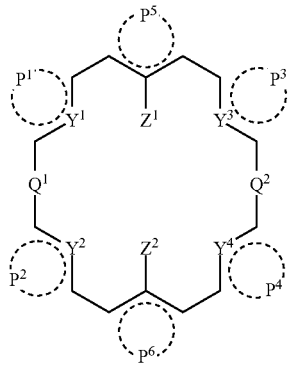

(1)

wherein $Y^1$ to $Y^4$ each independently represent any one of the following groups:

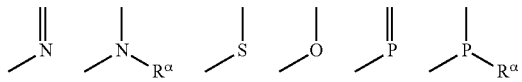

in which $R^\alpha$ represents a hydrogen atom or a monovalent hydrocarbon group; $P^1$ represents a group of atoms necessary for forming a heterocyclic ring together with $Y^1$ and the two carbon atoms adjacent to $Y^1$; $P^2$ represents a group of atoms necessary for forming a heterocyclic ring together with $Y^2$ and the two carbon atoms adjacent to $Y^2$; $P^3$ represents a group of atoms necessary for forming a heterocyclic ring together with $Y^3$ and the two carbon atoms adjacent to $Y^3$; $P^4$ represents a group of atoms necessary for forming a heterocyclic ring together with $Y^4$ and the two carbon atoms adjacent to $Y^4$; $P^5$ represents a group of atoms necessary for forming a cyclic skeleton together with the carbon atom to which $Z^1$ bonds and the two carbon atoms adjacent to the carbon atom to which $Z^1$ bonds; $P^6$ represents a group of atoms necessary for forming a cyclic skeleton together with the carbon atom to which $Z^2$ bonds and the two carbon atoms adjacent to the carbon atom to which $Z^2$ bonds; $P^1$ and $P^2$, $P^2$ and $P^6$, $P^6$ and $P^4$, $P^4$ and $P^3$, $P^3$ and $P^5$, and $P^5$ and $P^1$ may further combine with each other to form a ring; $Q^1$ and $Q^2$ each independently represent a connecting group or a direct binding; and $Z^1$ and $Z^2$ each independently represent any one of the following groups;

—$NR^\beta_2$, —$OR^\beta$, —$SR^\beta$, —$PR^\beta_2$ in which $R^\beta$ represents a hydrogen atom or a monovalent hydrocarbon group, and when plural $R^\beta$s are present, these plural $R^\beta$s may be the same or different from each other.

(2) The compound according to the above item (1), wherein, in formula (1), the group of atoms represented by $P^5$ is a group of atoms necessary for forming a phenol ring structure together with the carbon atom to which $Z^1$ bonds and the two carbon atoms adjacent to the carbon atom to which $Z^1$ bonds; and the group of atoms represented by $P^6$ is a group of atoms necessary for forming a phenol ring structure together with the carbon atom to which $Z^2$ bonds and the two carbon atoms adjacent to the carbon atom to which $Z^2$ bonds.

(3) The compound according to the above item (1) or (2), wherein, in formula (1), the group of atoms represented by $P^1$ is a group of atoms necessary for forming an aromatic heterocyclic ring together with $Y^1$ and the two carbon atoms adjacent to $Y^1$; the group of atoms represented by $P^2$ is a group of atoms necessary for forming an aromatic heterocyclic ring together with $Y^2$ and the two carbon atoms adjacent to $Y^2$; the group of atoms represented by $P^3$ is a group of atoms necessary for forming an aromatic heterocyclic ring together with $Y^3$ and the two carbon atoms adjacent to $Y^3$; and the group of atoms represented by $P^4$ is a group of atoms necessary for forming an aromatic heterocyclic ring together with $Y^4$ and the two carbon atoms adjacent to $Y^4$.

(4) The compound according to the above item (3), wherein, in formula (1), the aromatic heterocyclic ring that is formed by the group of atoms represented by $P^1$ together with $Y^1$ and the two carbon atoms adjacent to $Y^1$, the aromatic heterocyclic ring that is formed by the group of atoms represented by $P^2$ together with $Y^2$ and the two carbon atoms adjacent to $Y^2$, the aromatic heterocyclic ring that is formed by the group of atoms represented by $P^3$ together with $Y^3$ and the two carbon atoms adjacent to $Y^3$, and the aromatic heterocyclic ring that is formed by the group of atoms represented by $P^4$ together with $Y^4$ and the two carbon atoms adjacent to $Y^4$, are each a nitrogen-containing aromatic heterocyclic ring.

(5) The compound according to the above item (4), wherein the compound represented by formula (1) is a compound represented by formula (2):

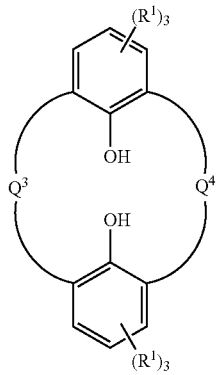

(2)

wherein, in formula (2), $R^1$ represents a hydrogen atom or a substituent, when plural $R^1$s are present, these plural $R^1$s may be the same or different from one another; and $Q^3$ and $Q^4$ each independently represent any one of the following groups:

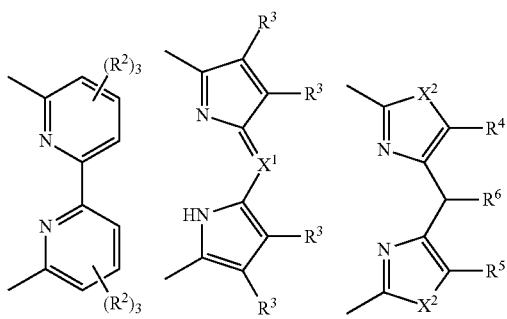

in which $R^2$ represents a hydrogen atom or a substituent, plural $R^2$s may be the same or different from one another, and $R^2$s may combine with each other to form a ring; $X^1$ represents a nitrogen atom or a trivalent group; $R^3$ represents a hydrogen atom or a substituent, plural $R^3$s may be the same or different from one another, and $R^3$s may combine with each other to form a ring; $X^2$s each independently represent a bivalent group represented by any one of the following groups:

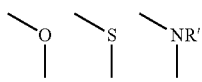

in which R' represents a hydrogen atom or a monovalent hydrocarbon group; $R^4$, $R^5$ and $R^6$ each independently represent a hydrogen atom or a substituent; and $R^4$ and $R^6$, $R^5$ and $R^6$, and $R^4$, $R^5$ and $R^6$ may combine with each other to form a ring.

(6) The compound according to the above item (5), wherein the compound represented by formula (2) is a compound represented by formula (a1):

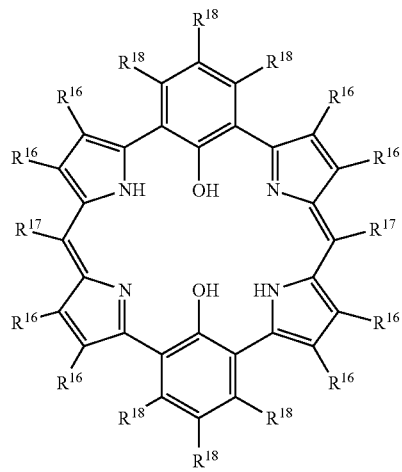

(a1)

wherein, in formula (a1), $R^{16}$ to $R^{18}$ each independently represent a hydrogen atom or a substituent, two adjacent $R^{16}$s and two adjacent $R^{18}$s each may combine with each other to form a ring, and plural $R^{16}$s to $R^{18}$s may be the same or different from one another.

(7) The compound according to the above item (5), wherein the compound represented by formula (2) is a compound represented by formula (a2):

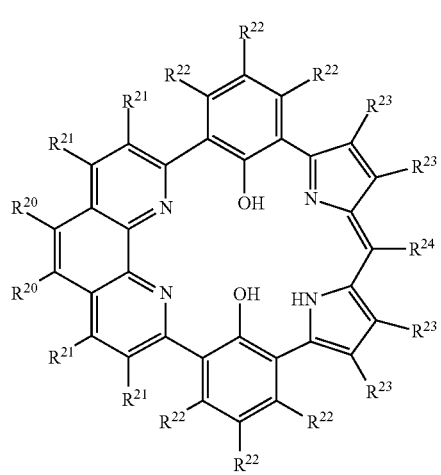

(a2)

wherein, in formula (a2), $R^{20}$ to $R^{24}$ each independently represent a hydrogen atom or a substituent, two adjacent $R^{20}$s, two adjacent $R^{21}$s, two adjacent $R^{22}$s and two adjacent $R^{23}$s each may combine with each other to form a ring, and plural $R^{20}$s to $R^{23}$s may be the same or different from one another.

(8) A polymer comprising a residue of the compound represented by formula (1).

(9) The polymer according to the above item (8), comprising the residue of the compound represented by formula (1) as a repeating unit.

(10) A compound represented by formula (3):

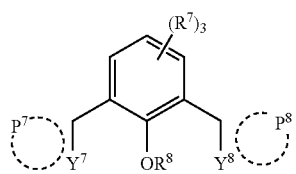

wherein, in formula (3), $R^7$ represents a hydrogen atom or a substituent, plural $R^7$s may be the same or different from one another; $R^8$ represents a hydrogen atom or a protective group; $Y^7$ and $Y^8$ each independently represent any one of the following groups:

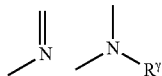

in which $R^\gamma$ represents a hydrogen atom or a protective group; $P^7$ represents a group of atoms necessary for forming a five-membered aromatic heterocyclic ring together with $Y^7$ and the one carbon atom adjacent to $Y^7$; and $P^8$ represents a group of atoms necessary for forming a five-membered aromatic heterocyclic ring together with $Y^8$ and the one carbon atom adjacent to $Y^8$.

(11) A metal complex comprising a metal atom and a ligand, wherein the ligand is the compound according to any one of the above items (1) to (7) and (10), or the polymer according to the above item (8) or (9).

(12) The metal complex according to the above item (11), wherein the metal atom is any one of transition metal atoms belonging to Period 4 to Period 6 in the periodic table.

(13) The metal complex according to the above item (11) or (12), wherein the number of metal atoms contained in the metal complex is 1 or 2.

(14) A modified metal complex obtained by subjecting the metal complex according to any one of the above items (11) to (13) to any modification treatment selected from a heating treatment, a radiation irradiation treatment and a discharge treatment, until a mass reduction rate after the treatment becomes 1 mass % or more and 90 mass % or less and a carbon content of the complex after the modification treatment becomes 5 mass % or more.

(15) A modified metal complex obtained by
preparing a mixture which comprises the metal complex according to any one of the above items (11) to (13), and any one selected from (A) to (C):
(A) a carbon carrier,
(B) an organic compound having a boiling point or melting point of 200° C. or higher, and
(C) an organic compound having a thermal polymerization initiation temperature of 250° C. or lower; and
subjecting the mixture to any modification treatment selected from a heating treatment, a radiation irradiation treatment and a discharge treatment, until a mass reduction rate after the modification treatment becomes 1 mass % or more and 90 mass % or less and a carbon content of the complex after the modification treatment becomes 5 mass % or more.

(16) The modified metal complex according to the above item (14) or (15), wherein the heating treatment is performed at 200° C. or higher and 1,200° C. or lower.

(17) A composition comprising the metal complex according to any one of the above items (11) to (13) or the modified metal complex according to any one of the above items (14) to (16), and a carbon carrier and/or a polymer.

(18) A catalyst comprising the metal complex according to any one of the above items (11) to (13), the modified metal complex according to any one of the above items (14) to (16), or the composition according to the above item (17).

(19) An electrode catalyst for fuel cell, comprising the catalyst according to the above item (18).

(20) A compound represented by formula (4):

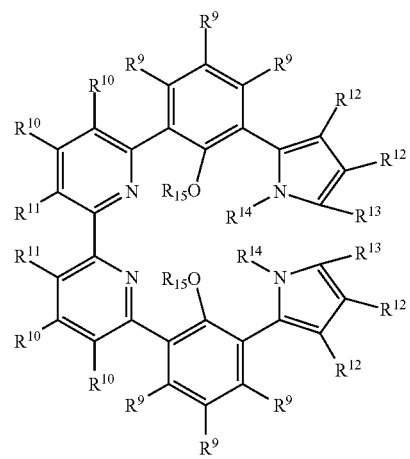

wherein, in formula (4), $R^9$ to $R^{13}$ each independently represent a hydrogen atom or a substituent, two adjacent $R^{10}$s, two adjacent $R^{11}$s, and two adjacent $R^{12}$s each may combine with each other to form a ring, $R^{14}$ and $R^{15}$ each independently represent a hydrogen atom or a protective group, and plural $R^9$s to $R^{15}$s may be the same or different from one another.

Other and further features and advantages of the invention will appear more fully from the following description.

BEST MODE FOR CARRYING OUT THE INVENTION

First, the compound represented by the above formula (1) of the present invention (hereinafter referred to as "macrocyclic compound") will be explained.

In formula (1), $Y^1$ to $Y^4$ each independently represent any one of the following groups.

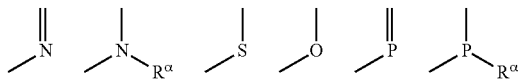

In the above groups, $R^\alpha$ represents a hydrogen atom or a monovalent hydrocarbon group (which preferably has 1 to 8 carbon atoms).

The monovalent hydrocarbon group represented by $R^\alpha$ is the same as any one of the following exemplary substituents. $P^1$ to $P^4$ each independently represent a group of atoms necessary for forming a heterocyclic ring together with each of $Y^1$ to $Y^4$ and the two carbon atoms adjacent to each of $Y^1$ to $Y^4$, respectively (which may hereinafter be referred to as "$P^1$ to $P^4$ structures"). It should be noted that the two carbon atoms at adjacent positions do not include carbon atoms that can be included in $R^\alpha$. Specific examples of the heterocyclic ring include pyrrolidine, piperidine, morpholine, piperazine, tetrahydrofuran, phosphole, phosphabenzene, pyridine, pyrazine, pyrimidine, pyrrole, N-alkylpyrrole, furan, thiophene, thiazole, imidazole, oxazole, benzimidazole, benzofuran, benzothiophene, isoquinoline, and quinazoline; preferably pyridine, pyrazine, pyrimidine, pyridazine, pyrrole, furan, thiophene, and N-alkylpyrrole; and more preferably pyridine, pyrrole, furan, and thiophene.

$Q^1$ and $Q^2$ each independently represent a connecting group or a direct binding. The connecting group is a divalent or trivalent group. The direct binding represents a single bond or a double bond. When $Q^1$ and $Q^2$ each represent a connecting group, the connecting group is preferably a group represented by any one of the following (1-a) to (1-g), more preferably a group represented by any one of (1-a) to (1-d), and especially preferably a group represented by (1-a) or (1-b). When $Q^1$ and $Q^2$ each represent a direct binding, the direct binding is preferably a single bond.

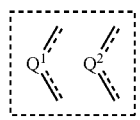

 (1-a)

 (1-b)

 (1-c)

 (1-d)

 (1-e)

 (1-f)

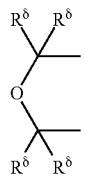 (1-g)

In the group represented by (1-a) to (1-g), $R^\delta$ represents a hydrogen atom or a monovalent group (for example, a monovalent hydrocarbon group which may be substituted and a monovalent aromatic group which may be substituted), and when plural $R^\delta$s are present, these plural $R^\delta$s may be the same or different from one another.

$P^1$ and $P^2$, $P^2$ and $P^6$, $P^6$ and $P^4$, $P^4$ and $P^3$, $P^3$ and $P^5$, and $P^5$ and $P^1$ may combine with each other to form a ring, respectively. Specifically, a ring formed by $P^1$ and $P^2$, or $P^4$ and $P^3$ as an example is preferably a structure represented by any one of (2-a) to (2-o), more preferably a structure represented by any one of (2-a), (2-j) to (2-o), and especially preferably a structure represented by any one of (2-a), (2-j) to (2-m). The monovalent hydrocarbon group or aromatic group represented by $R^\delta$ is the same as any one of the following exemplary substituents.

The following structures shown for typical examples may have a substituent(s). The substituent is the same as any one of the following shown substituents.

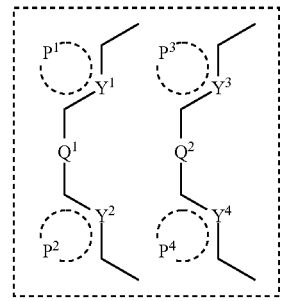

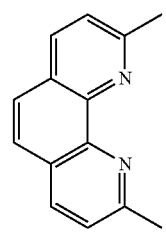 (2-a)

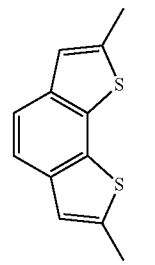 (2-b)

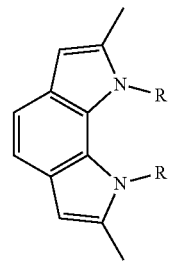 (2-c)

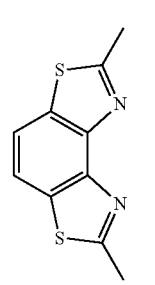 (2-d)

(2-e)
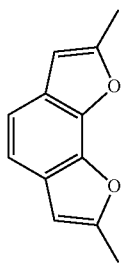

(2-f)
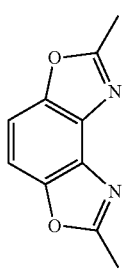

(2-g)
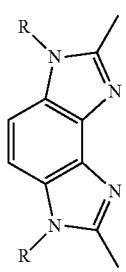

(2-h)
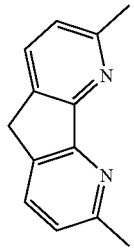

(2-i)
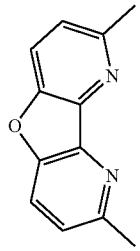

(2-j)
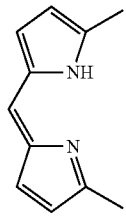

(2-k)

(2-l)

(2-m)

(2-n)

(2-o)

In the above groups, R represents a hydrogen atom or a monovalent hydrocarbon group having 1 to 30 carbon atoms (preferably 1 to 8 carbon atoms). Two Rs may be the same or different from each other.

Each of the $P^1$ and $P^2$ structures may have a substituent. Specific examples of the substituent include: a halogeno group such as a fluoro group, a chloro group, a bromo group, and an iodo group; a hydroxyl group; a carboxyl group; a mercapto group; a sulfonic acid group; a nitro group; a phosphonic acid group; a silyl group having an alkyl group or alkyl groups with 1 to 4 carbon atoms; a linear, branched, or cyclic saturated hydrocarbon groups each having a total carbon atoms of 1 to about 50, such as a methyl group, an ethyl group, a propyl group, an isopropyl group, a cyclopropyl group, a butyl group, an isobutyl group, a tert-butyl group, a pentyl group, a cyclopentyl group, a hexyl group, a cyclohexyl group, a norbornyl group, a nonyl group, a cyclononyl group, a decyl group, a 3,7-dimethyloctyl group, an adamantyl group, a dodecyl group, a cyclododecyl group, a pentadecyl group, an octadecyl group, and a docosyl group; a linear, branched, or cyclic alkoxy groups each having a total carbon atoms of 1 to about 50 such as a methoxy group, an ethoxy group, a propioxy group, a butoxy group, a pentyloxy group, a cyclohexyloxy group, a norbonyloxy group, a decyloxy group, and a dodecyloxy group; and monovalent aromatic groups each having a total carbon atoms of 6 to about 60 such as a phenyl group, a 4-bromophenyl group, a 2,6-dimethylphenyl group, a 4-biphenyl group, a 2-methylphenyl group, a 3-ethynylphenyl group, a pentafluorophenyl group, a 4-trifluoromethylphenyl group, a 3,5-dibromophenyl group, a 3,5-dimethoxyphenyl group, a 3,5-dihydroxyphenyl group, a 4-tert-butyl-2,6-methoxymethylphenyl group, a 4-tert-butylphenyl group, a 4-octylphenyl group, a 4-dodecylphenyl group, a 4-methylphenyl group, a 1-naphthyl group, a 2-naphthyl group, and a 9-anthryl group.

Among these, preferred ones are a halogeno group such as a fluoro group, a chloro group, a bromo group, or an iodo group; a mercapto group; a hydroxyl group; a carboxyl group; a monovalent hydrocarbon group having a total carbon atoms of 1 to about 20 including exemplified by a methyl group, an ethyl group, a propyl group, an isopropyl group, a butyl group, a pentyl group, a tert-butyl group, a cyclohexyl group, a norbornyl group, or an adamantyl group; a linear or branched alkoxy group having a total carbon atoms of 1 to about 10 including exemplified by a methoxy group, an ethoxy group, a propioxy group, a butoxy group, or a pentyloxy group; a monovalent aromatic group having a total carbon atoms of 6 to about 30 such as a phenyl group, a 4-bromophenyl group, a 2,6-dimethylphenyl group, a 4-biphenyl group, a 2-methylphenyl group, a 3-ethenylphenyl group, a pentafluorophenyl group, a 4-trifluoromethylphenyl group, a 3,5-dibromophenyl group, a 3,5-dimethoxyphenyl group, a 3,5-dihydroxyphenyl group, a 4-tert-butyl-2,6-methoxymethylphenyl group, a 4-tert-butylphenyl group, a 4-octylphenyl group, a 4-dodecylphenyl group, a 1-naphthyl group, a 2-naphthyl group, and a 9-anthryl group.

More preferred are a chloro group, a bromo group, a hydroxyl group, a carboxyl group, a methyl group, an ethyl group, a tert-butyl group, a cyclohexyl group, a norbornyl group, an adamantyl group, a methoxy group, an ethoxy group, a phenyl group, a 4-bromophenyl group, a 2,6-dimethylphenyl group, a 4-biphenyl group, a 2-methylphenyl group, a 3-ethynylphenyl group, a pentafluorophenyl group, a 4-trifluorophenyl group, a 3,5-dibromophenyl group, a 3,5-dimethoxyphenyl group, a 3,5-dihydroxyphenyl group, a 4-tert-butyl-2,6-methoxymethylphenyl group, a 4-tert-butylphenyl group, a 4-octylphenyl group, a 4-dodecylphenyl group, a 2-naphthyl group, and a 9-anthryl group.

$P^5$ and $P^6$ each independently represent a group of atoms necessary for forming a cyclic skeleton together with the carbon atom to which $Z^1$ bonds or $Z^2$ bonds and the two carbon atoms adjacent to the carbon atom to which $Z^1$ bonds or $Z^2$ bonds (which may hereinafter be referred to as "$P^5$ and $P^6$ structures"). $Z^1$ and $Z^2$ each independently represent any one of the following groups.

—$NR^\beta_2$, —$OR^\beta$, —$SR^\beta$, —$PR^\beta_2$

In the above groups, $R^\beta$ represents a hydrogen atom or a monovalent hydrocarbon group (which preferably has 1 to 8 carbon atoms, and more preferably has 1 to 6 carbon atoms).

The monovalent hydrocarbon group represented by $R^\beta$ is the same as any one of the above exemplary substituents. The structures of $P^5$ and $Z^1$, and $P^6$ and $Z^2$ as an example are preferably a structure represented by any one of (3-a) to (3-o), more preferably a structure represented by any one of (3-a) to (3-h), further more preferably a structure represented by any one of (3-a) to (3-d), and especially preferably a structure represented by (3-a) or (3-b).

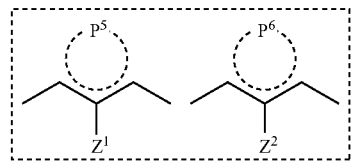

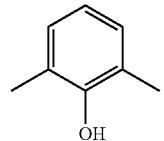
(3-a)

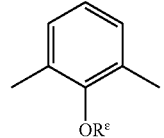
(3-b)

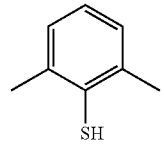
(3-c)

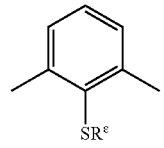
(3-d)

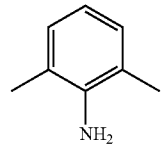
(3-e)

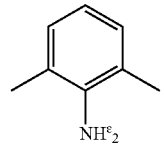
(3-f)

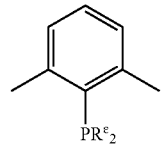
(3-g)

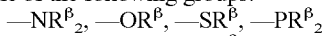
(3-h)

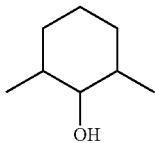
(3-i)

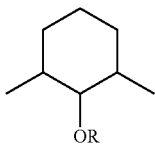
(3-j)

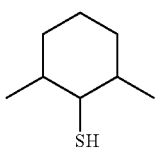
(3-k)

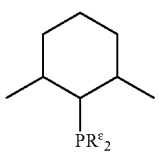
(3-l)

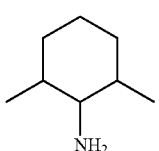
(3-m)

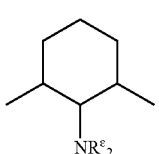
(3-n)

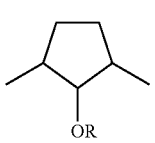
(3-o)

In the above (3-a) to (3-o), $R^\epsilon$ represents a hydrocarbon group having 1 to 10 carbon atoms. When plural $R^\epsilon$s are present, these plural $R^\epsilon$s may be the same or different from each other.

Each of $P^5$ and $P^6$ structures may have a substituent, and examples of such substituent include the above exemplary substituents. The monovalent hydrocarbon group represented by $R^\epsilon$ is the same as any one of the above exemplary substituents.

Next, the compound represented by the above formula (2) of the present invention will be explained.

$R^1$ represents a hydrogen atom or a substituent. Plural $R^1$s may be the same or different from one another. Examples of such substituent include substituents equivalent to above exemplary substituents.

$Q^3$ and $Q^4$ each independently represent any one of the following groups.

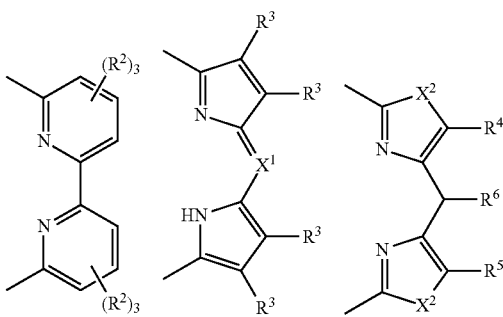

In the above groups, $R^2$, $R^3$, $R^4$ and $R^5$ each independently represent a hydrogen atom or a substituent. The substituent is the same as any one of the above shown substituents.

$R^2$s may combine with each other to form a ring. $R^3$s may combine with each other to form a ring. $R^4$, $R^5$ and $R^6$ each independently represent a hydrogen atom or a substituent. $R^4$ and $R^6$, $R^5$ and $R^6$, and/or $R^4$, $R^5$ and $R^6$ may combine with each other to form a ring. $X^1$ represents a nitrogen atom or a trivalent group. $X^2$ represents any one of the following groups.

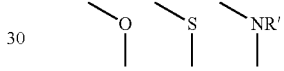

In the above groups, R' represents a hydrogen atom or a monovalent hydrocarbon group.

$Q^3$ and $Q^4$ are preferably a bivalent group represented by any one of the following structures (4-a) to (4-j), more preferably a bivalent group represented by any one of (4-a), (4-b), (4-d), (4-e) and (4-g) to (4-j), further more preferably a bivalent group represented by any one of (4-a), (4-b), (4-d), (4-e), (4-h) and (4-j), especially preferably a bivalent group represented by any one of (4-a), (4-b), (4-d) and (4-e). The following structures shown for typical examples may have a substituent(s). The substituent is the same as any one of the above shown substituents.

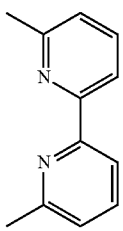
(4-a)

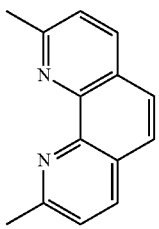
(4-b)

(4-c)
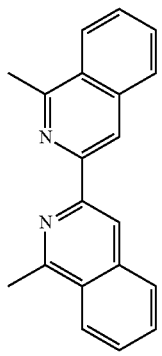

(4-d)
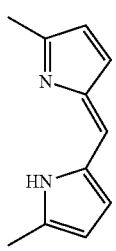

(4-e)
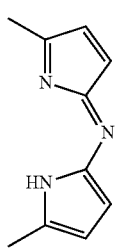

(4-f)
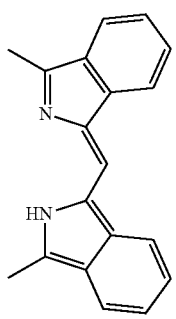

(4-g)
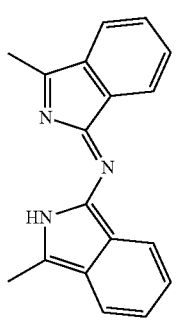

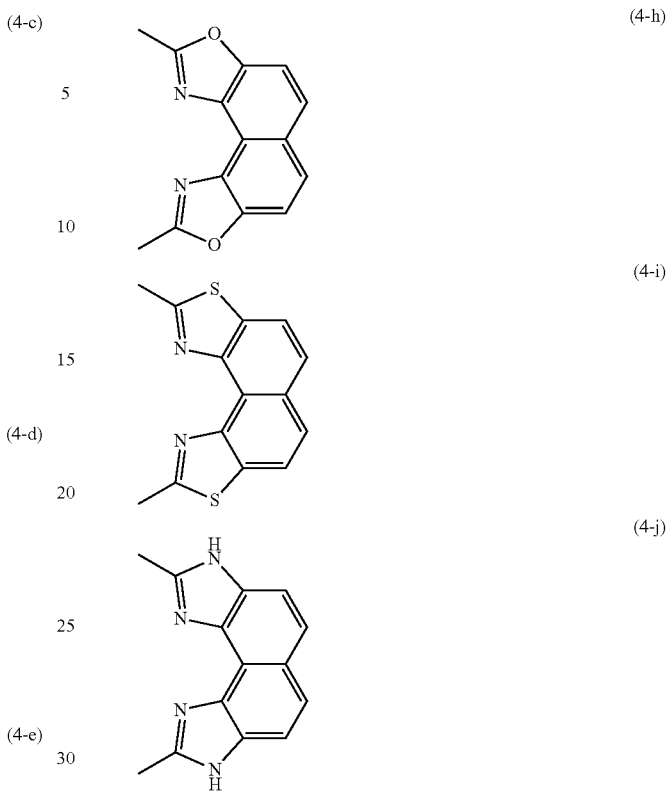

(4-h)

(4-i)

(4-j)

The macrocyclic compound represented by the above formula (1) is preferably the compound represented by the following formula (5).

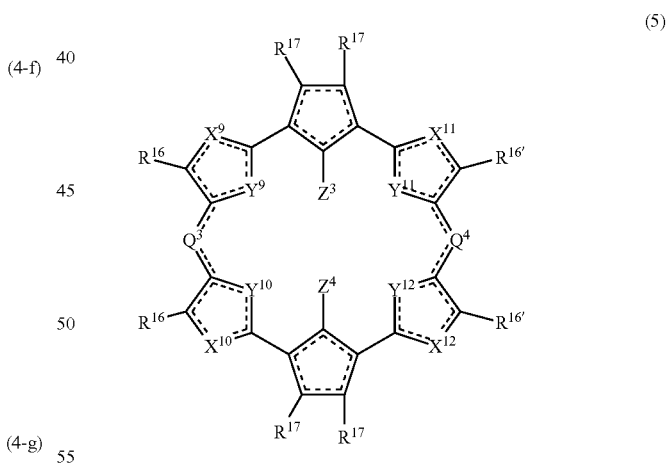

(5)

In formula (5), $R^{16}$, $R^{16'}$ and $R^{17}$ each independently represent a hydrogen atom or a substituent. Plural $R^{16}$s, $R^{16'}$s and $R^{17}$s may be the same or different from one another, respectively. $R^{16}$s may combine with $Q^3$ to form a ring (preferably a five- and/or six-membered ring), and $R^{16'}$s may combine with $Q^4$ to form a ring (preferably a five- and/or six-membered ring). $Y^9$ to $Y^{12}$ each independently represent a bivalent group represented by any one of the following groups.

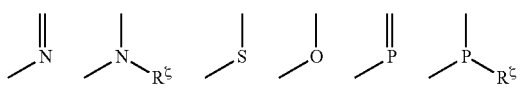

In the above groups, $R^\zeta$ represents a hydrogen atom or a monovalent hydrocarbon group. The monovalent hydrocarbon group represented by $R^\zeta$ is the same as any one of the above exemplary substituents. $X^9$ to $X^{12}$ each independently represent a divalent group (especially a divalent group composed of a combination of atoms selected from a group consisting of nitrogen, oxygen, sulfur, hydrogen and carbon). $X^9$ to $X^{12}$ each independently may form a ring by combining with $R^{16}$ or $R^{16'}$ at the position nearest to one another (namely, when illustrated by a structural formula, the position at which the number of atoms present between $X^9$ to $X^{12}$ and $R^{16}$ or $R^{16'}$ is minimized). $n^1$ and $n^2$ each independently represent an integer 1 or 2. $Q^3$ and $Q^4$ each independently represent a connecting group or a direct binding. $Z^3$ and $Z^4$ each independently represent any one of the following groups.

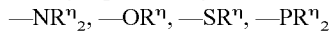

In the above groups, $R^\eta$ represents a hydrogen atom or a monovalent hydrocarbon group. In the formula, the portion that is connected in a dotted line may or may not be conjugated.

$X^9$ to $X^{12}$ each independently represent a bivalent group (especially a divalent group composed of a combination of atoms selected from a group consisting of nitrogen, oxygen, sulfur, hydrogen and carbon). $X^9$ to $X^{12}$ each correspondingly constitute a five-membered ring or a six-membered ring together with $Y^9$ to $Y^{12}$ and surrounding carbon atoms. Specific examples of the five-membered ring and a six-membered ring include pyrrolidine, piperidine, morpholine, piperazine, tetrahydrofuran, phosphole, phosphabenzene, pyridine, pyrazine, pyrimidine, pyrrole, N-alkylpyrrole, furan, thiophene, thiazole, imidazole, oxazole, benzofuran, benzothiophene, isoquinoline, and quinazoline; preferably pyridine, pyrazine, pyrimidine, pyrrole, furan, thiophene, and N-alkylpyrrole; and more preferably pyridine, pyrrole, furan, and thiophene.

The monovalent hydrocarbon group represented by $R^\eta$ is the same as any one of the above exemplary substituents. When plural $R^\eta$s are present, these plural $R^\eta$s may be the same or different from each other.

The macrocyclic compound of the present invention can be synthesized by the following steps: firstly obtaining a dibromo compound in the same manner as described in Tetrahedron., 1999, 55, 8377, then synthesizing a precursor by a cross-coupling reaction using the obtained dibromo compound together with a transition metal catalyst, and then conducting a ring closure reaction using aldehyde. Alternatively, the macrocyclic compound may be synthesized by adding aldehyde to a compound having a pyrrole at the end thereof (a precursor) to couple the pyrroles with each other.

In this synthesis, since plural precursors are reacted with one another so as to be connected with aldehyde, it is preferable to use a heterocyclic compound represented by the above formula (3) as the precursor.

The compound represented by the above formula (1) can be synthesized, for example, by reacting a compound represented by formula (3) and an aldehyde compound represented by formula (6) according to the following reaction scheme.

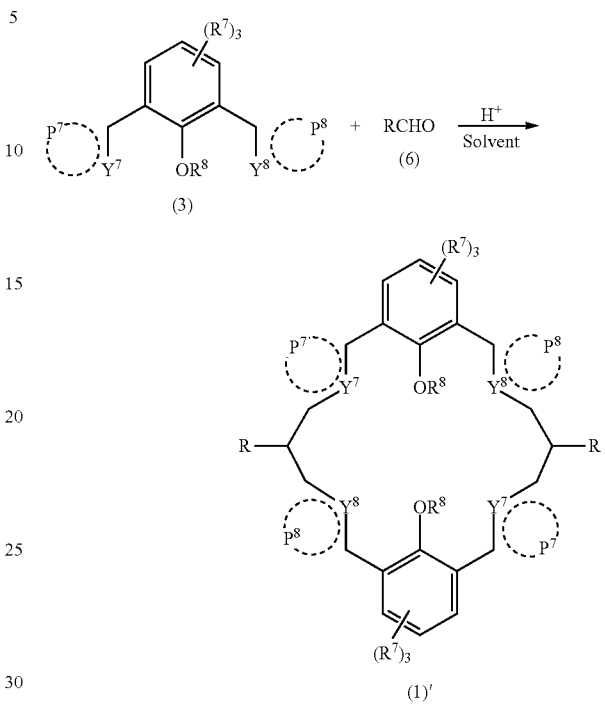

In the above formula, R represents a hydrogen atom or a monovalent group (for example, a monovalent hydrocarbon group which may be substituted and a monovalent aromatic group which may be substituted).

The above reaction may be conducted by dissolving raw materials in a suitable solvent and using an acid as a catalyst. Alternatively, the acid itself may be used as a solvent to conduct the above reaction.

Examples of the acid include boron trifluoride, boron trifluoride etherate, boron trichloride, boron tribromide, trifluoroacetic acid, trifluoromethane sulfonic acid, and p-toluene sulfonic acid. Examples of the acid that is used as a solvent include organic acids such as acetic acid, propionic acid, or butanoic acid as well as the acids shown above.

Examples of the solvent include dichloromethane, chloroform, carbon tetrachloride, methanol, ethanol, and a mixture thereof.

A reaction temperature is ordinarily in the range of 0° C. to 250° C., preferably from 0° C. to 200° C., and especially preferably from 0° C. to 160° C. A reaction time is ordinarily in the range of 1 minute to 1 week, preferably from 5 minutes to 100 hours, and especially preferably from 1 hour to 48 hours. Both reaction temperature and reaction time mentioned above may be adjusted by a combination of an acid and a solvent.

Further, a macrocyclic compound including an oxidized connecting portion can be synthesized by adding an oxidizing agent and a solvent to the compound obtained in the above reaction.

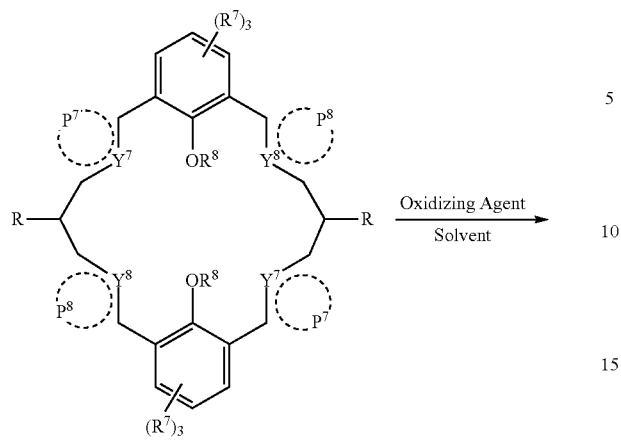

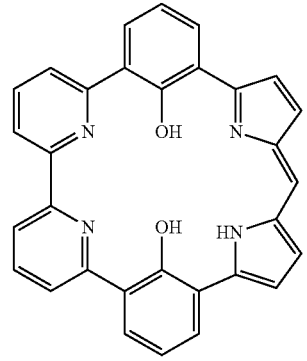

(IV-1)

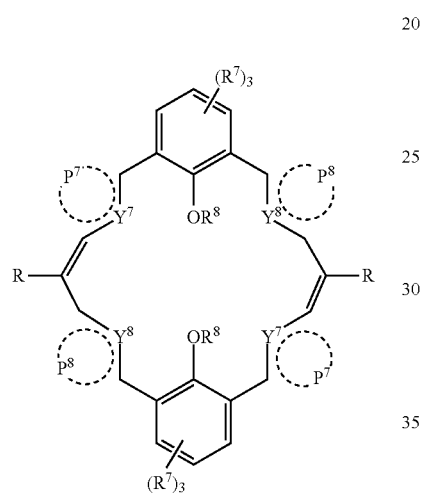

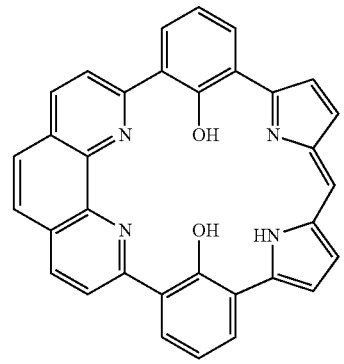

(IV-2)

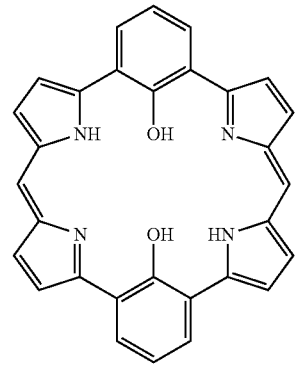

(IV-3)

Examples of the oxidizing agent include oxygen, chloranil, and 2,3-dichloro-5,6-dicyano-1,4-benzoquinone. Examples of the solvent include the same solvents as those exemplified above.

A reaction temperature is ordinarily in the range of 0° C. to 250° C., preferably from 0° C. to 200° C., and especially preferably from 0° C. to 160° C. A reaction time is ordinarily in the range of 1 minute to 1 week, preferably from 5 minutes to 100 hours, and especially preferably from 1 hour to 48 hours.

The macrocyclic compound represented by formula (2) is preferably the macrocyclic compound represented by the above formula (a1) or the macrocyclic compound represented by the above formula (a2).

The compound represented by the above formula (2) is preferably those compounds that are produced by a combination of structures described above. Specifically, compounds represented by the following formulae (IV-1) to (IV-6) are more preferable. Among these compounds, those represented by the formulae (IV-1) to (IV-4) are especially preferable. The following structures shown for typical examples may have a substituent(s). The substituent is the same as any one of the above shown substituents.

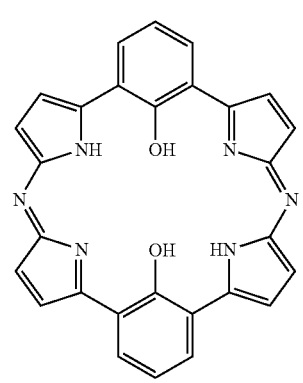

(IV-4)

(IV-5)

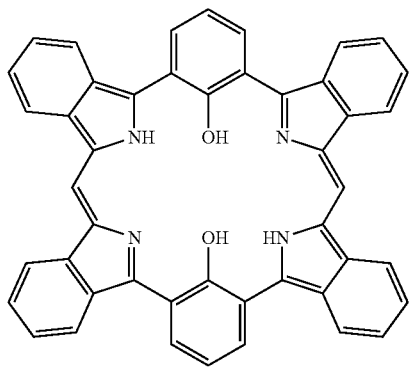

(IV-6)

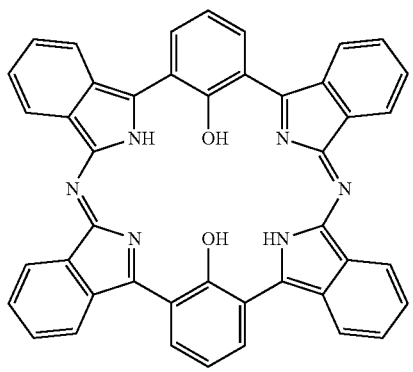

A polymer having a residue of the metal complex represented by the above formula (1) means to a polymer having a group comprising an atomic group obtained by removing a part or all of the hydrogen atoms (one hydrogen atom in ordinary cases) in the metal complex represented by the formula (1). The polymer to be used in this case is not particularly limited and examples of the polymer include a conductive polymer, a dendrimer, a natural polymer, a solid polymer electrolyte, polyethylene, polystyrene, polyacrylonitrile, polyethylene glycol, and polypropylene. Of those, the conductive polymer, the solid polymer electrolyte, polystyrene, and polyacrylonitrile are preferred, polystyrene and polyacrylonitrile are particularly preferred. The term "conductive polymer" is a collective term for polymer substances each showing metallic or semi-metallic conductivity (Iwanami Physical and Chemical Science Dictionary, fifth edition: issued in 1988). Examples of the conductive polymer include: polyacetylene and a derivative of polyacetylene, polyparaphenylene and a derivative of polyparaphenylene, polyparaphenylene vinylene and a derivative of polyparaphenylene vinylene, polyaniline and a derivative of polyaniline, polythiophene and a derivative of polythiophene, polypyrrole and a derivative of polypyrrole, polyfluorene and a derivative of polyfluorene, polyfluorene and a derivative of polyfluorene, polycarbazole and a derivative of polycarbazole, and polyindole and a derivative of polyindole described in "Conductive Polymer" (written by Shinichi Yoshimura, KYORITSU SHUPPAN CO., LTD) and "New Applications of Conducting Polymers" (edited by Yukio Kobayashi, CMC Publishing CO., LTD.); and copolymers of the conductive polymers.

Examples of the solid polymer electrolyte include polymers obtained by sulfonating perfluorosulfonic acid, polyether ether ketone, polyimide, polyphenylene, polyarylene, and polyarylene ether sulfone.

A polymer having the residue of the metal complex represented by formula (1) as a repeating unit means to a polymer having the group comprising an atomic group obtained by removing a part or all of the hydrogen atoms (two hydrogen atoms in ordinary cases) in the metal complex represented by formula (1) as a repeating unit, and the polymer is produced by, for example, polymerizing a bifunctional monomer containing a macrocyclic ligand.

The molecular weight of the polymer (length of molecular chain) is not particularly limited. However, the molecular weight is preferably at least 1000 and preferably 1,000,000 or less, more preferably 100,000 or less, and further preferably 50,000 or less.

Next, the compound represented by the above formula (3) is described.

The compound represented by the above formula (3) is a compound that constitutes a partial structure of the macrocyclic compound represented by the above formula (1) or (2). Further, the compound represented by the above formula (3) functions as a synthetic raw material of the macrocyclic compound represented by the above formula (1) or (2).

In the above formula (3), $R^8$ represents a hydrogen atom or a protective group.

$Y^7$ and $Y^8$ each independently represent any one of the following groups.

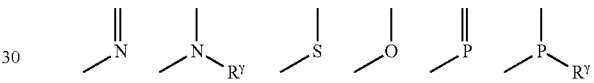

In the above groups, $R^Y$ represents a hydrogen atom or a monovalent hydrocarbon group (a monovalent hydrocarbon group preferably having 1 to 8 carbon atoms, more preferably having 1 to 6 carbon atoms).

$P^7$ and $P^8$ each independently represent a group of atoms necessary for forming a five-membered aromatic heterocyclic ring together with $Y^7$ or $Y^8$ and one carbon atom adjacent to $Y^7$ or $Y^8$. $P^7$ and $P^8$ each represent a group of atoms necessary for forming a cyclic skeleton. It should be noted that the one carbon atoms at adjacent positions do not include carbon atoms that can be included in $R^Y$. Specific examples of the heterocyclic ring include pyrrole, N-alkylpyrrole, imidazole, phosphole, thiophene, thiazole, furan, and oxazole; preferably pyrrole, N-alkylpyrrole, imidazole, thiophene, and thiazole; and more preferably pyrrole and N-alkylpyrrole.

$P^7$ and $P^8$ structures may have a substituent(s). The substituent is the same as any one of the above shown substituents.

Next, a metal complex including the above compound as a ligand is described. The metal atom forms a complex together with hetero atoms. When two metal atoms are present, the metal atoms may be coordinated with each other by bridge coordination. The term "transition metal" as used herein has the same meaning as that of a "transition element" described in p 1283 of "Chemistry Unabridged Dictionary" (edited by Michinori Ohki et al. and issued by Tokyo Kagaku Dojin on Jul. 1, 2005), and means to an element having an incomplete d or f subshell. It should be noted that the transition metal atom in the present invention may be uncharged, or may be a charged ion; the same holds true for the typical metal atom, and the typical metal atom may be uncharged, or may be a bridged ion.

Here, specific examples of the transition metal include scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, and mercury.

In addition, specific examples of the typical metal include aluminum, gallium, germanium, indium, tin, antimony, thallium, lead, and bismuth.

Among these metals, transition metals belonging to fourth-period elements, fifth-period elements and sixth-period elements are preferred from a practical point of view. Of them, titanium, vanadium, manganese, iron, cobalt, nickel, copper, zinc, molybdenum, ruthenium, rhodium, palladium, silver, tantalum, tungsten, rhenium, osmium, iridium, platinum, or gold is more preferable. Of them, titanium, vanadium, manganese, iron, cobalt, nickel, copper, zinc, molybdenum, rhodium, silver, or platinum is further preferable. Especially, metal elements belonging to the fourth-period, i.e., manganese, iron, cobalt, nickel, copper, or zinc is especially preferable.

The metal complex may include a neutral molecule, or a counter ion capable of electrically neutralizing the metal complex.

Examples of the neutral molecule include a molecule that solvates to form a solvated salt and a ligand except the cyclic ligand in each of the above formulae (1) and (2). Specific examples of the neutral molecule include water, methanol, ethanol, n-propanol, isopropyl alcohol, 2-methoxyethanol, 1,1-dimethylethanol, ethylene glycol, N,N'-dimethylformamide, N,N'-dimethylacetamide, N-methyl-2-pyrrolidone, dimethyl sulfoxide, acetone, chloroform, acetonitrile, benzonitrile, triethyl amine, pyridine, pyrazine, diazabicyclo[2,2,2]octane, 4,4'-bipyridine, tetrahydrofuran, diethyl ether, dimethoxyethane, methyl ethyl ether, 1,4-dioxane, acetic acid, propionic acid, and 2-ethylhexanoic acid; and preferably water, methanol, ethanol, isopropyl alcohol, ethylene glycol, N,N'-dimethylformamide, N,N'-dimethylacetamide, N-methyl-2-pyrrolidone, chloroform, acetonitrile, benzonitrile, triethyl amine, pyridine, pyrazine, diazabicyclo[2,2,2]octane, 4,4'-bipyridine, tetrahydrofuran, dimethoxyethane, 1,4-dioxane, acetic acid, propionic acid, and 2-ethylhexanoic acid.

As the counter ion, because the transition metal atom and typical metal atom generally have a positive charge, a negative ion which neutralizes the atom electrically is selected. Examples of the counter ion include a fluorine ion, a chlorine ion, a bromine ion, an iodine ion, a sulfide ion, an oxide ion, a hydroxide ion, a hydride ion, a sulfite ion, a phosphate ion, a cyanide ion, an acetate ion, a 2-ethylhexanoate ion, a carbonate ion, a sulfate ion, a nitrate ion, a hydrogen carbonate ion, a trifluoroacetate ion, a thiocyanide ion, a trifluoromethane sulfonate ion, an acetylacetonate, a tetrafuloroborate ion, a hexafluorophosphate ion, and a tetraphenylborate ion, and preferably a chloride ion, a bromide ion, an iodide ion, an oxide ion, a hydroxide ion, a hydride ion, a phosphate ion, a cyanide ion, an acetate ion, a 2-ethylhexanoate ion, a carbonate ion, a sulfate ion, a nitrate ion, an acetylacetonate, and a tetraphenylborate ion.

In addition, when a plurality of X's are present, the X's may be the same as or different from each other, or a neutral molecule and an ion may be coexistent with each other.

Next, a method of synthesizing the metal complex of the present invention will be explained.

The metal complex of the present invention can be obtained by: synthesizing the ligand organo-chemically; and mixing the ligand and a reaction agent that provides the metal atom (hereinafter referred to as "metal-providing agent").

As described above, the metal complex of the present invention can be obtained by mixing the ligand and the metal-providing agent in the presence of a appropriate reaction solvent. Specific examples of the reaction solvent include water, acetic acid, oxalic acid, ammonia water, methanol, ethanol, n-propanol, isopropyl alcohol, 2-methoxyethanol, 1-butanol, 1,1-dimethylethanol, ethylene glycol, diethyl ether, 1,2-dimethoxyethane, methyl ethyl ether, 1,4-dioxane, tetrahydrofuran, benzene, toluene, xylene, mesitylene, durene, decalin, dichloromethane, chloroform, carbon tetrachloride, chlorobenzene, 1,2-dichlorobenzene, N,N'-dimethylformamide, N,N'-dimethylacetamide, N-methyl-2-pyrrolidone, dimethyl sulfoxide, acetone, acetonitrile, benzonitrile, triethylamine, pyridine, pyrazine, and diazabicyclo[2,2,2]octane. A reaction solvent obtained by mixing two or more kinds of them may be used and a solvent which can dissolve a ligand and a metal-providing agent is preferred. The reaction can be performed at a temperature of generally −10 to 200° C., preferably 0 to 150° C., or particularly preferably 0 to 100° C. for a time period of generally 1 minute to 1 week, preferably 5 minutes to 24 hours, or particularly preferably 1 hour to 12 hours. It should be noted that the reaction temperature and the reaction time can also be appropriately optimized depending on the kinds of the ligand and the metal-providing agent.

As a method involving isolating the produced metal complex from the reaction solution after the reaction and purifying the metal complex, an optimum method selected from a known recrystallization method, a known redeposit method, and a known chromatography method can be appropriately employed, and two or more of these methods may be employed in combination.

The produced metal complex may precipitate depending on the kind of the reaction solvent. The precipitated metal complex can be isolated and purified by separating the metal complex by a separation method such as filtration and subjecting the separated product to a washing operation and a drying operation as required.

Since the basic structures of the metal complexes having the compound represented by the above formula (1) as a ligand are each aromatic, each of the complexes has high heat resistance and high acid resistance, and hence maintains its complex structure stably even at high temperatures or even in the presence of a strong acid. Accordingly, each of the complexes is expected to exert a catalytic action.

The metal complexes are particularly suitable for use as, for example, redox catalysts, and specific examples of the applications of the metal complexes include: decomposition catalysts for hydrogen peroxide; oxidation polymerization catalysts for aromatic compounds; catalysts for purifying an exhaust gas and waste water; redox catalyst layers for dye sensitization solar cells; carbon dioxide reduction catalysts; catalysts for the production of reformed hydrogen; and oxygen sensors. In addition, the metal complexes can be used as organic semiconductor materials such as organic EL materials, organic transistors, and dye sensitization solar cells by taking advantage of the fact that each of the metal complexes has an expanded conjugation.

In particular, the macrocyclic compound can be obtained efficiently by a reaction between the compound represented by the above formula (3) or (4) and aldehyde.

Next, the compound represented by formula (4) is described.

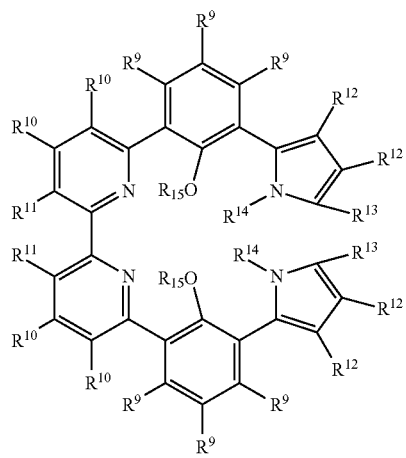

(4)

In formula (4), $R^9$ to $R^{13}$ each independently represent a hydrogen atom or a substituent. Two adjacent $R^{10}$s, two adjacent $R^{11}$s, and two adjacent $R^{12}$s may combine with each other to form a ring, respectively. $R^{14}$ and $R^{15}$ each independently represent a hydrogen atom or a protective group. Plural $R^9$s to $R^{15}$s may be the same or different from one another.

The substituent represented by any one of $R^9$ to $R^{13}$ is the same as any one of the above exemplary substituents.

$R^{14}$ and $R^{15}$ each independently represent a hydrogen atom or a protective group. Specific examples of the protective group include a methyl group, an isopropyl group, a cyclohexyl group, a tert-butyl group, a benzyl group, a methoxymethyl group, a benzyloxymethyl group, a methoxyethoxymethyl group, a trimethylsilylethoxymethyl group, a trimethylsilyl group, a tert-butyldimethylsilyl group, a triisopropylsilyl group, a methylcarbonyl group, a phenylcarbonyl group, and a tert-butoxycarbonyl group. Preferred protective group include a methyl group, a benzyl group, a methoxymethyl group, a trimethylsilylethoxymethyl group, a trimethylsilyl group, a tert-butyldimethylsilyl group, and a tert-butoxycarbonyl group; and further preferred protective group include a methyl group, a benzyl group, a methoxymethyl group, and a tert-butoxycarbonyl group.

Preferable examples of the compound represented by the above formula (4) include compounds represented by the following formulae (V-1) to (V-8). Further, the above-described substituent may combine to an aromatic ring of these compounds.

In formulae (V-1) to (V-8), MOM represents a methoxymethyl group, Boc represents a tert-butoxycarbonyl group, and Me represents a methyl group.

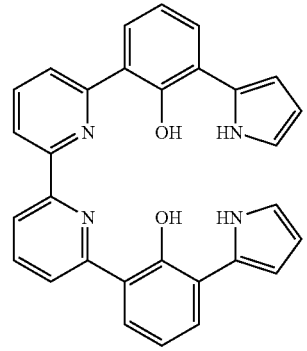

(V-1)

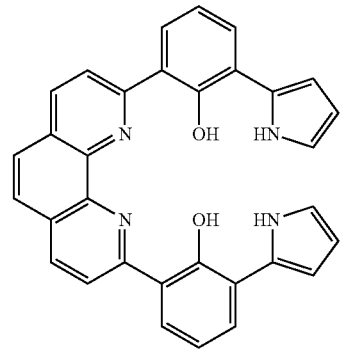

(V-2)

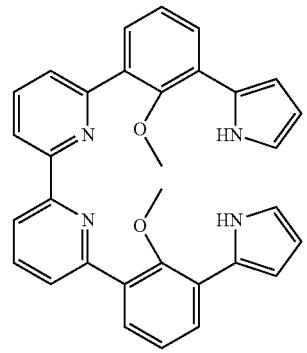

(V-3)

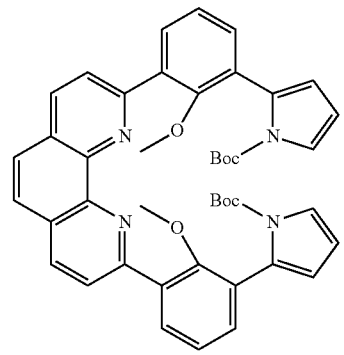

(V-4)

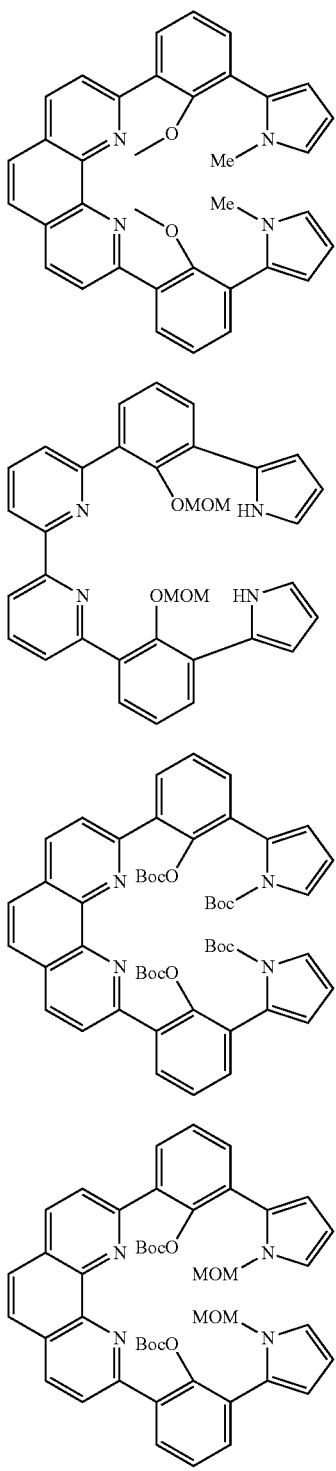

(V-5)

(V-6)

(V-7)

(V-8)

Next, conditions for modification treatment for the metal complex of the present invention are described in detail.

The metal complex to be used for the modification treatment may be one metal complex or two or more metal complexes.

As pretreatment for the modification treatment, the metal complex is particularly preferable to be dried at a temperature of 15° C. or higher and 200° C. or lower under reduced pressure of 1333 Pa or lower for 6 hours or longer. The pretreatment may be carried out using a vacuum drier or the like.

The treatment of the metal complex is preferably carried out in the presence of hydrogen, helium, nitrogen, ammonia, oxygen, neon, argon, krypton, xenon, acetonitrile, or a gas mixture of these gases.

It is preferably in the presence of hydrogen, helium, nitrogen, ammonia, oxygen, neon, argon, or a gas mixture of these gases; and more preferably in the presence of hydrogen, nitrogen, ammonia, argon, or a gas mixture of these gases.

In addition, the pressure in the modification treatment can be appropriately changed depending on the modification treatment to be selected.

First, the heating treatment will be explained.

The temperature at which the metal complex is subjected to a heating treatment is not particularly limited as long as the mass reduction rate after the heating treatment becomes 1 mass % or more and 90 mass % or less.

The temperature for the heating treatment is preferably 200° C. or higher, and more preferably 300° C. or higher. In addition, an upper limit of the temperature for heating treatment is not particularly limited as long as the carbon content of the modified product after the treatment (the carbon content means a content rate of carbon atoms which can be determined, for example, by elemental analysis) is 5 mass % or more; the temperature is preferably 1,200° C. or lower, more preferably 1,000° C. or lower, and further preferably 800° C. or lower.

The treatment time for the heating treatment may be set properly depending on the above-mentioned gas to be used, temperature and the like. Alternatively, the temperature may be gradually increased from room temperature to an aimed temperature and then decreased immediately in the state that the above-mentioned gas is tightly closed or ventilated. Particularly, it is preferable to keep the temperature after the temperature reaches the aimed temperature since the metal complex can be gradually heated and the durability can be improved more. The time period for which the temperature is held at the aimed temperature after the arrival is not particularly limited as long as the time period is preferably 1 to 100 hours, more preferably 1 to 40 hours, still more preferably 2 hours to 10 hours, or particularly preferably 2 to 3 hours.

As apparatus for the heating treatment, an oven, a furnace, an IH hot plate, and the like can be exemplified.

Examples of the modification treatments for substituting the heating treatment can be selected from methods of any radiation irradiation treatment selected from electromagnetic waves or particle beams such as α-ray, β-ray, neutron beam, electron beam, γ-ray, X-ray, vacuum ultraviolet ray, ultraviolet ray, visible ray, infrared ray, microwave, electric wave, laser and the like; and electric discharge treatment such as corona discharge treatment, glow discharge treatment, plasma treatment (including low temperature plasma treatment).

Preferable modification treatment among them may be the radiation irradiation treatment selected from X-ray, electron beam, ultraviolet ray, visible ray, infrared ray, microwave, and laser; and low temperature plasma treatment. More preferable treatment may be the radiation irradiation treatment selected from ultraviolet ray, visible ray, infrared ray, microwave, and laser.

These treatments may be carried out according to instruments and treatment methods to be used generally for surface reforming treatment of polymer films and for example, methods described in a literature (Adhesion Society of Japan, "Chemistry of Surface Analysis, Reformation", issued by Nikkan Kogyo Shimbun on Dec. 19, 2003), etc. can be employed.

At the time of carrying out the above-mentioned radiation irradiation treatment or discharge treatment, the conditions may be arbitrarily set to adjust the mass reduction rate of the metal complex by the treatment in a range of 1 mass % or more to 90 mass % or less and the carbon content of the modified product after the treatment of 5 mass % or more. Preferable treatment time is within 10 hours, more preferably within 3 hours, furthermore preferably within 1 hour, and particularly preferably within 30 minutes.

As described above, any modification treatment of the heating treatment, radiation irradiation treatment, and discharge treatment is carried out to an extent that the mass reduction rate becomes 1 mass % or more to 90 mass % or less, preferably 2 mass % or more to 90 mass % or less, to obtain the modified metal complex of the present invention.

In the present invention, the upper limit of the mass reduction rate is preferably 80 mass % or less, more preferably 70 mass % or less, and particularly preferably 60 mass % or less, since too much mass reduction at the time of heating treatment, radiation irradiation treatment, or discharge treatment may cause the significant decomposition of the complex structure.

Further, the modified metal complex of the present invention has a carbon content of 5 mass % or more by elemental analysis. The carbon content is preferably 10 mass % or more, more preferably 20 mass % or more, furthermore preferably 30 mass % or more, and particularly preferably 40 mass % or more. The carbon content of the treated product is preferably as high as possible because the complex structure additionally stabilizes and the degree of assemblage of the metal atom in the modified metal complex easily increases.

Next, another embodiment of the modified metal complex of the present invention will be explained.

The modified metal complex of the present invention is a modified metal complex showing a mass reduction rate by the treatment of 1 to 90 mass % and a carbon content after the modification treatment of 5 mass % or more in the case of subjecting a metal complex mixture of (a) a metal complex and (b) a carbon carrier, an organic compound having a boiling point or melting point of 200° C. or more, or an organic compound having a thermal polymerization initiating temperature of 250° C. or less to any of heating treatment, radiation irradiation treatment, and discharge treatment. Herein, the mass reduction rate is on the basis of the total mass of (a) and (b) in the metal complex mixture.

In the metal complex mixture, the ratio of (a) and (b) to be mixed is preferably designed such that the content of (a) is 1 to 70 mass % based on the total mass of (a) and (b). The content of the base metal complex is preferably 2 to 60 mass % and particularly preferably 3 to 50 mass %.

Examples of the carbon carrier include carbon particles such as Norit (trade name, manufactured by Norit Corporate Co.), Ketjen black (trade name, manufactured by Lion Corporation), Vulcan (trade name, manufactured by Cabot Corporation), black pearl (trade name, manufactured by Cabot Corporation), acetylene black (trade name, manufactured by Chevron Corporation); fullerene such as C60 and C70; carbon nanotubes, carbon nanohorns, carbon fibers and the like.

Examples of the organic compound having a boiling point or melting point of 200° C. or more are aromatic carboxylic acid derivatives such as perylene-3,4,9,10-tetracarboxylic dianhydride, 3,4,9,10-perylenetetracarboxylic acid diimide, 1,4,5,8-naphthalenetetracarboxylic dianhydride, 1,4,5,8-naphthalenetetracarboxylic acid diimide, 1,4,5,8-naphthalenetetracarboxylic acid, pyromellitic acid, and pyromellitic dianhydride. The structures of these compounds are shown below. Herein, the boiling point or melting point can be measured by a conventionally known method and it may be selected from the measured values and also may be selected from the values disclosed in literatures or the like. It may also be a calculated value obtained by a computation simulation or the like and it may be, for example, selected from the calculated value of the boiling point or melting point registered in SciFinder, which is a computer software program provided by Chemical Abstract Service (version 2007, 2). In the following compounds, the remark "calc" in the boiling point (b.p.) is a calculated value registered in the above-mentioned SciFinder.

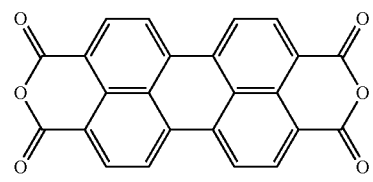

b.p.: 755 C.° (calc)
m.p.: >300° C.

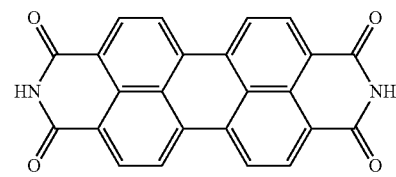

b.p.: 787 C.° (calc)

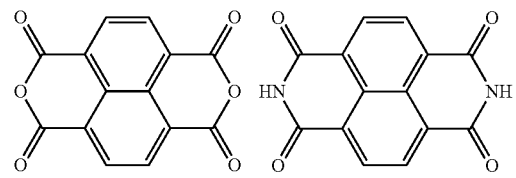

b.p.: 617 C.° (calc)    b.p.: 656 C.° (calc)
m.p.: 450 C.°           m.p.: >410 C.°

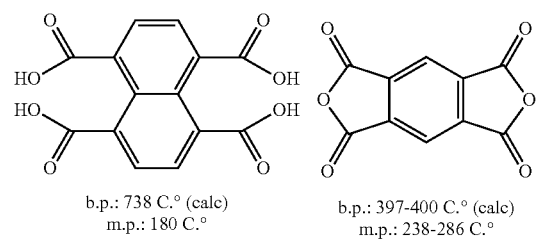

b.p.: 738 C.° (calc)    b.p.: 397-400 C.° (calc)
m.p.: 180 C.°           m.p.: 238-286 C.°

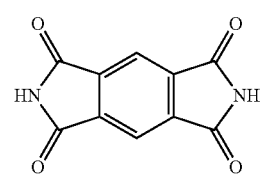

m.p.: 440 C.°

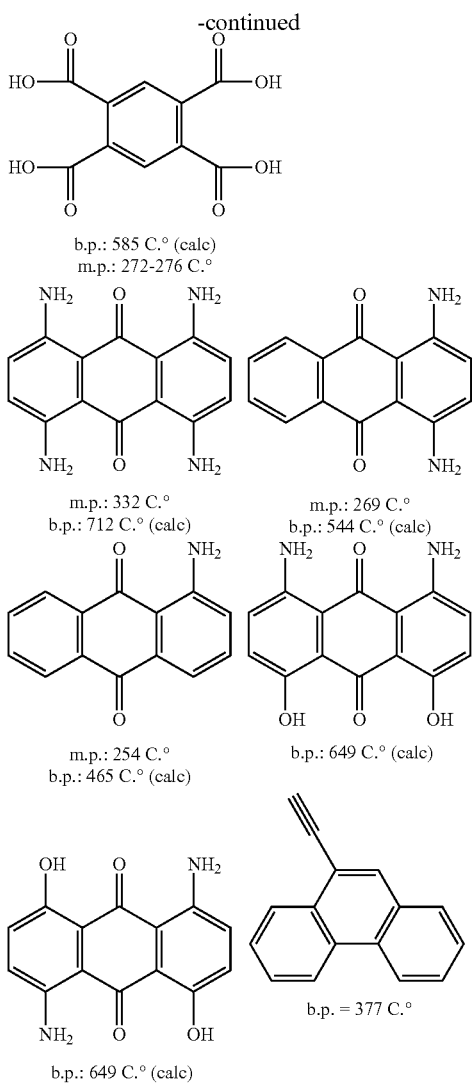

The organic compound having a thermal polymerization initiation temperature of 250° C. or less is an organic compound having an aromatic ring and further a double bond or a triple bond. Examples of the organic compounds include acenaphthylene and vinylnaphthylane. The numeral values attached to the respective compounds shown below are polymerization initiation temperatures of the respective organic compounds. The numeral values are described in "Base of Carbonization Engineering" (1st edition, 2nd printing, Ohmsha, Ltd. 1982).

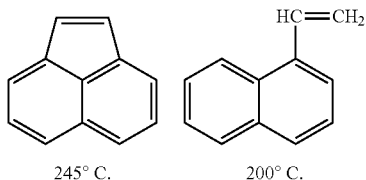

The above metal complex mixture can be heat-treated under the same conditions and the like when the metal complex is independently heat-treated as described above.

The metal complex and the modified metal complex of the present invention can be used in combination with various carriers, additives and the like, and its shape can be processed depending on various applications. The complex can find use in applications including: electrode catalysts and membrane degradation inhibitors for fuel cells; oxidative coupling catalysts for aromatic compounds; catalysts for cleaning an exhaust gas and waste water; redox catalyst layers for dye-sensitized solar cells; carbon dioxide reduction catalysts; catalysts for production of reformed hydrogen; and oxygen sensors.

When the metal complex and the modified metal complex of the present invention are used as a catalyst, the complex can be used as a composition containing a carbon carrier and/or a polymer. Such composition is useful from the following viewpoints: additional improvements in stability and catalytic activity of the modified metal complex. Examples of the polymer include polyethylene, polypropylene, polyacrylonitrile, polyester, polyacetylene, polyaniline, polypyrrole and polythiophene. In addition, specific examples of the carbon carrier are same as those described above. As such composition, there can be used a mixture of the modified metal complexes of the present invention, carbon carriers or conductive polymers, or a combination of a carbon carrier and a conductive polymer.

Hereinafter, preferred applications of the metal complex and the modified metal complex of the present invention are described. The metal complex and the modified metal complex of the present invention can be preferably used as a decomposition catalyst for a peroxide, in particular, a decomposition catalyst for hydrogen peroxide. When the complex is used as a decomposition catalyst for hydrogen peroxide, the complex shows the following characteristic: the complex can decompose hydrogen peroxide into water and oxygen while suppressing the production of a hydroxyl radical. Specifically, the complex can find use in applications including: degradation inhibitors for ionic conduction membranes to be used in solid polymer electrolyte type fuel cells or in the electrolysis of water; and antioxidants for medicine, agricultural chemicals, and food.

The metal complex and the modified metal complex of the present invention are suitable also as an oxidative coupling catalyst for an aromatic compound. In this application, the complex can be used as a catalyst involved in production of a polymer such as polyphenylene ether or polycarbonate. The complex may be directly added to a reaction solution, or supported on conventional catalyst support such as zeolite, silica, and the like. In addition, the metal complexes can be used as organic semiconductor materials such as organic EL materials, organic transistors, and dye sensitization solar cells by taking advantage of the fact that each of the metal complexes has an expanded conjugation.

The metal complex and the modified metal complex of the present invention can be used also as a desulfurization/denitration catalyst for transforming a sulfur oxide or nitrogen oxide in an exhaust gas from various factories and automobiles into sulfuric acid or ammonia. For example, the methods of supplying a tower through which an exhaust gas from a factory passes or a muffler of an automobile with the complex.

Further, the metal complex and the modified metal complex of the present invention can be used also as a catalyst for reforming CO in reformed hydrogen. The reformed hydrogen contains CO and the like, so the following problem arises when the reformed hydrogen is used in a fuel cell: a fuel electrode is poisoned with CO. Accordingly, an utmost reduction of a CO concentration is desired. Specifically, the complex is used in accordance with, for example, the method described in Chemical Communication, 3385 (2005).

The metal complex prepared from using the compound of the present invention is excellent in heat resistance and acid resistance. That is the metal complex is inhibited from decreasing in its catalytic activity and can serve as a catalyst for a wide variety of applications and therefore the metal complex is industrially useful.

The compound of the present invention is a macrocyclic compound and particularly suitable for production of the metal complex showing excellent stability such as heat resistance and acid resistance. The metal complex of the present invention itself has activity as a redox catalysis. Further, a heat-treated metal complex shows a more stable catalytic activity (such as oxygen-reduction ability).

EXAMPLES

The present invention will be described in more detail based on the following examples, but the invention is not intended to be limited thereto.

Macrocyclic Compound (C) was synthesized via Compound (A) and Compound (B) in accordance with the following reaction formula.

Propionic acid manufactured by Wako Pure Chemical Industries, Ltd. was used. Anhydrous methanol and anhydrous dichloromethane each manufactured by Wako Pure Chemical Industries, Ltd. were used. Cobalt acetate tetrahydrate manufactured by Aldrich Inc. was used. WAKOGEL C300 was used as a silica gel.

In the following formulae in Examples, "Boc" represents a tert-butoxycarbonyl group, "dba" represents a dibenzylideneacetone, "Me" represents a methyl group, "Cy" represents a cyclohexyl group, and "Ac" represents an acetyl group.

Example 1

Synthesis of Compound (A)

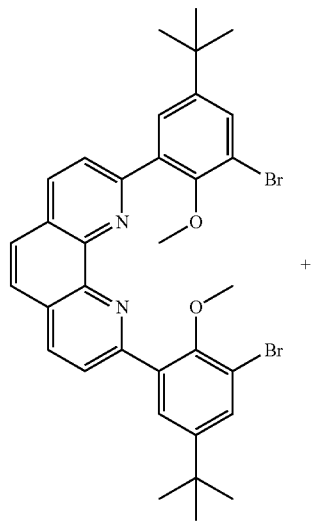

+

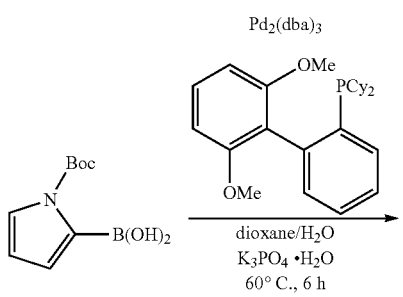

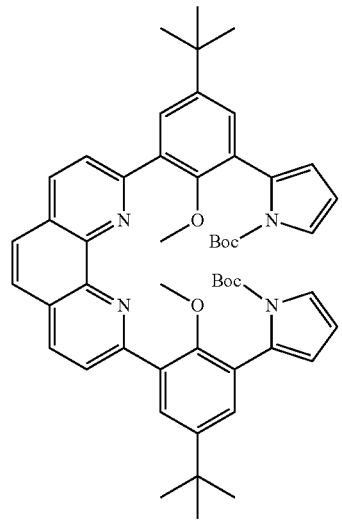

Compound (A)

Under an argon atmosphere, 3.945 g of 2,9-(3'-bromo-5'-tert-butyl-2'-methoxyphenyl)-1,10-phenanthroline (synthesized by the method described in Tetrahedron., 1999, 55, 8377), 3.165 g of 1-N-Boc-pyrrole-2-boronic acid (manufactured by Frontier Scientific), 0.138 g of tris(benzylideneacetone)dipalladium, 0.247 g of 2-dicyclohexylphosphino-2', 6'-dimethoxybiphenyl, and 5.527 g of potassium phosphate were dissolved in mixed solvent of 200 mL of dioxane and 20 mL of water, and the solution was stirred at 60° C. for 6 hours. After the completion of the reaction, the solution was left standing to cool, distilled water and chloroform were added to the solution, and an organic layer was extracted. The resultant organic layer was concentrated, whereby a black residue was obtained. The residue was purified with a silica gel column, whereby Compound (A) was obtained.

¹H-NMR(300 MHz,CDCl₃)δ1.34(s,18H), 1.37(s,18H), 3.30(s,6H), 6.21(m,2H), 6.27(m,2H), 7.37(m,2H), 7.41(s,2H), 7.82(s,2H), 8.00(s 2H), 8.19(d,J=8.6 Hz,2H), 8.27(d,J=8.6 Hz,2H)

Example 2

Synthesis of Compound (B)

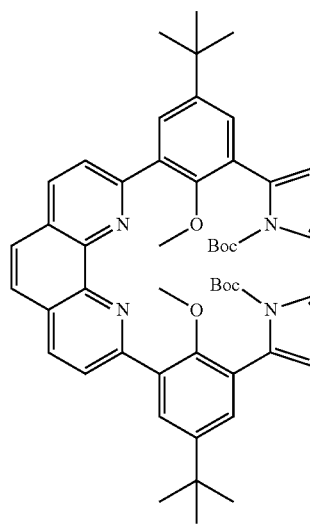

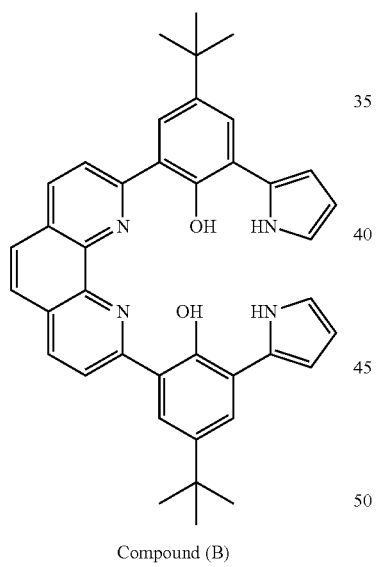

Under a nitrogen atmosphere, 0.904 g of Compound (A) was dissolved in 10 mL of anhydrous dichloromethane. While the dichloromethane solution was cooled to −78° C., 8.8 mL of boron tribromide (1.0-M dichloromethane solution) was slowly dropped to the dichloromethane solution. After the dropping, the mixture was stirred for 10 minutes, and was then left to stand while being stirred so that its temperature might reach room temperature. Three hours after that, the reaction solution was cooled to 0° C., and a saturated aqueous solution of NaHCO₃ was added to the solution. After that, an organic layer was extracted by adding chloroform to the mixture, and was then concentrated. The obtained brown residue was purified with a silica gel column, whereby Compound (B) was obtained.

¹H-NMR(300 MHz,CDCl₃)δ1.40(s,18H), 6.25(m,2H), 6.44(m,2H), 6.74(m,2H), 7.84(s,2H), 7.89(s,2H), 7.92(s,2H), 8.35(d,J=8.4 Hz,2H), 8.46(d,J=8.4 Hz,2H), 10.61(s,2H), 15.88(s,2H)

Example 3

Synthesis of Macrocyclic Compound (C)

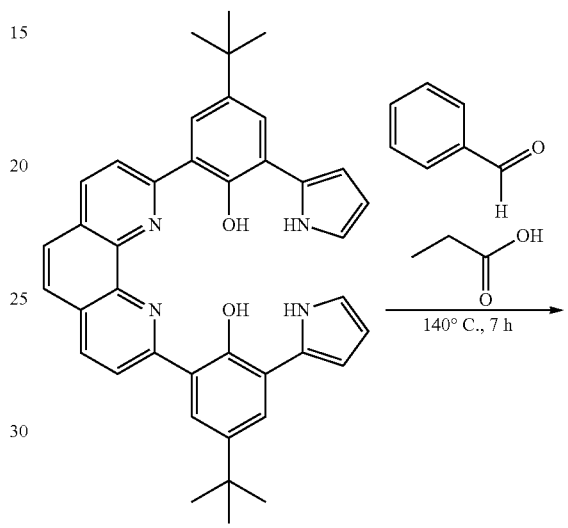

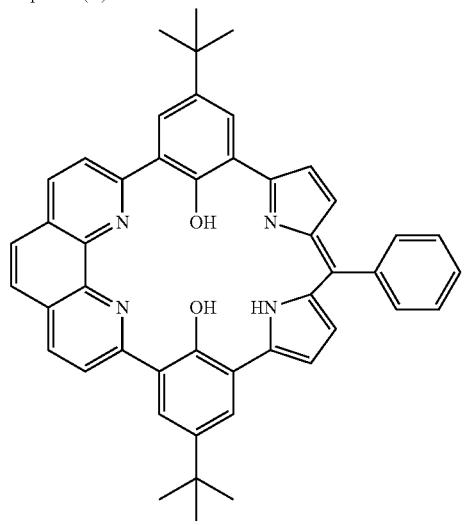

Into 5 mL of propionic acid were dissolved 0.061 g of Compound (B) and 0.012 g of benzaldehyde, and the solution was heated at 140° C. for 7 hours. Thereafter, propionic acid was distilled off, and the resultant black residue was purified through a silica gel column to yield Macrocyclic Compound (C).

¹H-NMR(300 MHz,CDCl₃)δ1.49(s,18H), 6.69(d,J=4.8 Hz,2H), 7.01(d,J=4.8 Hz,2H), 7.57(m,5H), 7.90(s,4H), 8.02(s,2H), 8.31(d,J=8.1 Hz,2H), 8.47(d,J=8.1 Hz,2H)

Macrocyclic Compound (F) was synthesized via Compound (D) and Compound (E) in accordance with the following reaction formula.

Example 4

Synthesis of Compound D

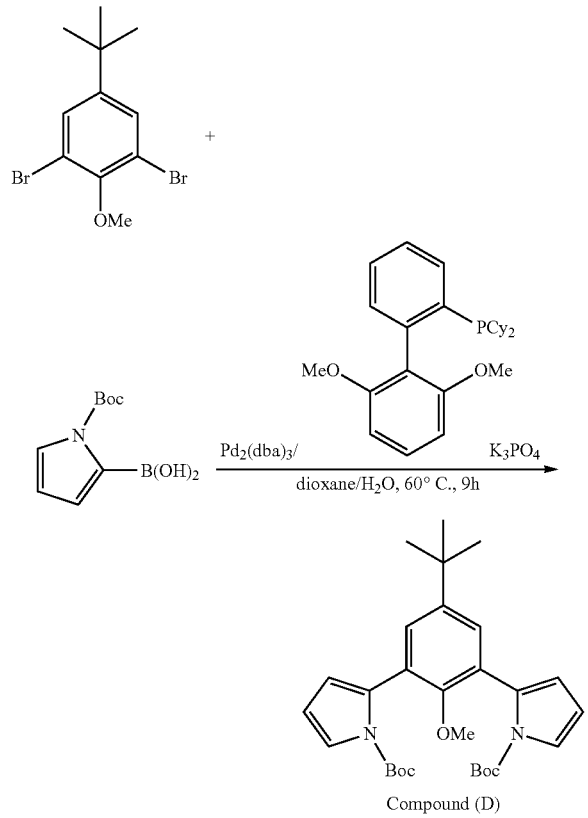

Compound (D)

0.547 g of 2,6-dibromo-4-tert-butylanisole (synthesized by the method described in Tetrahedron. Lett, 1999, 36, 919), 0.844 g of 1-N-Boc-pyrrole-2-boronic acid (manufactured by Frontier Scientific), 0.138 g of tris(benzylideneacetone)dipalladium, 0.247 g of 2-dicyclohexylphosphino-2',6'-dimethoxybiphenyl, and 5.527 g of potassium phosphate were dissolved in mixed solvent of 200 mL of dioxane and 20 mL of water, and the solution was stirred at 60° C. for 9 hours. After the completion of the reaction, the solution was left standing to cool, distilled water and chloroform were added to the solution, and an organic layer was extracted. The resultant organic layer was concentrated, whereby a black residue was obtained. The residue was purified with a silica gel column, whereby Compound (D) was obtained.

$^1$H-NMR(300 MHz,CDCl$_3$)δ1.30(s, 18H), 1.31(s,9H), 3.19(s,3H), 6.19(m,2H), 6.25(m,2H), 7.22(s,2H), 7.38(m, 2H)

Example 5

Compound (E) was synthesized in accordance with the following reaction formula.

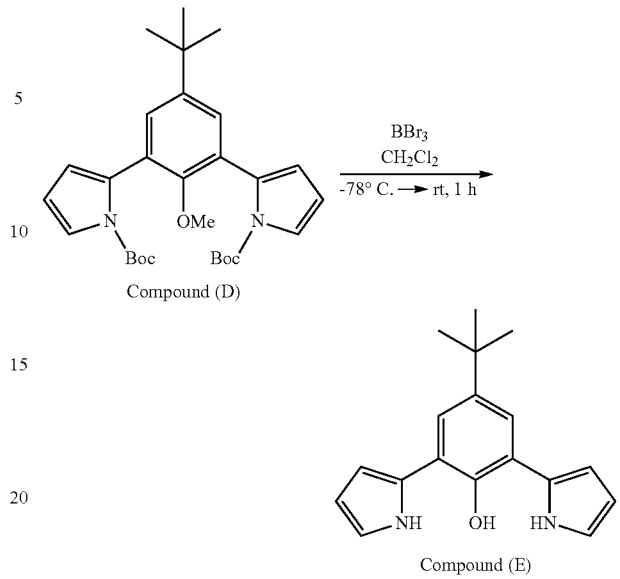

Under a nitrogen atmosphere, 0.453 g of Compound (D) was dissolved in 15 mL of anhydrous dichloromethane. While the dichloromethane solution was cooled to −78° C. in a dry ice/acetone bath, 5.4 mL of boron tribromide (1.0 M dichloromethane solution) was slowly dropped to the dichloromethane solution. After the dropping, the mixture was stirred for 10 minutes. Then, the dry ice/acetone bath was removed, and the mixture was left to stand while being stirred so that its temperature might reach room temperature. An hour after that, the resultant was neutralized with a saturated aqueous solution of NaHCO$_3$, and then an organic layer was extracted three times by adding chloroform to the mixture. The obtained organic layer was concentrated, and the obtained black residue was purified, whereby Compound (E) was obtained.

$^1$H-NMR(300 MHz,CDCl$_3$)δ1.34(s,9H), 6.35(m,2H), 6.40(s,1H), 6.55(m,2H), 6.93(m,2H), 7.36(s,2H), 9.15(s,2H)

Example 6

Macrocyclic Compound (F) was synthesized in accordance with the following reaction formula.

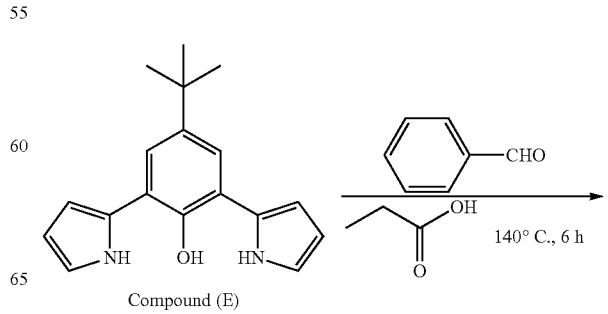

Compound (E)

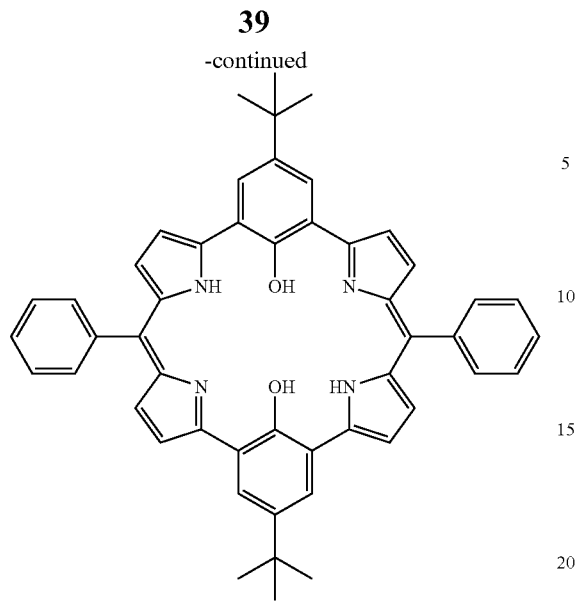

Macrocyclic Compound (F)

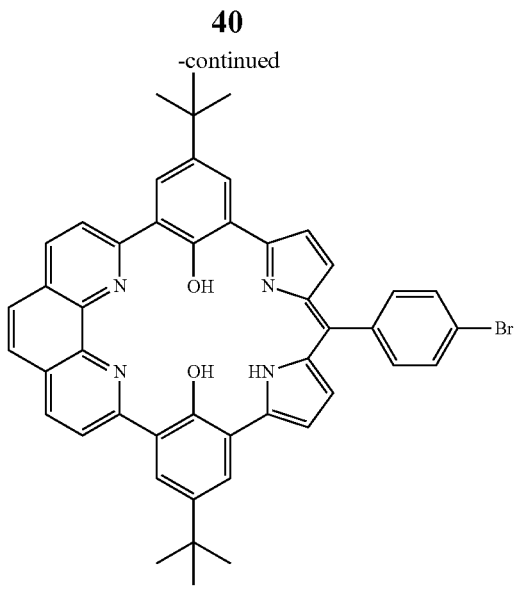

Macrocyclic Compound (G)

Into 20 mL of propionic acid were dissolved 0.051 g of Compound (E) and 0.019 g of benzaldehyde, and the solution was heated at 140° C. for 7 hours. Thereafter, propionic acid was distilled off, and the resultant black residue was purified through a silica gel to yield Macrocyclic Compound (F).

$^1$H-NMR(300 MHz,CDCl$_3$)δ1.38(s,18H), 6.58(d,J=3.8 Hz,4H), 6.92(d,J=3.8 Hz,4H), 7.49(m,10H), 7.71(s,4H), 12.75(br,4H)

Into 20 mL of propionic acid were dissolved 0.166 g of Compound (B) and 0.065 g of 4-bromobenzaldehyde (manufactured by Aldrich), and the solution was heated at 140° C. for 5 hours. Thereafter, propionic acid was distilled off, and the resultant black residue was purified through a silica gel column to yield Macrocyclic Compound (G).

$^1$H-NMR(300 MHz,CDCl$_3$)δ1.43(s,18H), 6.59(d,J=4.2 Hz,2H), 6.95(d,J=4.2 Hz,2H), 7.44(d,J=7.0 Hz,2H), 7.63(d, J=7.0 Hz,2H), 7.73(s,2H), 7.82(s,2H), 7.89(s,2H), 8.16(d, J=8.6 Hz,2H), 8.29(d,J=8.6 Hz,2H)

Example 7

Macrocyclic Compound (G) was synthesized in accordance with the following reaction formula.

Example 8

Macrocyclic Compound (H) was synthesized in accordance with the following reaction formula.

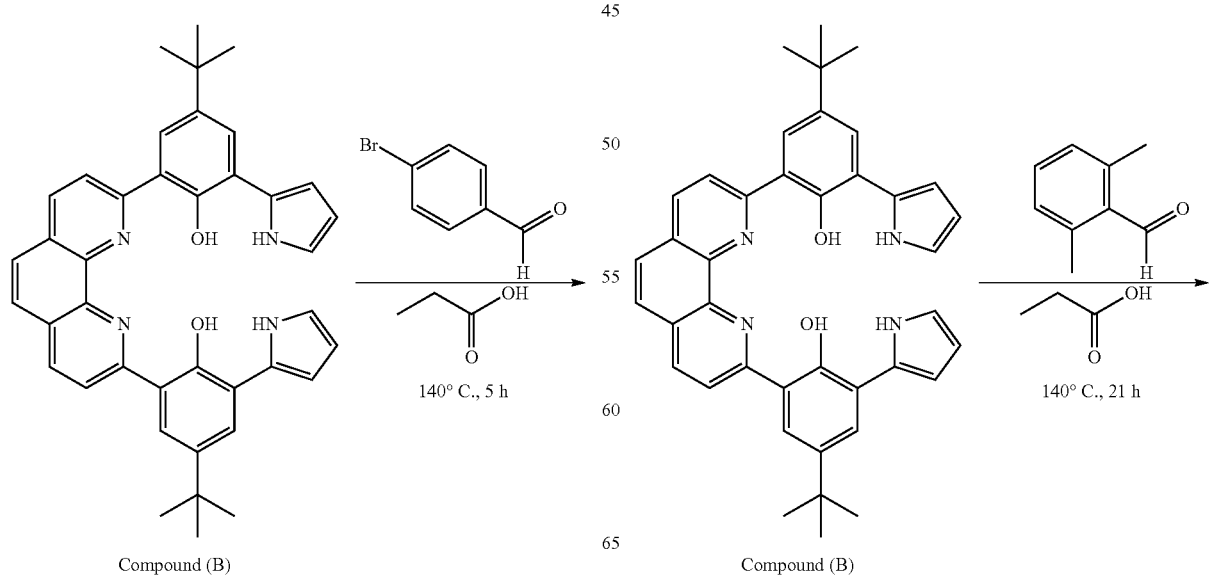

Compound (B)            Compound (B)

-continued

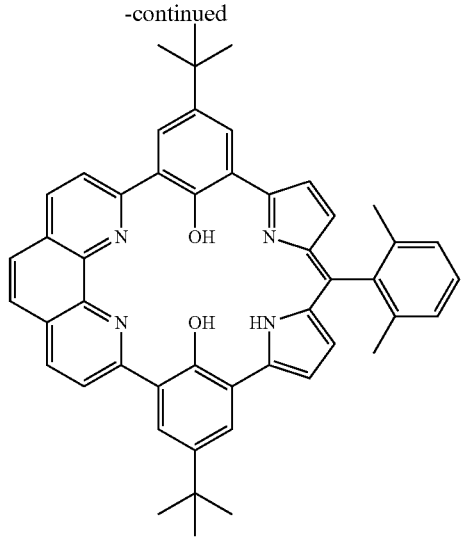

Macrocyclic Compound (H)

Into 15 mL of propionic acid were dissolved 0.100 g of Compound (B) and 0.025 g of 2,6-dimethylbenzaldehyde (manufactured by Aldrich), and the solution was heated at 140° C. for 21 hours. Thereafter, propionic acid was distilled off, and the resultant black residue was purified through a silica gel column to yield Macrocyclic Compound (H).

$^1$H-NMR(300 MHz,CDCl$_3$)δ1.43(s,18H), 62.26(s,6H), 6.47(d,J=4.2 Hz,2H), 6.94(d,J=4.2 Hz,2H), 7.17(d,J=7.7 Hz,2H), 7.63(d,J=7.0 Hz,2H), 7.73(s,2H), 7.82(s,2H), 7.89(s,2H), 8.16(d,J=8.6 Hz,2H), 8.29(d,J=8.6 Hz,2H)

Example 9

Macrocyclic Compound (I) was synthesized in accordance with the following reaction formula.

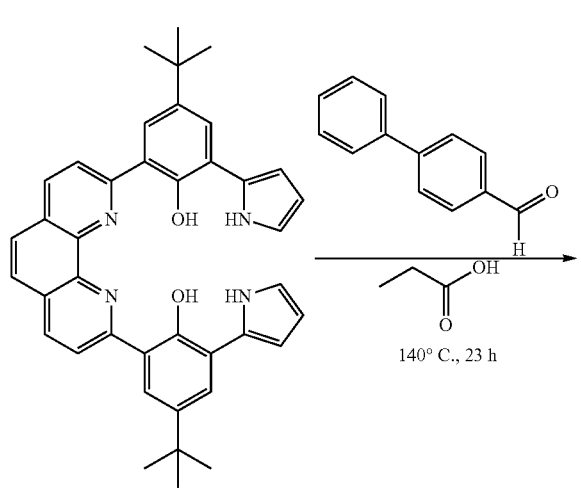

Compound (B)

-continued

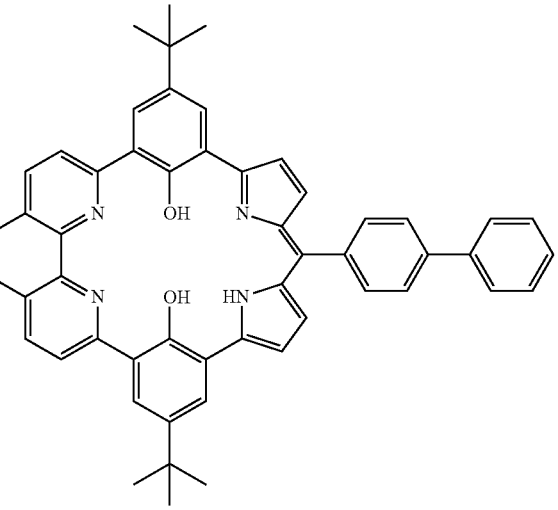

Macrocyclic Compound (I)

Into 15 mL of propionic acid were dissolved 0.100 g of Compound (B) and 0.033 g of biphenyl-4-carboxyaldehyde (manufactured by Aldrich), and the solution was heated at 140° C. for 23 hours. Thereafter, propionic acid was distilled off, and the resultant black residue was purified through a silica gel column to yield Macrocyclic Compound (I).

$^1$H-NMR(300 MHz,CDCl$_3$)δ1.44(s,18H), 6.74(d,J=3.7 Hz,2H), 6.98(d,J=3.7 Hz,2H), 7.53(t,J=6.8 Hz,2H), 7.63(d, J=8.4 Hz,2H), 7.74(d,J=7.5 Hz,4H), 7.84(s,4H), 7.96(s,2H), 8.24(d,J=8.6 Hz,2H), 8.41(d,J=8.6 Hz,2H)

Example 10

Macrocyclic Compound (J) was synthesized in accordance with the following reaction formula.

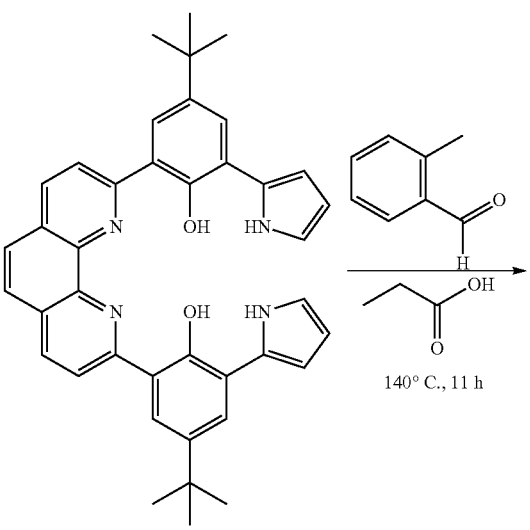

Compound (B)

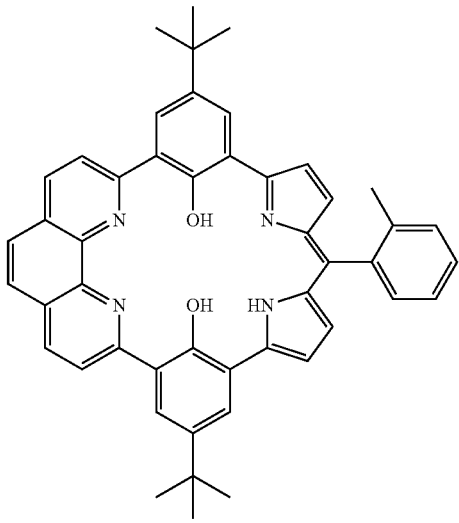

Macrocyclic Compound (J)

Into 15 mL of propionic acid were dissolved 0.050 g of Compound (B) and 0.012 g of o-tolualdehyde (manufactured by Aldrich), and the solution was heated at 140° C. for 11 hours. Thereafter, propionic acid was distilled off, and the resultant black residue was purified through a silica gel column to yield Macrocyclic Compound (J).

$^1$H-NMR(300 MHz,CDCl$_3$)δ1.43(s,18H), 2.28(s,3H), 6.47(d,J=4.2 Hz,2H), 6.93(d,J=4.2 Hz,2H), 7.30-7.33(m, 4H), 7.77(s,2H), 7.85(s,2H), 7.91(s,2H), 8.21(d,J=8.8 Hz,2H), 8.33(d,J=8.8 Hz,2H)

Example 11

Macrocyclic Compound (K) was synthesized in accordance with the following reaction formula.

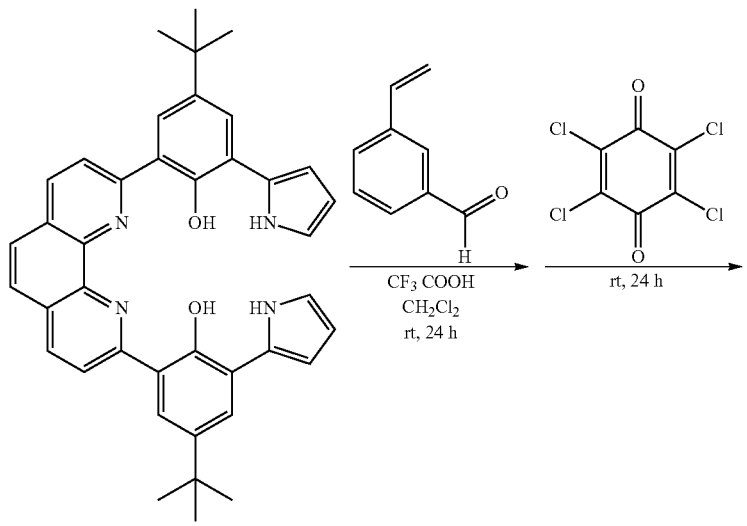

Compound (B)

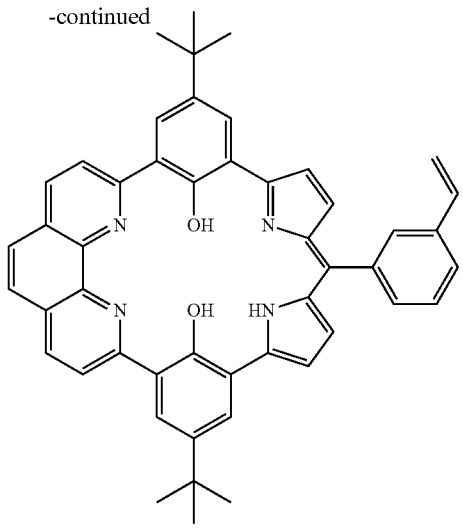

Macrocyclic Compound (K)

Into 30 mL of dichloromethane were dissolved 0.121 g of Compound (B) and 0.030 g of 3-vinylbenzaldehyde (manufactured by Aldrich), and the solution was stirred for 24 hours at room temperature after adding one drop of trifluoroacetic acid. Then, into the solution was added 0.050 g of chloranil, and further the solution was stirred for 24 hours at room temperature. Thereafter, dichloromethane was distilled off, and the resultant black residue was purified through a silica gel column to yield Macrocyclic Compound (K).

$^1$H-NMR(300 MHz,CDCl$_3$)δ1.42(s,18H), 5.34(d,J=10.8 Hz,1H), 5.87(d,J=17.8 Hz,1H), 6.65(d,J=4.2 Hz,2H), 6.86 (dd,J1=17.8 Hz,J2=10.8 Hz1H), 6.95(d,J=4.2 Hz,2H), 7.46-7.62(m,6H), 7.90(s,4H), 7.81(s,4H), 8.01(d,J=8.6 Hz,2H), 8.13(d,J=8.8 Hz,2H)

Example 12

Macrocyclic Compound (L) was synthesized in accordance with the following reaction formula.

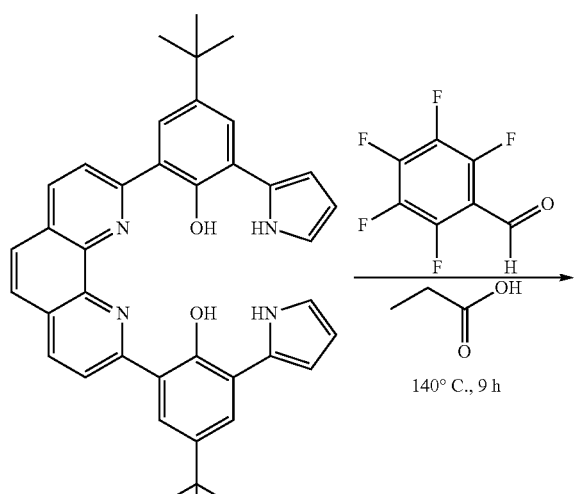

Compound (B)

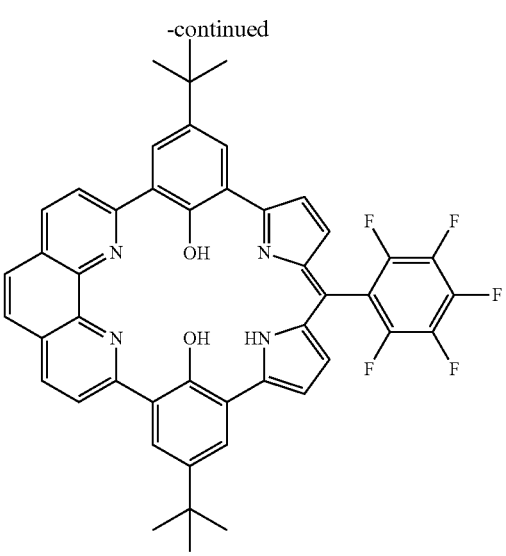

Macrocyclic Compound (L)

Into 15 mL of propionic acid were dissolved 0.061 g of Compound (B) and 0.022 g of pentafluorobenzaldehyde (manufactured by Wako), and the solution was heated at 140° C. for 9 hours. Thereafter, propionic acid was distilled off, and the resultant black residue was purified through a silica gel column to yield Macrocyclic Compound (L).

$^1$H-NMR(300 MHz,CDCl$_3$)δ1.36(s,18H), 6.56(d,J=4.0 Hz,2H), 6.92(d,J=4.0 Hz,2H), 7.16(s,2H), 7.51(s,2H), 7.59 (s,2H), 7.62(d,J=8.4 Hz,2H), 7.71(d,J=8.4 Hz,2H)

Example 13

Macrocyclic Compound (M) was synthesized in accordance with the following reaction formula.

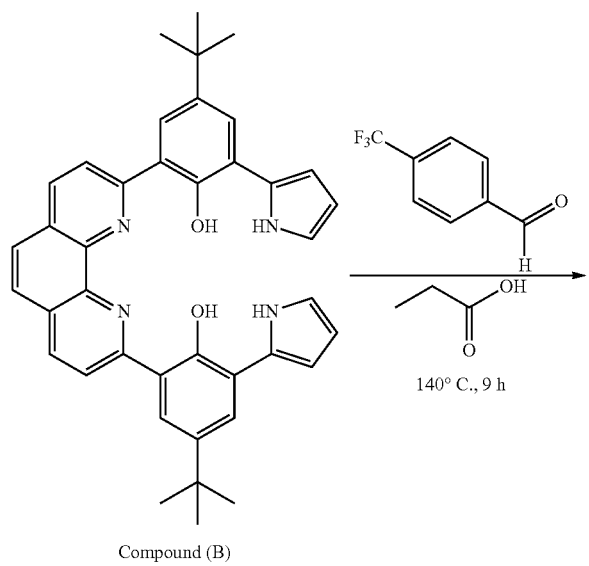

Compound (B)

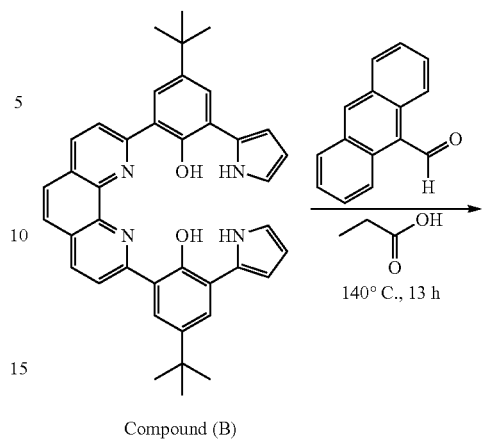

Compound (B)

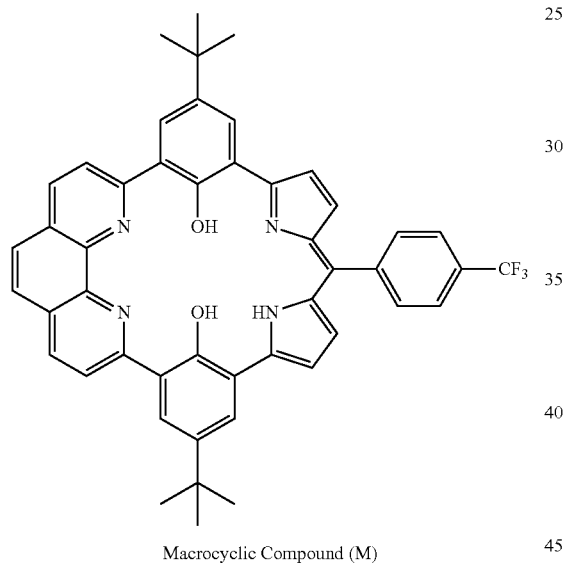

Macrocyclic Compound (M)

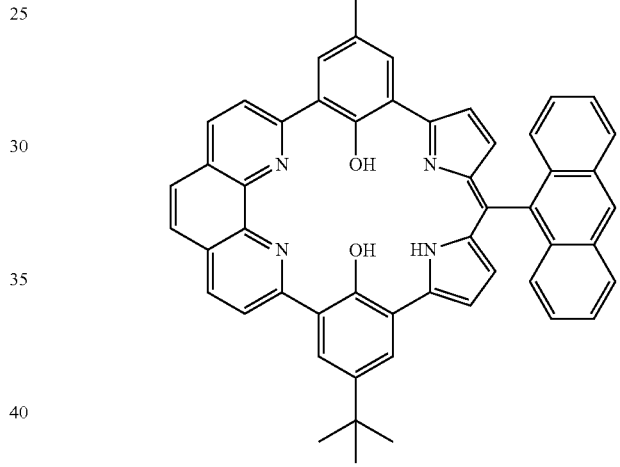

Macrocyclic Compound (N)

Into 15 mL of propionic acid were dissolved 0.061 g of Compound (B) and 0.019 g of p-trifluoromethylbenzaldehyde (manufactured by Wako), and the solution was heated at 140° C. for 9 hours. Thereafter, propionic acid was distilled off, and the resultant black residue was purified through a silica gel column to yield Macrocyclic Compound (M).

$^1$H-NMR(300 MHz,CDCl$_3$)δ1.37(s,18H), 6.47(d,J=4.4 Hz,2H), 6.89(d,J=4.4 Hz,2H), 7.60-7.74(m,8H), 7.79(s,2H), 8.03(d,J=8.8 Hz,2H), 8.16(d,J=8.8 Hz,2H)

Into 50 mL of propionic acid were dissolved 0.121 g of Compound (B) and 0.045 g of 9-anthracenecarboxyaldehyde (manufactured by TCI), and the solution was heated at 140° C. for 13 hours. Thereafter, propionic acid was distilled off, and the resultant black residue was purified through a silica gel column to yield Macrocyclic Compound (N).

$^1$H-NMR(300 MHz,CDCl$_3$)δ1.41(s,18H), 6.07(d,J=4.4 Hz,2H), 6.80(d,J=4.4 Hz,2H), 7.35-7.49(m,4H), 7.85(s,4H), 7.98(s,2H), 8.07(d,J=8.4 Hz,2H), 8.11(d,J=8.8 Hz,2H), 8.31 (d,J=8.8 Hz,2H), 8.40(d,J=8.8 Hz,2H), 8.58(s,2H)

Example 14

Macrocyclic Compound (N) was synthesized in accordance with the following reaction formula.

Example 15

Macrocyclic Compound (O) was synthesized in accordance with the following reaction formula.

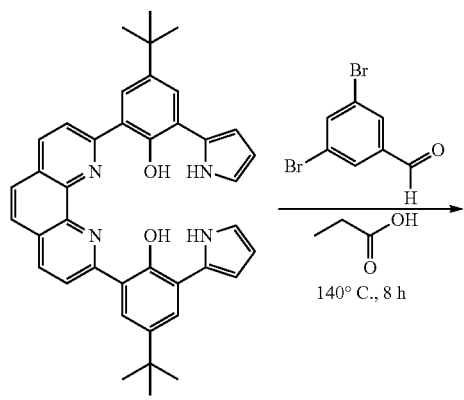

Compound (B)

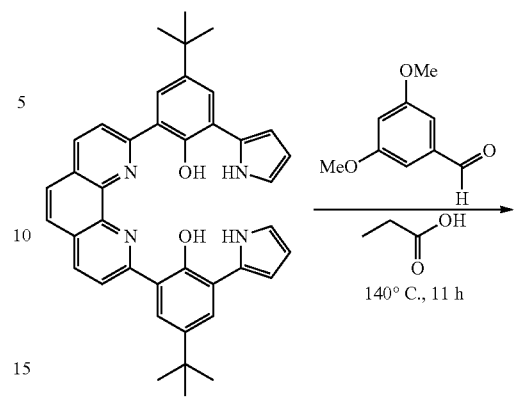

Compound (B)

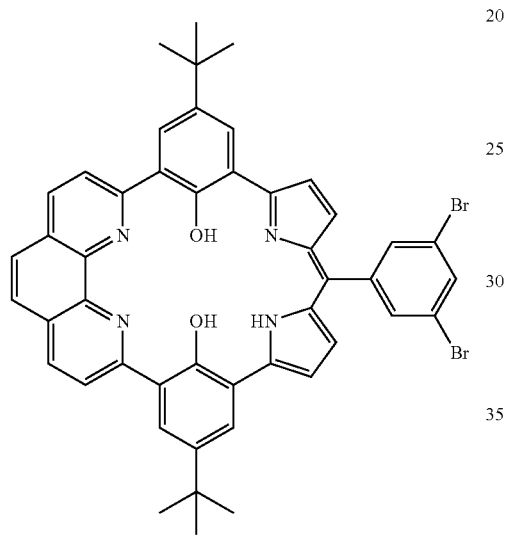

Macrocyclic Compound (O)

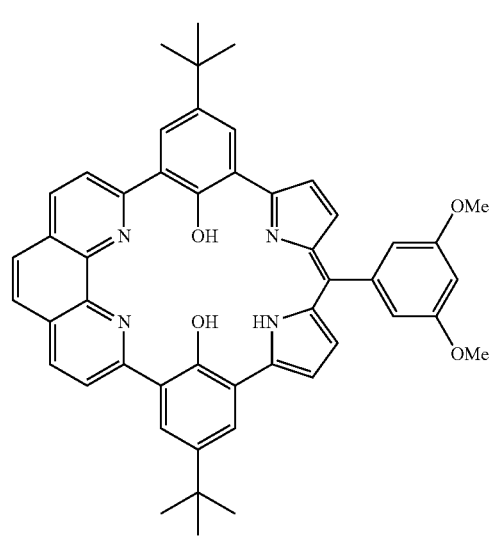

Macrocyclic Compound (P)

Into 35 mL of propionic acid were dissolved 0.121 g of Compound (B) and 0.063 g of 3,5-dibromobenzaldehyde (manufactured by Aldrich), and the solution was heated at 140° C. for 8 hours. Thereafter, propionic acid was distilled off, and the resultant black residue was purified through a silica gel column to yield Macrocyclic Compound (O).

$^1$H-NMR(300 MHz,CDCl$_3$)δ1.33(s,18H), 6.57(d,J=4.0 Hz,2H), 6.92(d,J=4.0 Hz,2H), 7.51(m,3H), 7.60(s,2H), 7.74 (s,2H), 7.85(s,2H), 7.90(d,J=8.6 Hz,2H), 8.12(d,J=8.6 Hz,2H)

Into 20 mL of propionic acid were dissolved 0.061 g of Compound (B) and 0.019 g of 3,5-dimethoxybenzaldehyde (manufactured by TCI), and the solution was heated at 140° C. for 11 hours. Thereafter, propionic acid was distilled off, and the resultant black residue was purified through a silica gel column to yield Macrocyclic Compound (P).

$^1$H-NMR(300 MHz,CDCl$_3$)δ1.38(s,18H), 3.89(s,6H), 6.65(s,1H), 6.73(m,4H), 6.94(d,J=3.5 Hz,2H), 7.72(s,2H), 7.80(s,2H), 7.86(s,2H), 8.12(d,J=7.9 Hz,2H), 8.28(d,J=7.9 Hz,2H)

Example 16

Macrocyclic Compound (P) was synthesized in accordance with the following reaction formula.

Example 17

Macrocyclic Compound (Q) was synthesized in accordance with the following reaction formula.

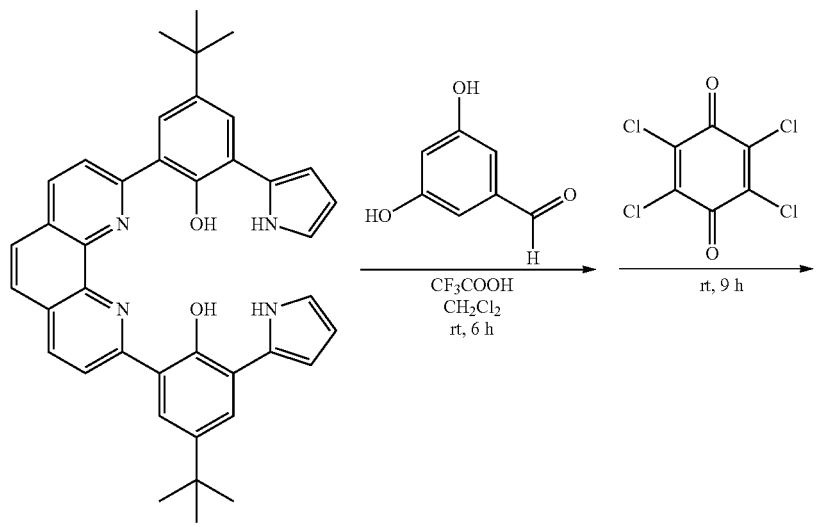

Compound (B)

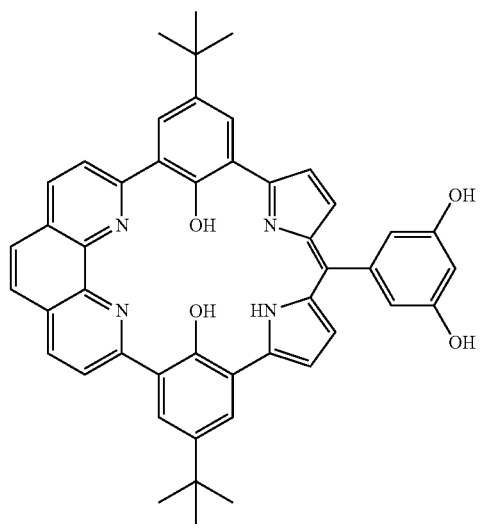

Macrocyclic Compound (Q)

Into 20 mL of dichloromethane were dissolved 0.121 g of Compound (B) and 0.031 g of 3,5-dihydroxybenzaldehyde (manufactured by Wako), and the solution was stirred for 6 hours at room temperature after adding one drop of trifluoroacetic acid. Then, into the solution was added 0.050 g of chloranil, and further the solution was stirred for 9 hours at room temperature. Thereafter, dichloromethane was distilled off, and the resultant black residue was washed with chloroform to yield Macrocyclic Compound (O).

$^1$H-NMR(300 MHz,CDCl$_3$)δ1.49(s,18H), 6.69(d,J=4.8 Hz,2H), 7.01(d,J=4.8 Hz,2H), 7.57(m,5H), 7.90(s,4H), 8.02 (s,2H), 8.31(d,J=8.1 Hz,2H), 8.47(d,J=8.1 Hz,2H)

Example 18

Macrocyclic Compound (R) was synthesized in accordance with the following reaction formula.

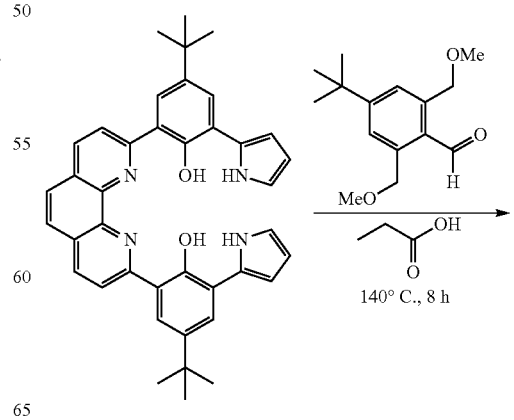

Compound (B)

53

-continued

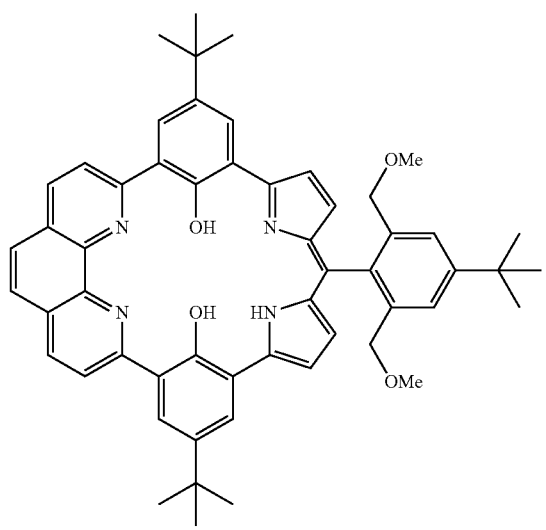

Macrocyclic Compound (R)

54

-continued

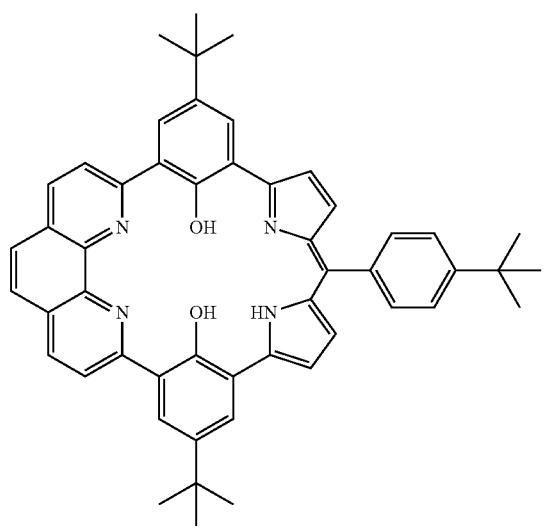

Macrocyclic Compound (S)

Into 15 mL of propionic acid were dissolved 0.061 g of Compound (B) and 0.042 g of 2,6-bis(methoxymethyl)benzaldehyde, and the solution was heated at 140° C. for 8 hours. Thereafter, propionic acid was distilled off, and the resultant black residue was purified through a silica gel column to yield Macrocyclic Compound (R).

$^1$H-NMR(300 MHz,CDCl$_3$)δ1.39(s,18H), 1.53(s,9H), 3.32(s,6H), 4.50(s,4H), 6.56(d,J=3.8 Hz,2H), 7.00(d,J=3.7 Hz,2H), 7.65(s,2H), 7.75(s,2H), 7.90(s,2H), 7.99(s,2H), 8.27 (d,J=8.6 Hz,2H), 8.35(d,J=8.6 Hz,2H)

Into 15 mL of propionic acid were dissolved 0.061 g of Compound (B) and 0.042 g of 4-tert-butylbenzaldehyde (manufactured by TCI), and the solution was heated at 140° C. for 6 hours. Thereafter, propionic acid was distilled off, and the resultant black residue was purified through a silica gel column to yield Macrocyclic Compound (S).

$^1$H-NMR(300 MHz,CDCl$_3$)δ1.39(s,18H), 1.53(s,9H), 6.70(d,J=4.2 Hz,2H), 6.89(d,J=4.4 Hz,2H), 7.32(s,2H), 7.51 (d,J=7.5 Hz,2H), 7.59-7.62(m,6H), 7.72(d,J=9.0 Hz,2H), 7.90(d,J=8.6 Hz,2H)

Example 19

Macrocyclic Compound (S) was synthesized in accordance with the following reaction formula.

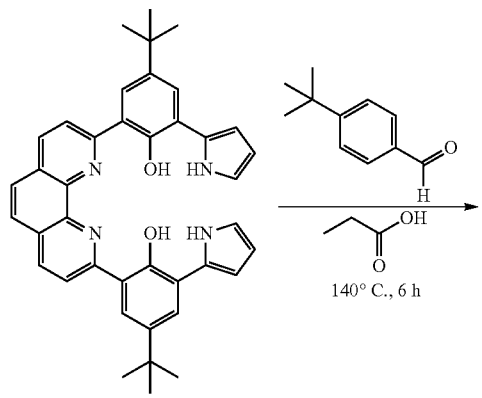

Compound (B)

Example 20

Macrocyclic Compound (T) was synthesized in accordance with the following reaction formula.

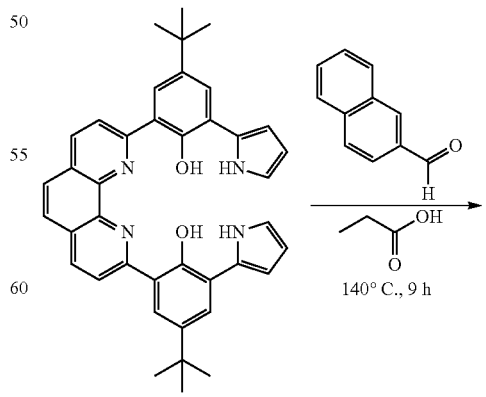

Compound (B)

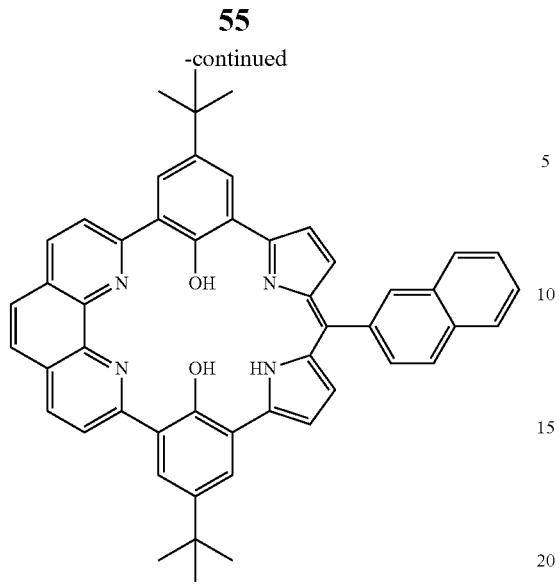

Macrocyclic Compound (T)

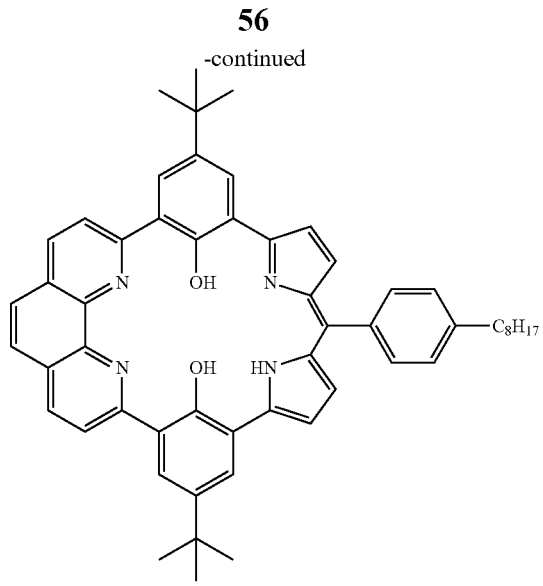

Macrocyclic Compound (U)

Into 20 mL of propionic acid were dissolved 0.100 g of Compound (B) and 0.028 g of 2-naphthoaldehyde (manufactured by TCI), and the solution was heated at 140° C. for 9 hours. Thereafter, propionic acid was distilled off, and the resultant black residue was purified through a silica gel column to yield Macrocyclic Compound (T).

$^1$H-NMR(300 MHz,CDCl$_3$)δ1.42(s,18H), 6.62(d,J=3.8 Hz,2H), 6.92(d,J=4.0 Hz,2H), 7.59-7.62(m,2H), 7.67(s,2H), 7.70(s,1H), 7.79(s,2H), 7.84(s,2H), 7.94-7.97(m,3H), 8.04(s,1H), 8.08(d,J=8.8 Hz,2H), 8.23(d,J=8.4 Hz,2H)

Into 20 mL of propionic acid were dissolved 0.100 g of Compound (B) and 0.044 g of 4-octylbenzaldehyde (manufactured by ACROS), and the solution was heated at 140° C. for 8 hours. Thereafter, propionic acid was distilled off, and the resultant black residue was purified through a silica gel column to yield Macrocyclic Compound (U).

$^1$H-NMR(300 MHz,CDCl$_3$)δ0.94(t,J=6.2 Hz,3H), 1.35-1.43(m,30H), 1.72-1.79(m,2H), 2.78(t,J=7.5 Hz,2H), 6.68(d, J=3.3 Hz,2H), 6.92(d,J=3.3 Hz,2H), 7.35(d,J=7.3 Hz,2H), 7.44(d,J=7.3 Hz,2H), 7.52(s,2H), 7.66(s,2H), 7.71 (s,2H), 7.89(d,J=8.2 Hz,2H), 8.12(d,J=8.2 Hz,2H)

Example 21

Macrocyclic Compound (U) was synthesized in accordance with the following reaction formula.

Example 22

Metal Complex (AA) was synthesized in accordance with the following reaction formula.

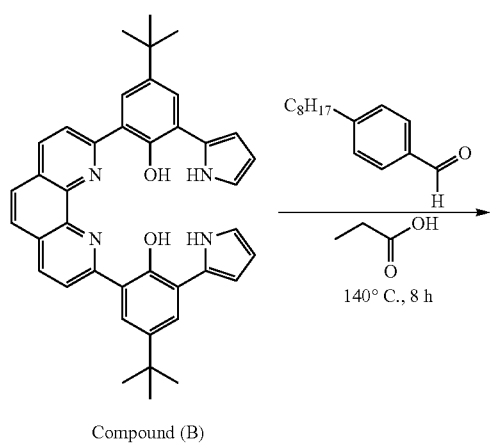

Compound (B)

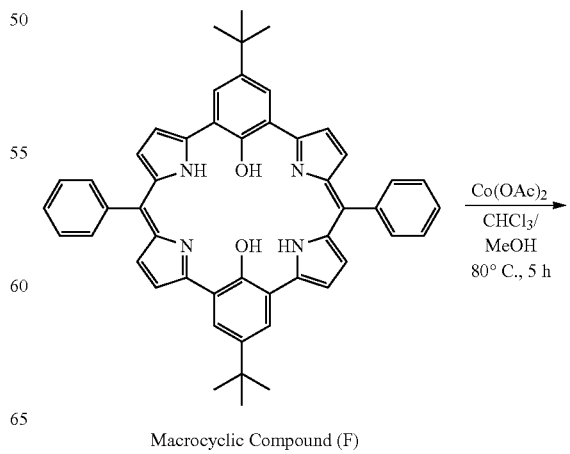

Macrocyclic Compound (F)

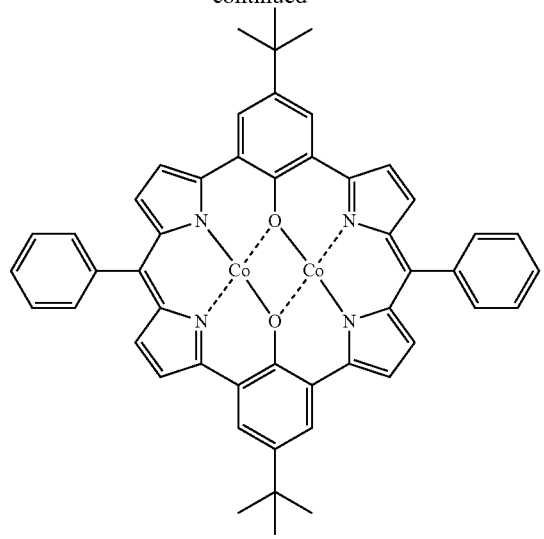

Metal Complex (AA)

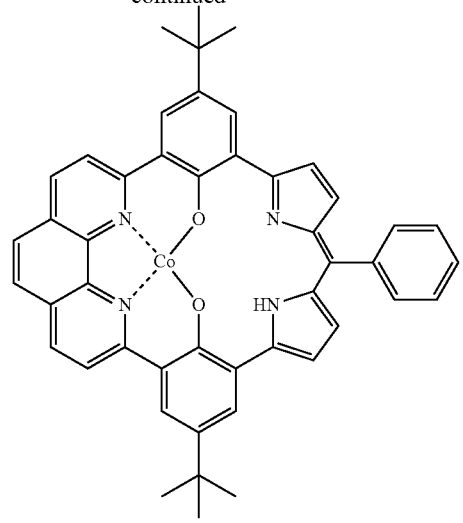

Metal Complex (AB)

While a mixed solution of 4 mL of methanol and 6 mL of chloroform containing 0.057 g of Macrocyclic Compound (F) and 0.047 g of cobalt acetate tetrahydrate was stirred under a nitrogen atmosphere, the solution was stirred for 5 hours while being heated at 80° C. The resultant solution was concentrated and dried to be solidified. As a result, a purple solid was yielded. This was washed with water to yield Metal Complex (AA).

ESI-MS[M.]$^+$: m/z=846.0

While a mixed solution of 3 mL of methanol and 3 mL of chloroform containing 0.047 g of Macrocyclic Compound (C) and 0.018 g of cobalt acetate tetrahydrate was stirred under a nitrogen atmosphere, the solution was stirred for 5 hours while being heated at 80° C. The resultant solution was concentrated and dried to be solidified. As a result, a green solid was yielded. This was washed with water to yield Metal Complex (AB).

ESI-MS[M.]$^+$: m/z=749.0

Example 23

Metal Complex (AB) was synthesized in accordance with the following reaction formula.

Example 24

Metal Complex (AC) was synthesized in accordance with the following reaction formula.

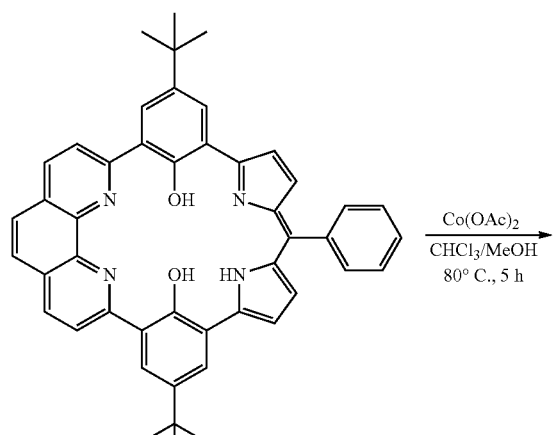

Macrocyclic Compound (C)

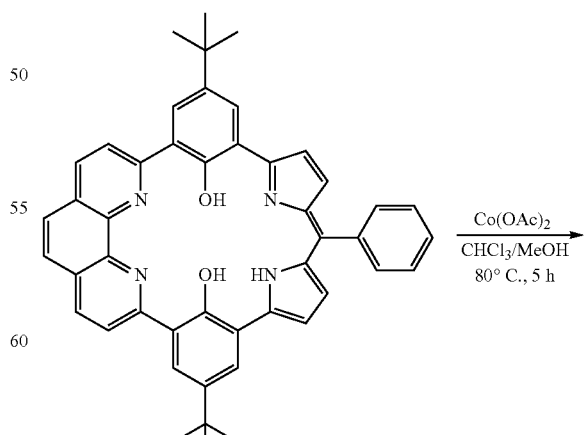

Macrocyclic Compound (C)

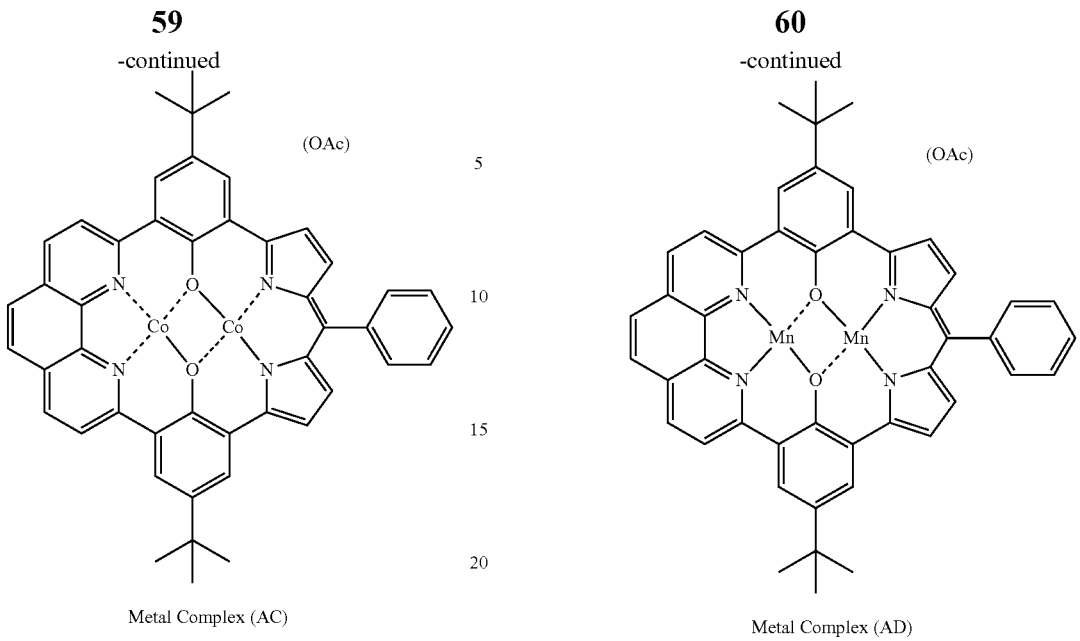

Metal Complex (AC)

Metal Complex (AD)

While a mixed solution of 3 mL of methanol and 3 mL of chloroform containing 0.045 g of Macrocyclic Compound (C) and 0.040 g of cobalt acetate tetrahydrate was stirred under a nitrogen atmosphere, the solution was stirred for 5 hours while being heated at 80° C. The resultant solution was concentrated and dried to be solidified. As a result, a blue solid was yielded. This was washed with water to yield Metal Complex (AC).

ESI-MS[M.]$^+$: m/z=866.0

Under a nitrogen atmosphere, 0.100 g of Macrocyclic Compound (C) and 20 mL of chloroform were loaded into a 50-mL two-necked flask, and a solution of 10 mL of methanol containing 0.074 g of manganic acetate tetrahydrate (manufactured by Wako) was added thereto. The solution was stirred for 10 hours while being heated at 70° C., whereby a blue-green solid was precipitated. The resultant solution was concentrated and dried to be solidified. As a result, a green solid was yielded. This was washed with water and dried to yield Metal Complex (AD).

ESI-MS[M.]$^+$: m/z=858.0

Example 25

Metal Complex (AD) was synthesized in accordance with the following reaction formula.

Example 26

Metal Complex (AE) was synthesized in accordance with the following reaction formula.

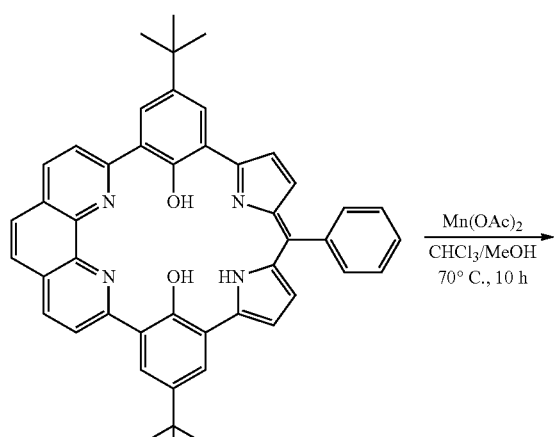

Macrocyclic Compound (C)

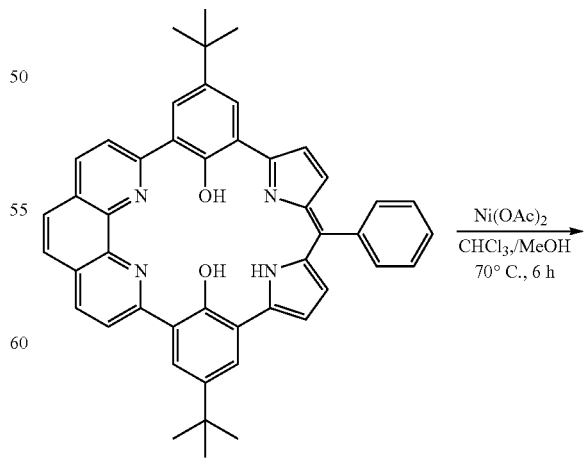

Macrocyclic Compound (C)

-continued

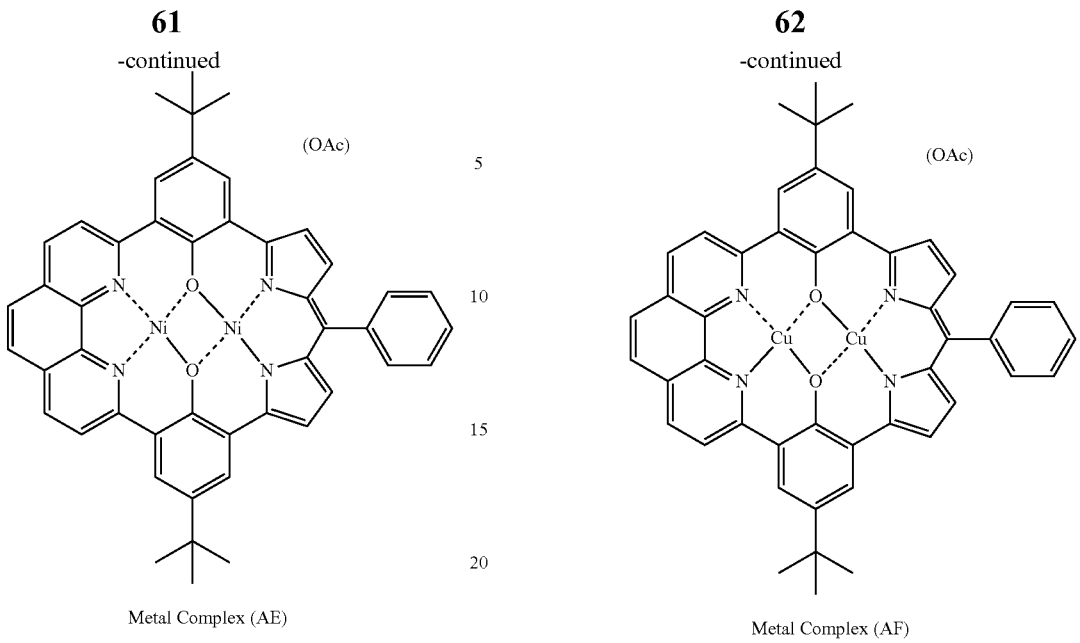

Metal Complex (AE)

Metal Complex (AF)

Under a nitrogen atmosphere, 0.10 g of Macrocyclic Compound (C) and 20 mL of chloroform were loaded into a 100-mL two-necked flask, and a solution of 10 mL of methanol containing 0.075 g of nickel acetate tetrahydrate (manufactured by Wako) was added thereto. The solution was stirred for 6 hours while being heated at 70° C. The resultant solution was concentrated and dried to be solidified. As a result, a blue-green solid was yielded. This was washed with water and dried to yield Metal Complex (AE).

ESI-MS[M−OAc]$^+$: m/z=805.0

Under a nitrogen atmosphere, 0.100 g of Macrocyclic Compound (C) and 20 mL of chloroform were loaded into a 100-mL two-necked flask, and a solution of 10 mL of methanol containing 0.060 g of copper acetate monohydrate (manufactured by Wako) was added thereto. The solution was refluxed for 5 hours while being heated at 70° C., whereby a dark-green solid was precipitated. The resultant solution was concentrated and dried to be solidified. The residue was washed with water and dried to yield Metal Complex (AF).

ESI-MS[M−OAc]$^+$: m/z=815.0

Example 27

Metal Complex (AF) was synthesized in accordance with the following reaction formula.

Example 28

Metal Complex (AG) was synthesized in accordance with the following reaction formula.

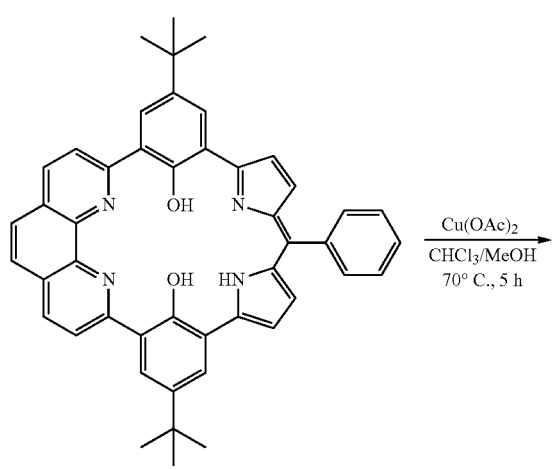

Macrocyclic Compound (C)

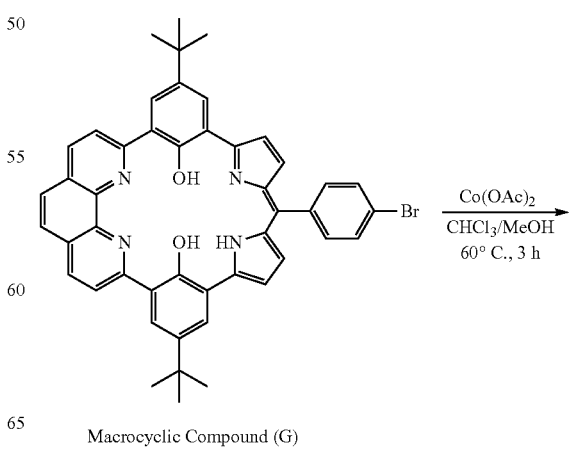

Macrocyclic Compound (G)

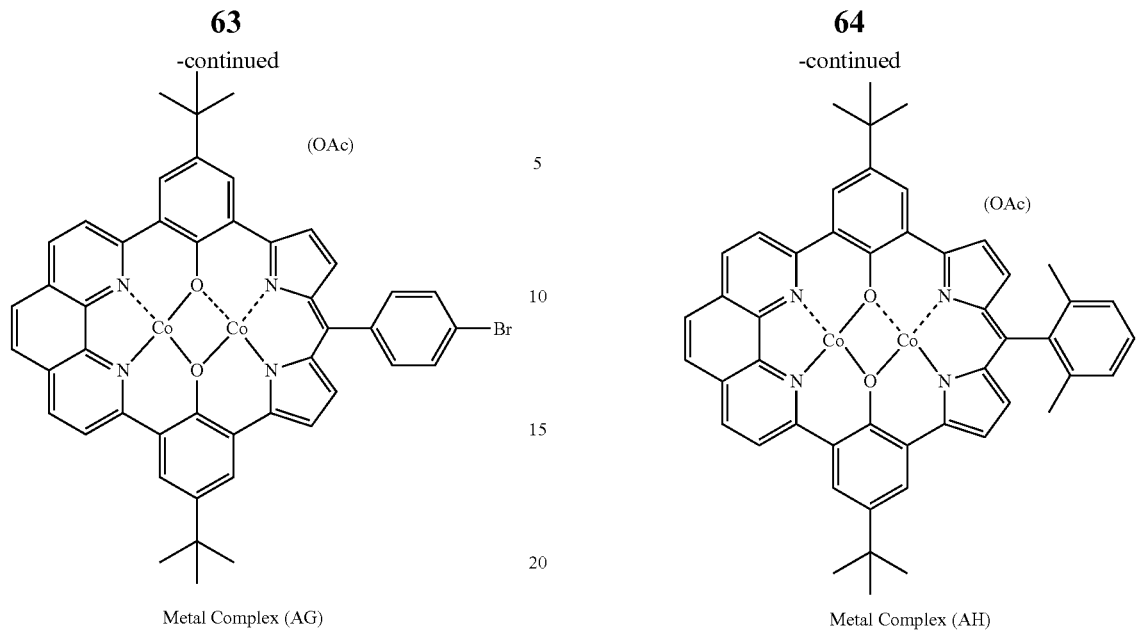

Metal Complex (AG)

Metal Complex (AH)

While a mixed solution of 5 mL of methanol and 5 mL of chloroform containing 0.025 g of Macrocyclic Compound (G) and 0.020 g of cobalt acetate tetrahydrate was stirred under a nitrogen atmosphere, the solution was stirred for 3 hours while being heated at 60° C. The resultant solution was concentrated and dried to be solidified. As a result, a blue solid was yielded. This was washed with water to yield Metal Complex (AG).

ESI-MS[M.]$^+$: m/z=946.0

While a mixed solution of 4 mL of methanol and 4 mL of chloroform containing 0.024 g of Macrocyclic Compound (H) and 0.020 g of cobalt acetate tetrahydrate was stirred under a nitrogen atmosphere, the solution was stirred for 8 hours while being heated at 80° C. The resultant solution was concentrated and dried to be solidified. As a result, a blue solid was yielded. This was washed with water to yield Metal Complex (AH).

ESI-MS[M.]$^+$: m/z=894.1

Example 29

Metal Complex (AH) was synthesized in accordance with the following reaction formula.

Example 30

Metal Complex (AI) was synthesized in accordance with the following reaction formula.

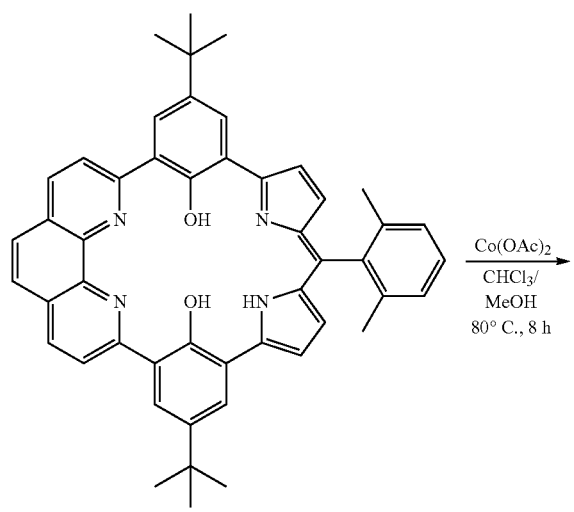

Macrocyclic Compound (H)

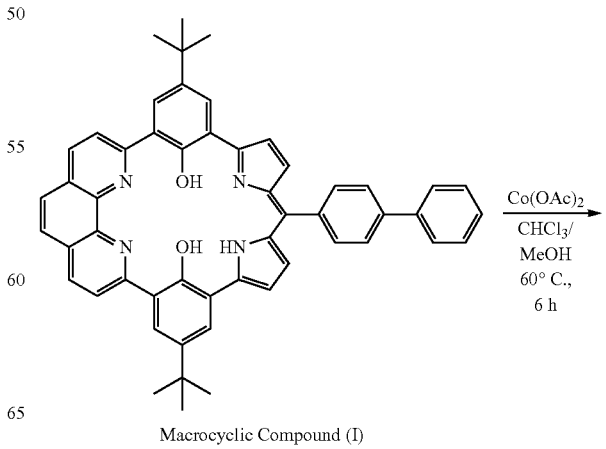

Macrocyclic Compound (I)

-continued

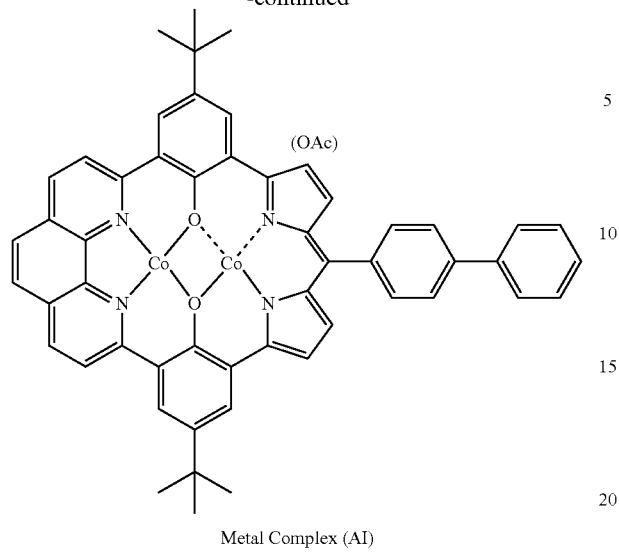

Metal Complex (AI)

-continued

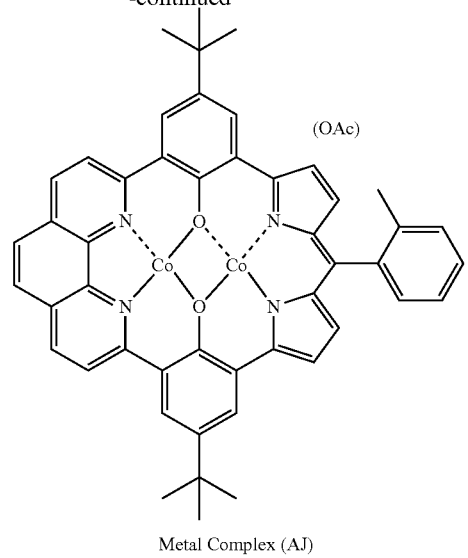

Metal Complex (AJ)

While a mixed solution of 5 mL of methanol and 10 mL of chloroform containing 0.067 g of Macrocyclic Compound (I) and 0.052 g of cobalt acetate tetrahydrate was stirred under a nitrogen atmosphere, the solution was stirred for 6 hours while being heated at 80° C. The resultant solution was concentrated and dried to be solidified. As a result, a blue solid was yielded. This was washed with water to yield Metal Complex (AI).

ESI-MS[M+H]$^+$: m/z=943.0

While a mixed solution of 5 mL of methanol and 5 mL of chloroform containing 0.034 g of Macrocyclic Compound (J) and 0.028 g of cobalt acetate tetrahydrate was stirred under a nitrogen atmosphere, the solution was stirred for 8 hours while being heated at 75° C. The resultant solution was concentrated and dried to be solidified. As a result, a blue solid was yielded. This was washed with water to yield Metal Complex (AJ).

ESI-MS[M.]$^+$: m/z=880.1

Example 31

Metal Complex (AJ) was synthesized in accordance with the following reaction formula.

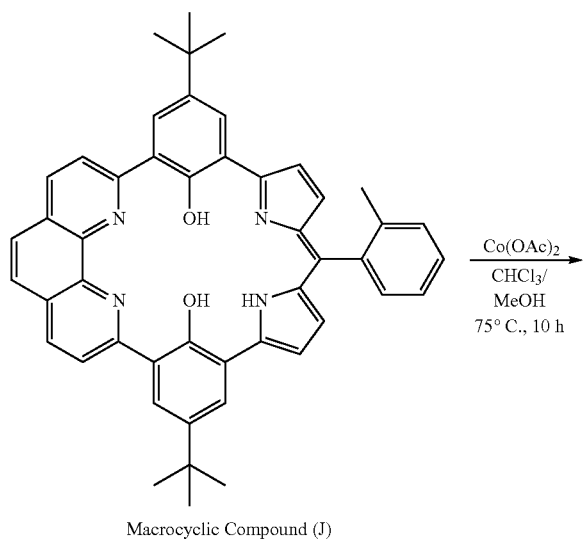

Macrocyclic Compound (J)

Example 32

Metal Complex (AK) was synthesized in accordance with the following reaction formula.

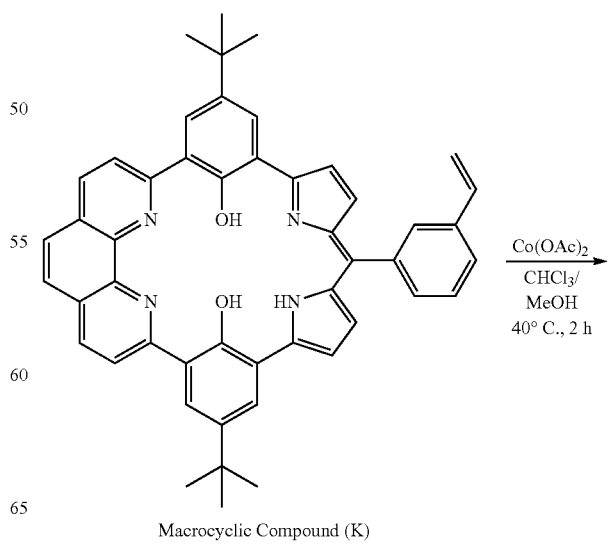

Macrocyclic Compound (K)

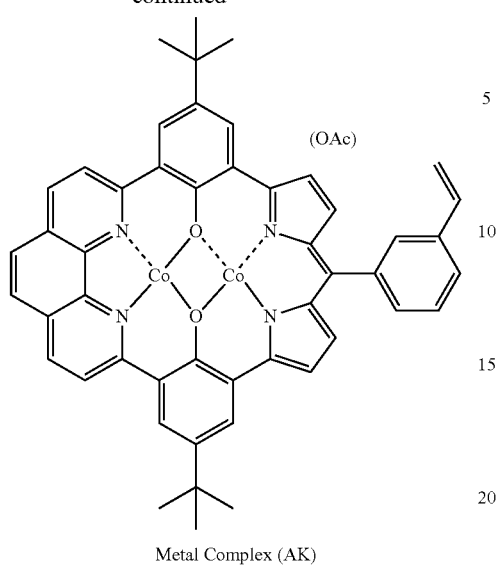

Metal Complex (AK)

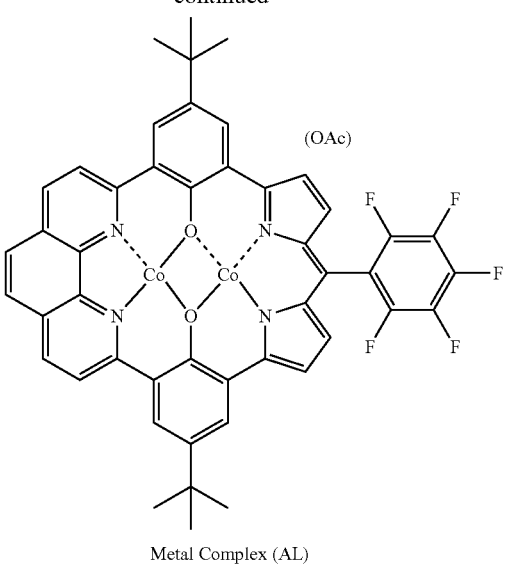

Metal Complex (AL)

While a mixed solution of 10 mL of methanol and 10 mL of chloroform containing 0.071 g of Macrocyclic Compound (K) and 0.055 g of cobalt acetate tetrahydrate was stirred under a nitrogen atmosphere, the solution was stirred for 2 hours while being heated at 40° C. The resultant solution was concentrated and dried to be solidified. As a result, a blue solid was yielded. This was washed with water to yield Metal Complex (AK).

ESI-MS[M.]$^+$: m/z=892.1

While a mixed solution of 5 mL of methanol and 5 mL of chloroform containing 0.021 g of Macrocyclic Compound (L) and 0.014 g of cobalt acetate tetrahydrate was stirred under a nitrogen atmosphere, the solution was stirred for 7 hours while being heated at 60° C. The resultant solution was concentrated and dried to be solidified. As a result, a blue solid was yielded. This was washed with water to yield Metal Complex (AL).

ESI-MS[M+H]$^+$: m/z=957.0

Example 33

Metal Complex (AL) was synthesized in accordance with the following reaction formula.

Example 34

Metal Complex (AM) was synthesized in accordance with the following reaction formula.

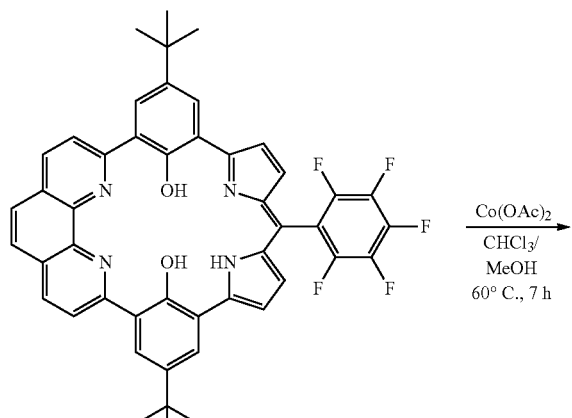

Macrocyclic Compound (L)

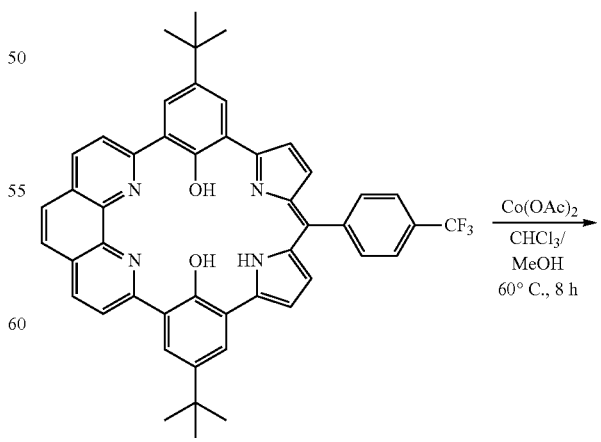

Macrocyclic Compound (M)

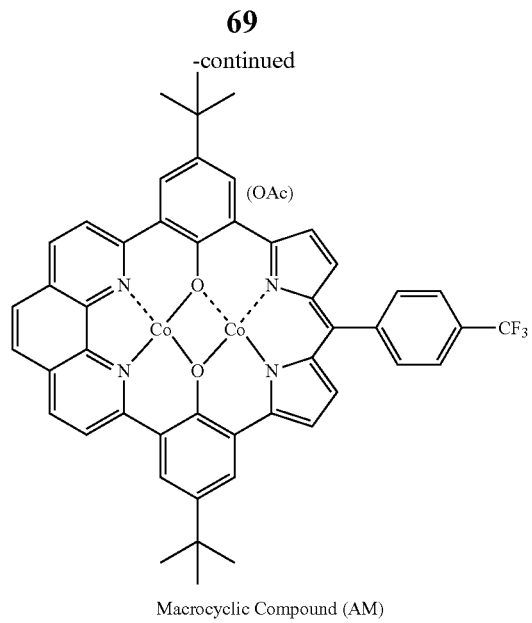

Macrocyclic Compound (AM)

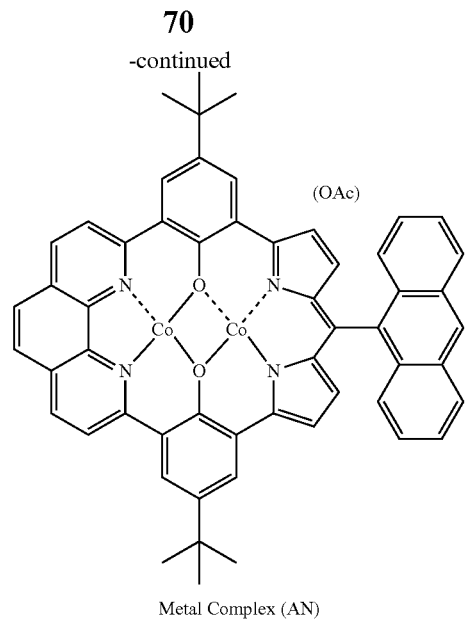

Metal Complex (AN)

While a mixed solution of 5 mL of methanol and 5 mL of chloroform containing 0.015 g of Macrocyclic Compound (M) and 0.011 g of cobalt acetate tetrahydrate was stirred under a nitrogen atmosphere, the solution was stirred for 8 hours while being heated at 60° C. The resultant solution was concentrated and dried to be solidified. As a result, a blue solid was yielded. This was washed with water to yield Metal Complex (AM).

ESI-MS[M.]$^+$: m/z=933.9

While a mixed solution of 5 mL of methanol and 5 mL of chloroform containing 0.034 g of Macrocyclic Compound (N) and 0.026 g of cobalt acetate tetrahydrate was stirred under a nitrogen atmosphere, the solution was stirred for 7 hours while being heated at 60° C. The resultant solution was concentrated and dried to be solidified. As a result, a blue solid was yielded. This was washed with water to yield Metal Complex (AN).

ESI-MS[M.]$^+$: m/z=907.1

Example 35

Metal Complex (AN) was synthesized in accordance with the following reaction formula.

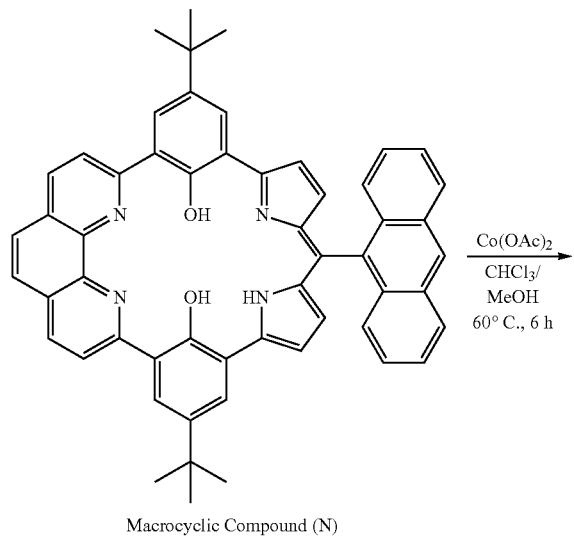

Macrocyclic Compound (N)

Example 36

Metal Complex (AO) was synthesized in accordance with the following reaction formula.

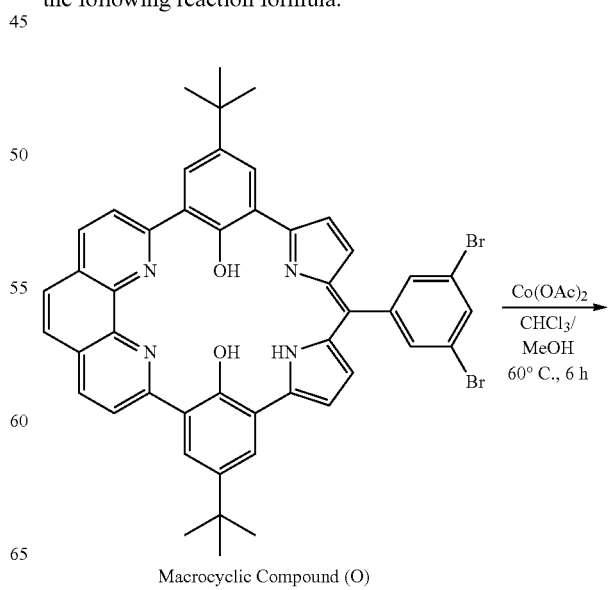

Macrocyclic Compound (O)

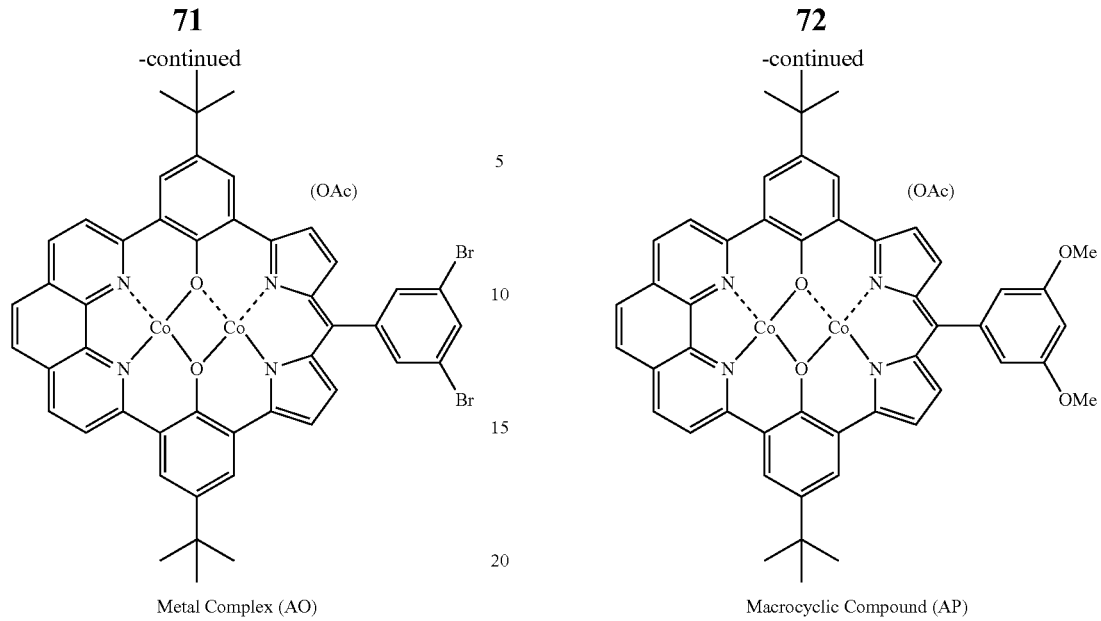

Metal Complex (AO)

Macrocyclic Compound (AP)

While a mixed solution of 5 mL of methanol and 5 mL of chloroform containing 0.025 g of Macrocyclic Compound (O) and 0.020 g of cobalt acetate tetrahydrate was stirred under a nitrogen atmosphere, the solution was stirred for 6 hours while being heated at 60° C. The resultant solution was concentrated and dried to be solidified. As a result, a blue solid was yielded. This was washed with water to yield Metal Complex (AO).

ESI-MS[M.]$^+$: m/z=1023.9

While a mixed solution of 5 mL of methanol and 5 mL of chloroform containing 0.030 g of Macrocyclic Compound (P) and 0.025 g of cobalt acetate tetrahydrate was stirred under a nitrogen atmosphere, the solution was stirred for 3 hours while being heated at 60° C. The resultant solution was concentrated and dried to be solidified. As a result, a blue solid was yielded. This was washed with water to yield Metal Complex (AP).

ESI-MS[M.]$^+$: m/z=926.1

Example 37

Metal Complex (AP) was synthesized in accordance with the following reaction formula.

Example 38

Metal Complex (AQ) was synthesized in accordance with the following reaction formula.

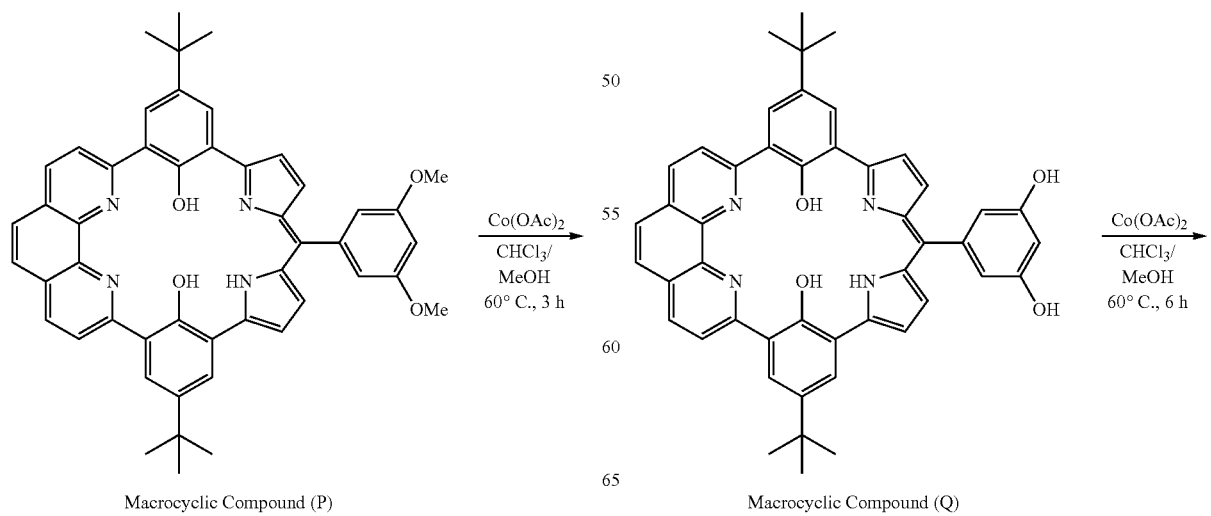

Macrocyclic Compound (P)

Macrocyclic Compound (Q)

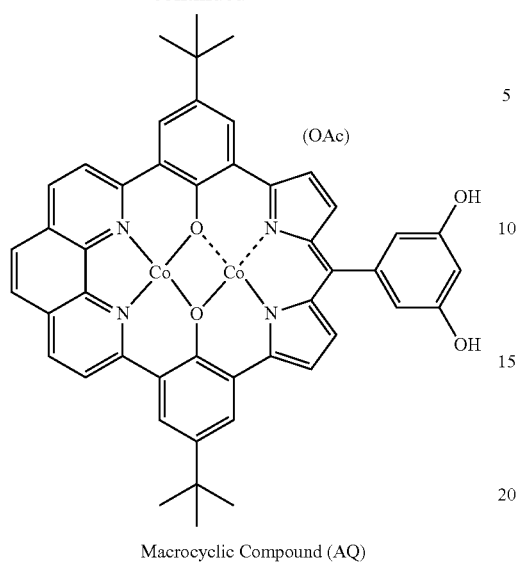

Macrocyclic Compound (AQ)

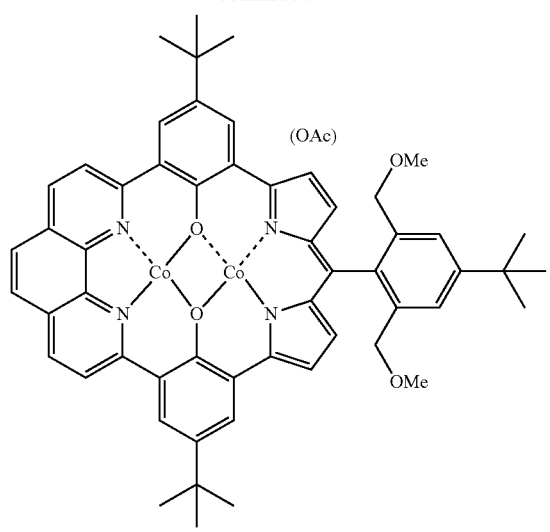

Macrocyclic Compound (AR)

While a mixed solution of 10 mL of methanol and 10 mL of chloroform containing 0.050 g of Macrocyclic Compound (Q) and 0.037 g of cobalt acetate tetrahydrate was stirred under a nitrogen atmosphere, the solution was stirred for 6 hours while being heated at 60° C. The resultant solution was concentrated and dried to be solidified. As a result, a blue solid was yielded. This was washed with water to yield Metal Complex (AQ).

ESI-MS[M.]$^+$: m/z=898.1

While a mixed solution of 5 mL of methanol and 5 mL of chloroform containing 0.025 g of Macrocyclic Compound (R) and 0.026 g of cobalt acetate tetrahydrate was stirred under a nitrogen atmosphere, the solution was stirred for 6 hours while being heated at 60° C. The resultant solution was concentrated and dried to be solidified. As a result, a blue solid was yielded. This was washed with water to yield Metal Complex (AR).

ESI-MS[M.]$^+$: m/z=1010.1

Example 39

Metal Complex (AR) was synthesized in accordance with the following reaction formula.

Example 40

Metal Complex (AS) was synthesized in accordance with the following reaction formula.

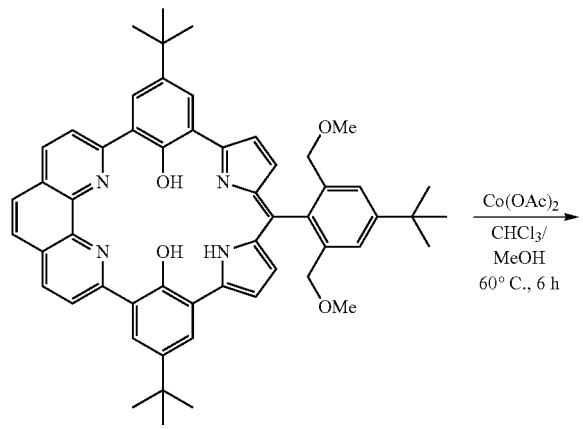

Macrocyclic Compound (R)

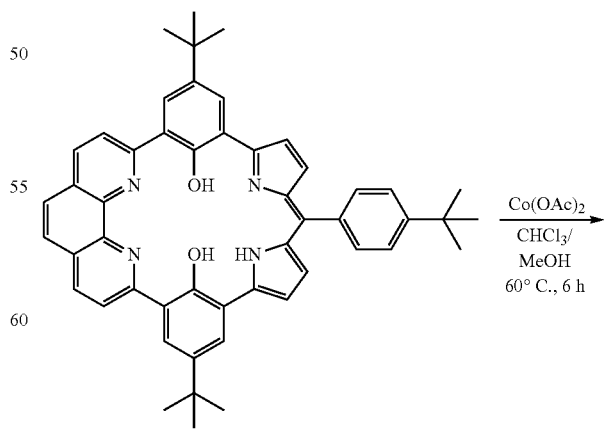

Macrocyclic Compound (S)

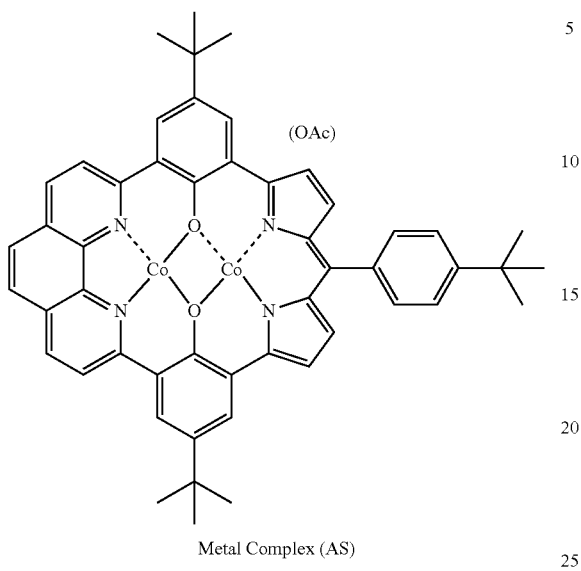

Metal Complex (AS)

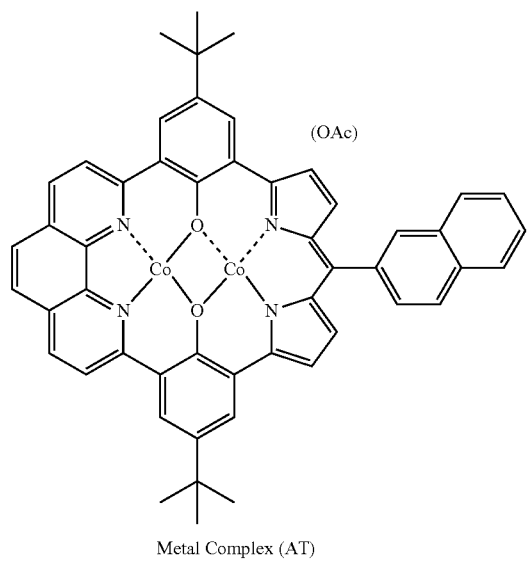

Metal Complex (AT)

While a mixed solution of 5 mL of methanol and 5 mL of chloroform containing 0.032 g of Macrocyclic Compound (S) and 0.023 g of cobalt acetate tetrahydrate was stirred under a nitrogen atmosphere, the solution was stirred for 6 hours while being heated at 60° C. The resultant solution was concentrated and dried to be solidified. As a result, a blue solid was yielded. This was washed with water to yield Metal Complex (AS).

ESI-MS[M.]$^+$: m/z=922.1

Example 41

Metal Complex (AT) was synthesized in accordance with the following reaction formula.

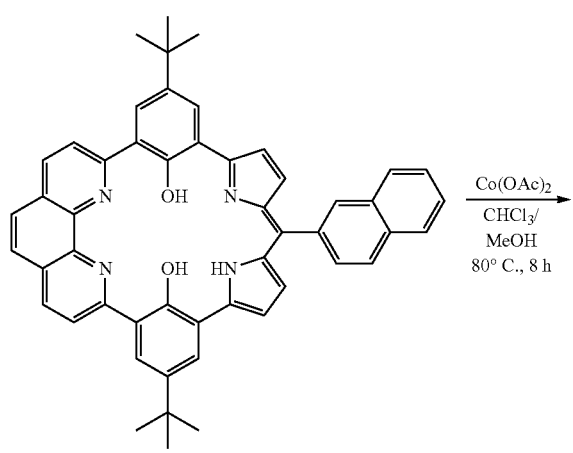

Macrocyclic Compound (T)

While a mixed solution of 5 mL of methanol and 5 mL of chloroform containing 0.042 g of Macrocyclic Compound (T) and 0.035 g of cobalt acetate tetrahydrate was stirred under a nitrogen atmosphere, the solution was stirred for 8 hours while being heated at 80° C. The resultant solution was concentrated and dried to be solidified. As a result, a blue solid was yielded. This was washed with water to yield Metal Complex (AT).

ESI-MS[M.]$^+$: m/z=916.0

Example 42

Metal Complex (AV) was synthesized in accordance with the following reaction formula.

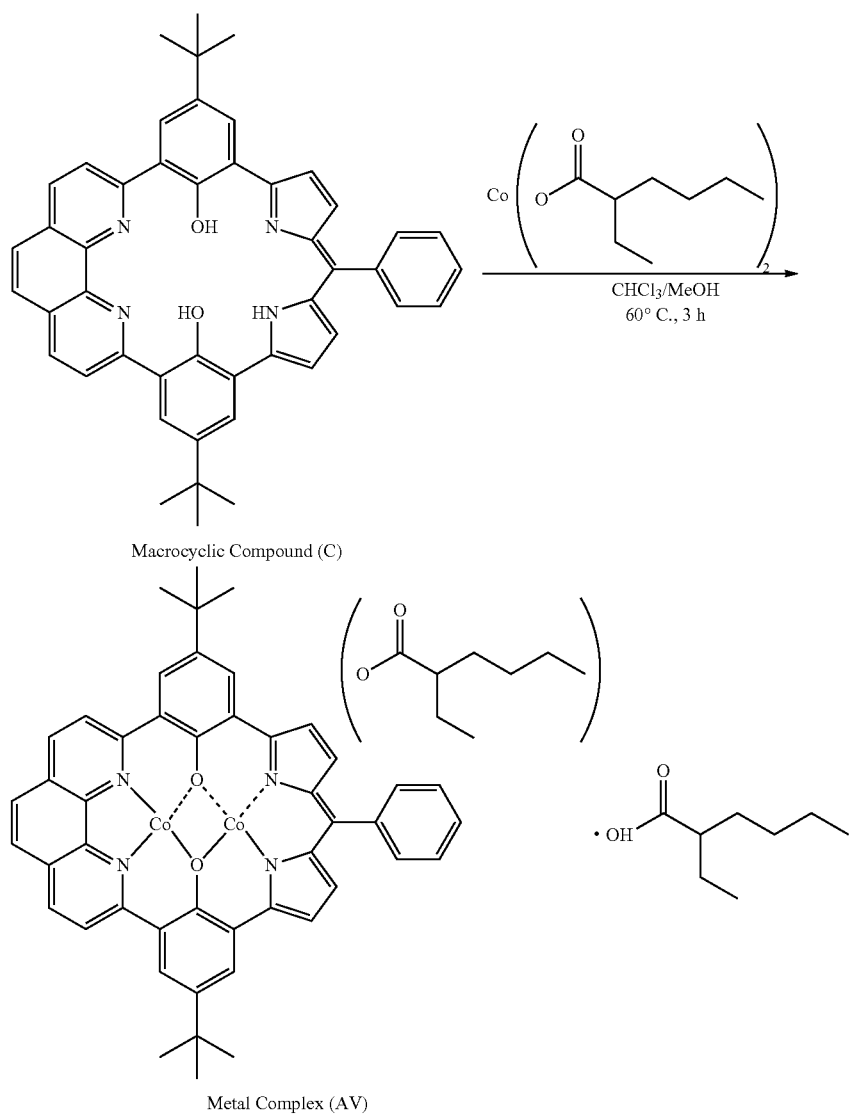

While a mixed solution of 5 mL of methanol and 5 mL of chloroform containing 0.047 g of Macrocyclic Compound (C) and 0.059 g of cobalt 2-ethylhexanoate (65 wt % in mineral spirit, manufactured by Aldrich) was stirred under a nitrogen atmosphere, the solution was stirred for 6 hours while being heated at 60° C. The resultant solution was concentrated and dried to be solidified. As a result, a blue solid was yielded. This was washed with water to yield Metal Complex (AV).

ESI-MS [M.]$^+$: m/z=1094.1

Example 43

Metal Complex (AW) was synthesized in accordance with the following reaction formula.

In 50 ml of propionic acid, 0.121 g of Compound (B) and 0.100 g of a benzaldehyde polymer carrier (loading about 2 mmol/g, resin, 100-300 mesh, manufactured by Fluka Company) were dispersed, and the dispersion was heated at 140° C. for 7 hours. Thereafter, to a back residue having been obtained by distilling away propionic acid, a mixed solution of 20 ml of methanol and 20 ml of chloroform containing 0.110 g of cobalt acetate tetrahydrate was added in a nitrogen atmosphere and stirred for 8 hours while being heated at 50° C. The resultant solution was concentrated and dried to be solidified. As a result, a black solid was yielded. This was washed with chloroform and methanol to yield Metal Complex (AW).

Elementary Analysis Value: C: 73.34, H: 6.13, N: 3.18, Co: 4.88.

Example 44

Metal Complex Mixture (BX) was synthesized in accordance with the following reaction formula.

Under a nitrogen atmosphere, 0.010 g of Metal Complex (AK) was dissolved in 3.000 g of methanol. Further, to the resultant solution, 0.010 g of 2,2'-azobis-(2,4-dimethylvaleronitrile) manufactured by Wako Pure Chemical Industries, Ltd., 0.305 g of acrylonitrile manufactured by TCI (Tokyo Chemical Industries Co., Ltd.), 0.019 g of acrylic acid manufactured by Wako Pure Chemical Industries, Ltd. and 0.040 g of KETJEN BLACK 600 JD manufactured by Lion Corporation were each added and heated while being stirred at 60°

C. In an hour, the precipitate was taken by filtration, and was then dried, whereby 0.066 g of Metal Complex Mixture (BX) was obtained.

Elementary Analysis Value: C: 86.37; H: 2.83, N: 5.54, Co: 1.40.

Examples 45 to 64

Each of the Metal Complexes (AA) to (AT), and a carbon carrier (trade name: Ketjen Black EC300J (bulk density: 100 to 145 kg/m$^3$); or trade name: Ketjen Black 600JD (bulk density: 15 to 50 kg/m$^3$); each manufactured by Lion Corporation) were mixed with each other in a mass ratio of 1:4 and the mixture was stirred at room temperature in ethanol. Then, the mixture was dried at room temperature under a reduced pressure of 200 Pa for 12 hours to prepare Metal Complex Mixtures (BA) to (BT). Compositions of the mixtures are shown in Table 1.

more. That is, each of the metal complexes and the metal complex mixtures was subjected to two-hour heat treatment at an aimed temperature under nitrogen atmosphere using a tubular furnace.

The tubular furnace used for the heat treatment and heat treatment conditions are shown below.

Tubular furnace: EPKRO-14R, program-controllable opening and closing type tubular furnace, manufactured by Isuzu Seisakusho Heat treatment atmosphere: nitrogen gas flow 200 mL/min Rate of temperature increase and rate of temperature decrease: 200° C./h Table 2 shows the used metal complexes or metal complex mixtures, names of the modified metal complex obtained by the heat treatment, heat treatment temperature, and mass reduction rate after the treatment. Further, the carbon content (elemental analysis value) after the heat treatment is also shown.

TABLE 1

| Example | Used Metal Complex | Carbon Complex | Obtained Metal Complex Mixture |
|---|---|---|---|
| 45 | Metal Complex (AA) | KB300 | Metal Complex Mixture (BA) |
| 46 | Metal Complex (AB) | KB300 | Metal Complex Mixture (BB) |
| 47 | Metal Complex (AC) | KB300 | Metal Complex Mixture (BC) |
| 48 | Metal Complex (AD) | KB300 | Metal Complex Mixture (BD) |
| 49 | Metal Complex (AE) | KB300 | Metal Complex Mixture (BE) |
| 50 | Metal Complex (AF) | KB300 | Metal Complex Mixture (BF) |
| 51 | Metal Complex (AG) | KB300 | Metal Complex Mixture (BG) |
| 52 | Metal Complex (AH) | KB300 | Metal Complex Mixture (BH) |
| 53 | Metal Complex (AI) | KB300 | Metal Complex Mixture (BI) |
| 54 | Metal Complex (AJ) | KB300 | Metal Complex Mixture (BJ) |
| 55 | Metal Complex (AK) | KB300 | Metal Complex Mixture (BK) |
| 56 | Metal Complex (AL) | KB300 | Metal Complex Mixture (BL) |
| 57 | Metal Complex (AM) | KB300 | Metal Complex Mixture (BM) |
| 58 | Metal Complex (AN) | KB300 | Metal Complex Mixture (BN) |
| 59 | Metal Complex (AO) | KB600 | Metal Complex Mixture (BO) |
| 60 | Metal Complex (AP) | KB300 | Metal Complex Mixture (BP) |
| 61 | Metal Complex (AQ) | KB600 | Metal Complex Mixture (BQ) |
| 62 | Metal Complex (AR) | KB600 | Metal Complex Mixture (BR) |
| 63 | Metal Complex (AS) | KB600 | Metal Complex Mixture (BS) |
| 64 | Metal Complex (AT) | KB600 | Metal Complex Mixture (BT) |

Examples 65 to 72

A heat treatment was carried out in a manner that the mass reduction rate by the heat treatment became 5 mass % or

TABLE 2

| Example | Used Metal Complex Mixture | Heat Treatment Temperature (° C.) | Obtained Modified Metal Complex | Mass Reduction Rate (%) | Carbon Content (%) |
|---|---|---|---|---|---|
| 65 | Metal Complex Mixture (BB) | 800 | Modified Metal Complex (CB) | 9.68 | 93.10 |
| 66 | Metal Complex Mixture (BC) | 800 | Modified Metal Complex (CC) | 11.90 | 91.70 |
| 67 | Metal Complex Mixture (BN) | 600 | Modified Metal Complex (CN) | 6.90 | 90.98 |
| 68 | Metal Complex Mixture (BO) | 600 | Modified Metal Complex (CO) | 6.78 | 91.03 |
| 69 | Metal Complex Mixture (BP) | 600 | Modified Metal Complex (CP) | 5.00 | 90.39 |
| 70 | Metal Complex Mixture (BQ) | 600 | Modified Metal Complex (CQ) | 17.07 | 90.58 |
| 71 | Metal Complex Mixture (BR) | 600 | Modified Metal Complex (CRA) | 11.11 | 92.55 |
| 72 | Metal Complex Mixture (BR) | 800 | Modified Metal Complex (CRB) | 14.29 | 93.66 |

Here, modified metal complexes obtained by heat treatments to Metal Complex Mixtures (BB), (BC), (BN), (BO), (BP), (BQ), and (BR) described above are referred to as Modified Metal Complexes (CB), (CC), (CN), (CO), (CP), (CQ), (CRA) and (CRB), respectively.

Comparative Example 1

Synthesis of Comparative Complex

Comparative Complex was synthesized according to the following reaction formula in accordance with the method described in Australian Journal of Chemistry, 23, 2225 (1970).

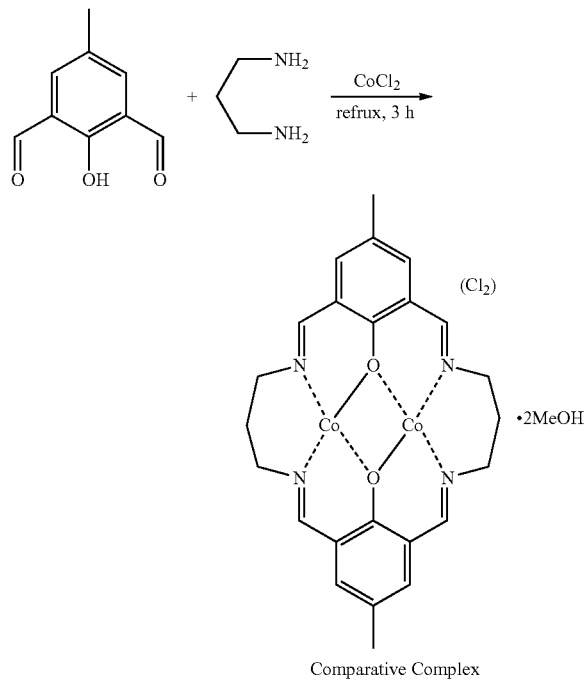

Comparative Complex

Under a nitrogen atmosphere, solution of 1.9 g of cobalt chloride hexahydrate and 1.31 g of 4-methyl-2,6-diformylphenol in 50 mL of methanol was charged into a 100-mL egg plant flask, and the solution was stirred at room temperature. Solution of 0.59 g of 1,3-propanediamine in 20 mL of methanol was gradually added to the solution. The above mixture was refluxed for 3 hours, whereby a dark brown precipitate was produced. The precipitate was taken by filtration, and was then dried, whereby Comparative Complex was obtained (amount: 1.75 g).
Elementary Analysis Value (%)
Calculated Value $(C_{26}H_{34}Cl_2CO_2N_4O_4)$; C, 47.65; H, 5.23; N, 8.55.
Actual Measurement Value: C, 46.64; H, 5.02; N, 8.58.

Comparative Example 2

Comparative Complex and a carbon carrier (Ketjen black EC300J (trade name) manufactured by Lion Corporation) were mixed with each other at a ratio by mass of 1:4, and then the mixture was stirred in methanol at room temperature. Thereafter, the resultant was dried at room temperature under a reduced pressure of 1.5 Torr for 12 hours to obtain Comparative Complex Mixture.

Reference Example 1

A change in mass (TGA) of each of Metal Complex (AB), Metal Complex (AC), Metal Complex (AG), Metal Complex (AH), Metal Complex (AI), Metal Complex (AT), Metal Complex (AJ), Metal Complex (AN), and Metal Complex (AR) upon heat treatment was measured with a thermogravimetric/differential thermal analyzer (EXSTAR-6300 manufactured by Seiko Instruments Inc., hereinafter referred to as thermal analyzer). Conditions for the measurement were as follows: the measurement was performed under a nitrogen atmosphere (at a rate of temperature increase of 10° C./min), and an alumina dish was used in the heat treatment. Table 3 shows the mass reduction rate (percentage) at 800° C.

TABLE 3

|  | Mass Reduction Rate at 800° C. (%) |
| --- | --- |
| Metal Complex (AB) | 37.99 |
| Metal Complex (AC) | 38.46 |
| Metal Complex (AG) | 44.79 |
| Metal Complex (AH) | 35.69 |
| Metal Complex (AI) | 30.52 |
| Metal Complex (AT) | 42.89 |
| Metal Complex (AJ) | 41.13 |
| Metal Complex (AN) | 37.42 |
| Metal Complex (AR) | 37.02 |
| Comparative Complex | 50.41 |

As is apparent from Table 3, each of Metal Complexes (AB), (AC), (AG), (AH), (AI), (AT), (AJ), (AN), and (AR) of the present invention showed a mass reduction rate (percentage) smaller than those of the Comparative Complex. Accordingly, the metal complexes of the present invention have excellent in heat resistance.

[Preparation of Electrode]

As the electrode, a ring disk electrode was used in which the disk part was made of glassy carbon (4.0 mmφ) and the ring part was made of Pt (ring inside diameter: 5.0 mm, ring outside diameter: 7.0 mm).

0.6 mL of water, 0.4 mL of ethanol and 20 mL of 5 wt % Nafion solution (trade name, manufactured by Aldrich) were added in a sample bottle containing 2 mg of the above Metal Complex Mixture or Modified Metal Complex was dispersed ultrasonically for 30 minutes. 4.44 µL of the obtained suspension solution was dripped on the disk part of the above electrode, followed by drying at room temperature for over night to obtain an electrode for measurement.

[Evaluation of Oxygen-Reduction Ability by Rotating Ring Disk Electrode]

The electrode prepared above was rotated to evaluate the current value of oxygen-reduction reaction at the time. The measurements were conducted at room temperature under a nitrogen atmosphere and under an oxygen atmosphere, and the value obtained by subtracting the current value measured under a nitrogen atmosphere from the current value measured under an oxygen atmosphere was defined as the oxygen-reduction current value. The measuring device and measuring conditions are as follows.

Measuring Device

Product manufactured by BAS Inc.

RRDE-2 rotating ring disk electrode device

ALS model 701C dual electrochemical analyzer

Measuring Condition

Cell solution: 0.05 mol/L aqueous sulfuric acid solution (oxygen saturated)

Temperature of solution: 25° C.

Reference electrode: Silver/Silver chloride electrode (saturated KCl)

Counter electrode: Platinum wire

Sweep speed: 5 mV/s

Electrode rotation speed: 600 rpm

Current densities at the electrical potential of 0.3 V (vs RHE) in an oxygen atmosphere are shown in Table 4.

TABLE 4

| Metal Complex or Modified Metal Complex Supported on Electrode | Current Density (mA/cm$^2$) |
|---|---|
| Metal Complex Mixture (BB) | 2.57 |
| Metal Complex Mixture (BC) | 2.41 |
| Modified Metal Complex (CB) | 1.93 |
| Modified Metal Complex (CC) | 2.01 |
| Metal Complex Mixture (BG) | 2.64 |
| Metal Complex Mixture (BI) | 2.73 |
| Metal Complex Mixture (BL) | 2.21 |
| Modified Metal Complex (CN) | 2.14 |
| Metal Complex Mixture (BP) | 2.17 |
| Modified Metal Complex (CS) | 2.39 |
| Comparative Complex | 0.14 |

As is apparent from Table 4, each of Metal Complex Mixtures (BB), (BC), (BG), (BI), (BL) and (BP) of the present invention shows higher current density than those of the comparative metal complex mixture. That is, the metal complex mixtures of the present invention have excellent oxygen-reduction ability.

Further, each of Modified Metal Complexes (CB), (CC), (CN), and (CS) of the present invention also shows higher current density than those of the comparative metal complex mixture. That is, the modified metal complexes of the present invention have excellent oxygen-reduction ability.

INDUSTRIAL APPLICABILITY

The metal complex prepared from using the macrocyclic compound of the present invention is excellent in heat resistance and acid resistance. That is, the metal complex of the present invention can serve as a catalyst for a wide variety of applications and therefore the metal complex is industrially useful.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. A compound represented by formula (1):

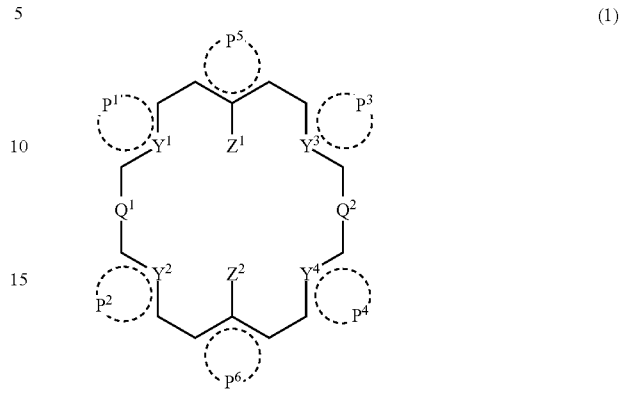

(1)

wherein $Y^1$ to $Y^4$ each independently represent any one of the following groups:

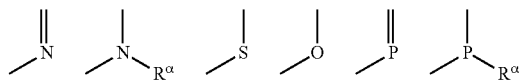

in which $R^\alpha$ represents a hydrogen atom or a monovalent hydrocarbon group; $P^1$ represents a group of atoms necessary for forming a heterocyclic ring together with $Y^1$ and the two carbon atoms adjacent to $Y^1$; $P^2$ represents a group of atoms necessary for forming a heterocyclic ring together with $Y^2$ and the two carbon atoms adjacent to $Y^2$; $P^3$ represents a group of atoms necessary for forming a heterocyclic ring together with $Y^3$ and the two carbon atoms adjacent to $Y^3$; $P^4$ represents a group of atoms necessary for forming a heterocyclic ring together with $Y^4$ and the two carbon atoms adjacent to $Y^4$; $P^5$ represents a group of atoms necessary for forming a phenol ring structure together with the carbon atom to which $Z^1$ bonds and the two carbon atoms adjacent to the carbon atom to which $Z^1$ bonds; $P^6$ represents a group of atoms necessary for forming a phenol ring structure together with the carbon atom to which $Z^2$ bonds and the two carbon atoms adjacent to the carbon atom to which $Z^2$ bonds; $P^1$ and $P^2$, $P^2$ and $P^6$, $P^6$ and $P^4$, $P^4$ and $P^3$, $P^3$ and $P^5$, and $P^5$ and $P^1$ optionally combine with each other to form a ring; $Q^1$ and $Q^2$ each independently represent a connecting group or a direct binding; and $Z^1$ and $Z^2$ each independently represent a hydroxyl group.

2. The compound according to claim 1, wherein, in formula (1), the group of atoms represented by $P^1$ is a group of atoms necessary for forming an aromatic heterocyclic ring together with $Y^1$ and the two carbon atoms adjacent to $Y^1$; the group of atoms represented by $P^2$ is a group of atoms necessary for forming an aromatic heterocyclic ring together with $Y^2$ and the two carbon atoms adjacent to $Y^2$; the group of atoms represented by $P^3$ is a group of atoms necessary for forming an aromatic heterocyclic ring together with $Y^3$ and the two carbon atoms adjacent to $Y^3$; and the group of atoms represented by $P^4$ is a group of atoms necessary for forming an aromatic heterocyclic ring together with $Y^4$ and the two carbon atoms adjacent to $Y^4$.

3. The compound according to claim 2, wherein, in formula (1), the aromatic heterocyclic ring that is formed by the group of atoms represented by $P^1$ together with $Y^1$ and the two carbon atoms adjacent to $Y^1$, the aromatic heterocyclic ring that is formed by the group of atoms represented by $P^2$ together with $Y^2$ and the two carbon atoms adjacent to $Y^2$, the aromatic heterocyclic ring that is formed by the group of atoms represented by $P^3$ together with $Y^3$ and the two carbon atoms adjacent to $Y^3$, and the aromatic heterocyclic ring that is formed by the group of atoms represented by $P^4$ together with $Y^4$ and the two carbon atoms adjacent to $Y^4$, are each a nitrogen-containing aromatic heterocyclic ring.

4. The compound according to claim 3, wherein the compound represented by formula (1) is a compound represented by formula (2):

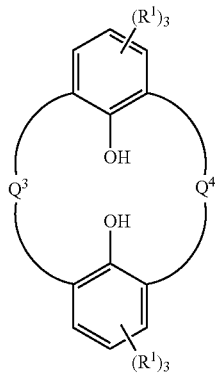

(2)

wherein, in formula (2), $R^1$ represents a hydrogen atom or a substituent, when plural $R^1$s are present, these plural $R^1$s are optionally the same or different from one another; and $Q^3$ and $Q^4$ are each selected from the group consisting of:

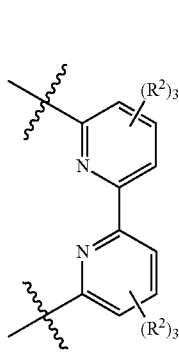
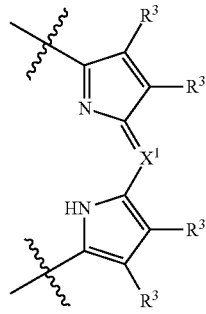
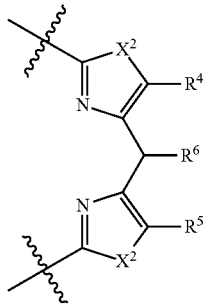

in which

represents a site at which $Q^3$ or $Q^4$ are bonded within the compound of formula (2), and in which $R^2$ represents a hydrogen atom or a substituent, plural $R^2$s are optionally the same or different from one another, and $R^2$s optionally combine with each other to form a ring; $X^1$ represents a nitrogen atom or a trivalent group; $R^3$ represents a hydrogen atom or a substituent, plural $R^3$s are optionally the same or different from one another, and $R^3$s are optionally combine with each other to form a ring; $X^2$s each independently represent a bivalent group represented by any one of the following groups:

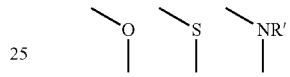

in which R' represents a hydrogen atom or a monovalent hydrocarbon group; $R^4$, $R^5$ and $R^6$ each independently represent a hydrogen atom or a substituent; and $R^4$ and $R^6$, $R^5$ and $R^6$, and $R^4$, $R^5$ and $R^6$ are optionally combine with each other to form a ring.

5. The compound according to claim 4, wherein the compound represented by formula (2) is a compound represented by formula (a1):

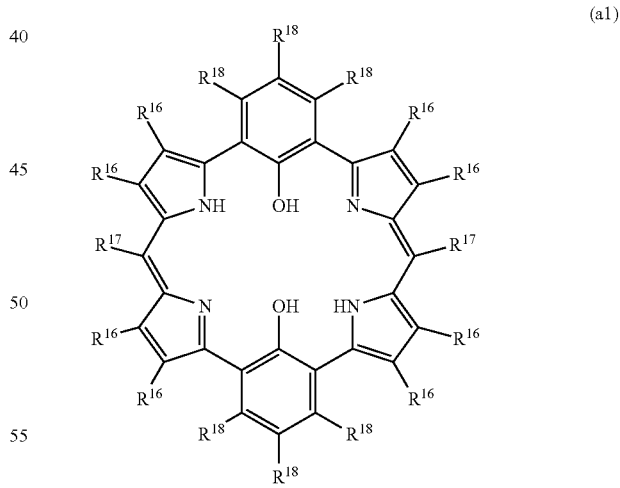

(a1)

wherein, in formula (a1), $R^{16}$ to $R^{18}$ each independently represent a hydrogen atom or a substituent, two adjacent $R^{16}$s and two adjacent $R^{18}$s each optionally combine with each other to form a ring, and plural $R^{16}$s to $R^{18}$s are optionally the same or different from one another.

6. The compound according to claim 4, wherein the compound represented by formula (2) is a compound represented by formula (a2):

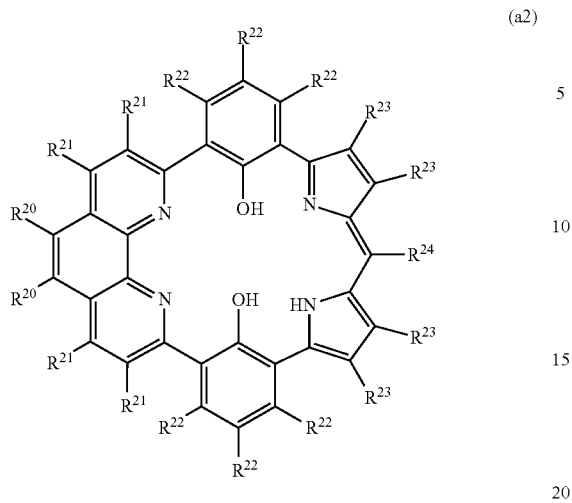
(a2)
wherein, in formula (a2), $R^{20}$ to $R^{24}$ each independently represent a hydrogen atom or a substituent, two adjacent $R^{20}$s, two adjacent $R^{21}$s, two adjacent $R^{22}$s and two adjacent $R^{23}$s each optionally combine with each other to form a ring, and plural $R^{20}$s to $R^{23}$s are optionally the same or different from one another.
* * * * *